(12) United States Patent
Yamazaki et al.

(10) Patent No.: US 7,109,226 B2
(45) Date of Patent: Sep. 19, 2006

(54) PPAR-ACTIVATING COMPOUND AND PHARMACEUTICAL COMPOSITION COMPRISING THE COMPOUND

(75) Inventors: Yukiyoshi Yamazaki, Higashimurayama (JP); Tsutomu Toma, Kodaira (JP); Masahiro Nishikawa, Nagoya (JP); Hidefumi Ozawa, Hachiouji (JP); Ayumu Okuda, Higashimurayama (JP); Takaaki Araki, Higashimurayama (JP); Kazutoyo Abe, Mitaka (JP); Soichi Oda, Aichi (JP)

(73) Assignee: Kowa Co., Ltd., Nagoya (JP)

( * ) Notice: Subject to any disclaimer, the term of this patent is extended or adjusted under 35 U.S.C. 154(b) by 14 days.

(21) Appl. No.: 10/933,467

(22) Filed: Sep. 3, 2004

(65) Prior Publication Data

US 2005/0101636 A1    May 12, 2005

Related U.S. Application Data

(60) Provisional application No. 60/499,357, filed on Sep. 3, 2003.

(30) Foreign Application Priority Data

Sep. 9, 2003   (JP)  .............................. 2003-317353
Oct. 24, 2003  (JP)  .............................. 2003-364817

(51) Int. Cl.
*A61K 31/423*  (2006.01)
*C07D 263/58*  (2006.01)

(52) U.S. Cl. ...................................... 514/375; 548/222
(58) Field of Classification Search ................ 548/222; 514/375, 377
See application file for complete search history.

(56) References Cited

U.S. PATENT DOCUMENTS 6,653,334 B1 * 11/2003 Yamazaki et al. .......... 514/375

FOREIGN PATENT DOCUMENTS

WO   WO 97/28149   8/1997
WO   WO 02/46176   6/2002

OTHER PUBLICATIONS

Isabelle Issemann et al., "Activation of a member of the steroid hormone receptor superfamily by peroxisome proliferators". *NATURE*, vol. 347, pp. 645-650., Oct. 18, 1990.
Christine Dreyer, et al., "Control of the Peroxisomal β-Oxidation Pathway by a Novel Family of Nuclear Hormone Receptors", *CELL*, vol. 68, pp. 879-887, Mar. 6, 1992.
Letter to the Editor, "A Unified Nomenclature System for the Nuclear Receptor Superfamily", *Cell*, vol. 97, pp. 161-163, Apr. 16, 1999.

Kristina Schoonjans, et al., "The peroxisome proliferator activated receptors (PPARs) and their effects on lipid metabolism and adipocyte differentiation", *Biochimica Et Biophysica Acta*, vol. 1302, pp. 93-109. (1996).
Timothy M. Willson, et al., "The PPARs: From Orphan Receptors to Drug Discovery", *Journal of Medicinal Chemistry*, vol. 43, No. 4, pp. 527-550. Feb. 24, 2000.
Mauricio Reginato, et al., "Mechanisms by which Thiazolidinediones Enhance Insulin Action", *TEM*, vol. 10, No. 1, pp. 9-13. (1999).
Akira Okuno, et al., "Troglitazone Increases the Number of Small Adipocytes Without the Change of White Adipose Tissue Mass in Obese Zucker Rats", *J. Clin Invest.*, vol. 101, No. 6, pp. 1354-1361, Mar. 1998.
Jennifer L. Oberfield, et al., "A peroxisome proliferator-activated receptor y ligand inhibits adipocyte differentiation", *Proc. Natl. Acad. Sci USA*, vol. 96, pp. 6102-6106, May 1999.
Harold M. Wright et al., "A Synthetic Antagonist for the Peroxisome Proliferator-activated Receptor y Inhibits Adipocyte Differentiation", *The Journal of Biological Chemistry*, vol. 275, No. 3, pp. 1873-1877. (2000).
Toshimasa Yamauchi, et al., "Inhibitin of RXR and PPARy ameliorates diet-induced obesity and type 2 diabetes", *The Journal of Clinical Investigation*, vol. 108, No. 7, pp. 1001-1013, Oct. 2001.
Didier Auboeuf, et al., "Tissue Distribution and Quantification of the Expression of mRNAs of Peroxisome Proliferator-Activated Receptors and Liver X Receptor-α in Humans, No Alteration in Adipose Tissue of Obese and NIDDM Patients", *Diabetes*, vol. 46, pp. 1319-1327, Aug. 1997.

(Continued)

*Primary Examiner*—Kamal A. Saeed
*Assistant Examiner*—Michael P. Barker
(74) *Attorney, Agent, or Firm*—Oblon, Spivak, McClelland, Maier & Neustadt, P.C.

(57) ABSTRACT

A compound represented by the following formula (1):

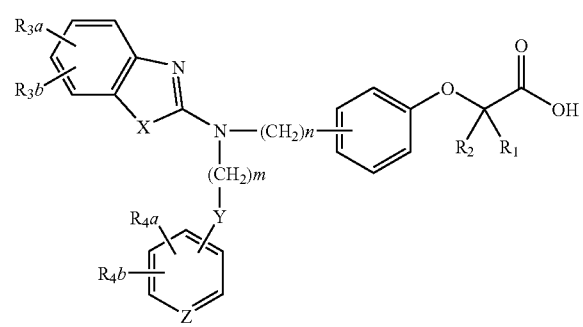

Or a salt thereof; and therapeutic durgs containing the compound. The compound selectively activates PPARα.

5 Claims, 1 Drawing Sheet

OTHER PUBLICATIONS

William R. Oliver, Jr., et al., "A selective peroxisome proliferator-activated receptor δ agonist promotes reverse cholesterol transport", *PNAS*, vol. 98, No. 9, pp. 5306-5311, Apr. 24, 2001.

Yong-Xu Wang, et al., "Peroxisome-Proliferator-Activated Receptor δ Activates Fat Metabolism to Prevent Obesity", *Cell*, vol. 113, pp. 159-170, Apr. 18, 2003.

Isabelle Issemann et al., "Activation of a member of the steroid hormone receptor superfamily by peroxisome proliferators", *Nature*, vol. 347, pp. 645-650., Oct. 18, 1990.

Christine Dreyer, et al., "Control of the Peroxisomal β-Oxidation Pathway by a Novel Family of Nuclear Hormone Receptors", *CELL*, vol. 68, pp. 879-887, Mar. 6, 1992.

Letter to the Editor, "A Unified Nomenclature System for the Nucleur Receptor Superfamily", *Cell*, vol. 97, pp. 161-163, Apr. 16, 1999.

Kristina Schoonjans, et al., "The peroxisome proliferator activated receptors (PPARs) and their effects on lipid metabolism and adipocyte differentiation", *Biochimica Et Biophysica Acta*, vol. 1302, pp. 93-109. (1996).

Timothy M. Willson, et al., "The PPARs: From Orphan Receptors to Drug Discovery", *Journal of Medicinal Chemistry*, vol. 43, No. 4, pp. 527-550. Feb. 24, 2000.

Frank J. Gonzalez, et al., "Mechanism of Action of the Nongenotoxic Peroxisome Proliferators: Role of the Peroxisome Proliferator-Activated Receptor α", *Journal of the National Cancer Institute*. vol. 90, No. 22, Nov. 18, 1998.

Jean-Charles Fruchart, et al., "Peroxisome proliferator-activated receptor-alpha activators regulate genes governing lipoprotein metabolism, vascular inflammation and atherosclerosis", *Current Opinion in Lipidology*, vol. 10, pp. 245-257 (1999).

Johan Auwerx, et al., "Regulation of Triglyceride Metabolism by PPARs: Fibrates and Thiazolidinediones have Distinct Effects", *Journal of Atherosclerosis and Thrombosis*, vol. 3, No. 2, pp. 81-89. (1996).

Bart Staels. et al., "Role of PPAR in the Pharmacological Regulation of Lipoprotein Metabolism by Fibrates and Thiazolidinediones", *Current Pharmaceutical Design*, vol. 3, pp. 1-14, (1997).

Inés Pineda Torra, et al., "Peroxisome proliferator-activated receptor alpha in metabolic disease, inflammation, atherosclerosis and aging", *Current Opinion in Lipidology*, vol. 10, pp. 151-159, (1999).

Joseph Vamecq, et al., "Medical significance of peroxisome proliferator-activated receptors", *THE LANCET*, vol. 354, pp. 141-148, Jul. 10, 1999.

Sander J. Robins, "PPARα ligands and clinical trials: cardiovascular risk reduction with fibrates", *Journal of Cardiovascular Risk*, vol. 8, pp. 195-201. (2001).

Jürgen M. Lehmann, et al., "An Antidiabetic Thiazolidinedione Is a High Affinity Ligand for Peroxisome Proliferator-activated Receptor y (PPARy)", The Journal of Biological Chemistry, vol. 270, No. 22, pp. 12953-12956. (1995).

Joel Berger, et al., "Thiazolidinediones Produce a Conformational Change in Peroxisomal Proliferator-Activated Receptor-y: Binding and Activation Correlate with Antidiabetic Actions in db/db Mice", *Endocrinology*, vol. 137, No. 10, pp. 4189-4195. (1996).

Mauricio Reginato, et al., "Mechanisms by which Thiazolidinediones Enhance Insulin Action", *TEM*, vol. 10, No. 1, pp. 9-13. (1999).

Akira Okuno, et al., "Troglitazone Increases the Number of Small Adipocytes Without the Change of White Adipose Tissue Mass in Obese Zucker Rats", *J. Clin Invest.*, vol. 101, No. 6, pp. 1354-1361, Mar. 1998.

Naoki Sakane, et al., "Glitazones and NIDDM", *The Lancet*, vol. 349, pp. 952, Mar. 29, 1997.

Jennifer L. Oberfield, et al., "A peroxisome proliferator-activated receptor y ligand inhibits adipocyte differentiation", *Proc. Natl. Acad. Sci USA*, vol. 96, pp. 6102-6106, May 1999.

Harold M. Wright et al., "A Synthetic Antagonist for the Peroxisome Proliferator-activated Receptor y Inhibits Adipocyte Differentiation", *The Journal of Biological Chemistry*, vol. 275, No. 3, pp. 1873-1877. (2000).

Toshimasa Yamauchi, et al., "Inhibition of RXR and PPARy ameliorates diet-induced obesity and type 2 diabetes", *The Journal of Clinical Investigation*, vol. 108, No. 7, pp. 1001-1013, Oct. 2001.

Didier Auboeuf, et al., "Tissue Distribution and Quantification of the Expression of mRNAs of Peroxisome Prolifertor-Activated Receptors and Liver X Receptor-α in Humans, No Alteration in Adipose Tissue of Obese and NIDDM Patients", *Diabetes*, vol. 46, pp. 1319-1327, Aug. 1997.

William R. Oliver, Jr., et al., "A selective peroxisome proliferator-activated recepter δ agonist promotes reverse cholesterol transport", *PNAS*, vol. 98, No. 9, pp. 5306-5311, Apr. 2001.

Yong-Xu Wang, et al., "Peroxisome-Proliferator-Activated Receptor δ Activates Fat Metabolism to Prevent Obesity", *Cell*, vol. 113, pp. 159-170, Apr. 18, 2003.

Helen Vosper, et al., "The Peroxisome Proliferator-activated Receptor δ Promotes Lipid Accumulation in Human Macropages", *The Journal of Biological Chemistry*, vol. 276, No. 47, pp. 44258-44265. (2001).

Yaacov Barak, et al., "Effects of peroxisome proliferator-activated receptor δ on placentation, adiposity, and colorectal cancer", *PNAS*, vol. 99, No. 1, pp. 303-308, Jan. 8, 2002.

* cited by examiner

PPAR-ACTIVATING COMPOUND AND PHARMACEUTICAL COMPOSITION COMPRISING THE COMPOUND

BACKGROUND OF THE INVENTION

1. Field of the Invention

The present invention relates to a PPAR activating compound which selectively activates, among peroxisome proliferator-activated receptors (PPARs), α-type PPAR (i.e., PPARα), and is useful as a drug for preventing and/or treating pathological conditions including hyperlipidemia, arteriosclerosis, diabetes, complications of diabetes, inflammation, and heart diseases. The invention also relates to a pharmaceutical composition containing the compound.

2. Background Art

PPARs are known to form a family of nuclear receptors, and three sub-types thereof (α, γ, δ) have already been identified (Nature, 347, 645–650, 1990; Cell, 68, pp. 879–887, 1992; Cell, 97, pp. 161–163, 1999; Biochim. Biophys. Acta., 1302, pp. 93–109, 1996; and Journal of Medicinal Chemistry, 43, pp. 527–550, 2000).

Among the three sub-types, PPARα is expressed predominantly in the liver and is known to be activated by plasticizeres and/or fibrates, such as Wy 14643, clofibrate, fenofibrate, bezafibrate, or gemfibrosil (Journal of the National Cancer Institute, 90, 1702–1709, 1998, Current Opinion in Lipidology, 10, pp. 245–257, 1999).

In mammals, activation of PPARα is known to promote β oxidation of fatty acids and lower the blood triglyceride level. In humans, activation of PPARα decreases levels of blood lipids such as low-density lipoprotein (LDL) cholesterol and very low-density lipoprotein (VLDL) cholesterol. Thus, a PPARα-activator is useful as a drug for preventing and/or treating a disease such as hyperlipidemia. In addition, the PPARα-activator is considered to be useful as a drug for preventing and/or treating pathological conditions such as arteriosclerosis due to increase in the high density lipoprotein (HDL) cholesterol and the suppression of VCAM-1 (one of cell adhesion molecules). Furthermore, the PPARα-activator is considered to be useful as a drug for preventing and/or treating pathological conditions such as diabetes, inflammatory disease, and heart diseases (Journal of Atherosclerosis and Thrombosis, 3, pp. 81–89, 1996; Current Pharmaceutical Design, 3, pp. 1–14, 1997; Current Opinion in Lipidology, 10, pp. 151–159, 1999; Current Opinion in Lipidology, 10, pp. 245–257, 1999; The Lancet, 354, pp. 141–148, 1999; Journal of Medicinal Chemistry, 43, pp. 527–550, 2000; and Journal of Cardiovascular Risk, 8, pp. 195–201, 2001).

PPARγ, which is expressed predominantly in adipocytes, is known to play an important role in differentiating and proliferating adipocytes. Examples of known activators for PPARγ include thiazolidine derivative drugs such as troglitazone, pioglitazone, and rosiglitazone. These drugs are known to induce differentiated adipocytes having reduced insulin sensitivity into small adipocytes having high insulin sensitivity, to thereby improve insulin resistance (Journal of Biological Chemistry, 270, 12953–12956, 1995; Endocrinology, 137, pp. 4189–4195, 1996; Trends Endocrinol. Metab., 10, pp. 9–13, 1999; and J. Clin. Invest., 101, pp. 1354–1361, 1998). However, activation of PPARγ has been reported to have adverse effects on human to increase fat and body weight and causing obesity (The Lancet, 349, pp. 952, 1997). Recently, it has been also reported that antagonizing the PPARγ possibly improves insulin resistance (Proc. Natl. Acad. Sci., 96, pp. 6102–6106, 1999; The Journal of Biological Chemistry, 275, pp. 1873–1877, 2000; and J. Clin. Invest., 108, 1001–1013, 2001).

PPARδ, which is present ubiquitously in the body, is known to take part in lipid metabolism. However, only a few high-selectivity PPARδ activators have been reported, and the biological significance of PPARδ remains unclear. At present, the structures of PPARδ activators are reported in a wide range of literature (Diabetes, 46, 1319–1327, 1997; and Journal of Medicinal Chemistry, 43, pp. 527–550, 2000). In a recent report, a PPARδ activator GW 501516 elevates HDL level in monkeys (Proc. Natl. Acad. Sci., 98, pp. 5306–5311, 2001). Moreover, adipocytes or skeletal muscle cells which are expresses activated PPARδ are reported to promote burning of fat (Cell, 113, pp. 159–170, 2003). However, a compound F, a PPARδ activator, disclosed in WO 97/28149 has an unfavorable effect of accumulating lipids in human macrophages (Journal of Biological Chemistry, 276, pp. 44258–44265, 2001). In addition, experiments using PPARδ-deficient mice indicate that activation of PPARδ induces lipid accumulation (Proc. Natl. Acad. Sci., 99, pp. 303–308, 2002). These phenomena represent two conflicting effects in terms of the progress and alleviation of arteriosclerosis. Thus, the significance of PPARδ on treatment of arteriosclerosis still remains unelucidated.

As described above, a PPARα-selective activator having low selectivity to PPARγ and to PPARδ is expected to be useful for preventing and/or treating, without causing obesity or increase in body weight, pathological conditions such as hyperlipidemia, arteriosclerosis, diabetes, complications of diabetes, inflammation, and heart diseases.

WO 02/46176 discloses a PPAR activator having a structure represented by the following formula:

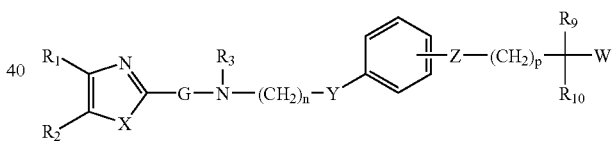

(wherein each of $R_1$ and $R_2$ represents a hydrogen atom, a halogen atom, a nitro group, a C1–C8 alkyl group, a C1–C8 alkoxy group, or a C6–C10 aryl group, or $R_1$ and $R_2$, together with the carbon atoms to which they are bonded, may form a benzene ring; X represents an oxygen atom, a sulfur atom, —$NR_0$— ($R_0$ represents a hydrogen atom or a C1–C8 alkyl group), or —CH=CH—; G represents a single bond or a carbonyl group; $R_3$ represents a C1–C8 alkyl group, a C2–C8 alkenyl group, a C2–C8 alkynyl group, a C3–C7 cycloalkyl group, a C1–C8 alkyl group substituted by a C3–C7 cycloalkyl group, a C6–C10 aryl group, an arylalkyl group (formed of a C6–C10 aryl moiety, with an alkyl moiety having 1 to 8 carbon atoms), a heterocyclic group, or a heterocyclicalkyl group (containing an alkyl moiety having 1 to 8 carbon atoms); n is an integer of 0 to 5; Y represents —$CH_2$—, a carbonyl group, or —CH=CH—; Z represents an oxygen atom or a sulfur atom; p represents an integer of 0 to 5; each of $R_4$ and $R_5$ represents a hydrogen atom or a C1–C8 alkyl group; and W represents a carboxyl group, a C2–C8 alkoxycarbonyl group, a sulfonic acid group, a phosphonic acid group, a cyano group, or a tetrazolyl group).

However, the compounds disclosed in WO 02/46176 act on any sub-type of PPARs (i.e., PPARα, PPARγ, and PPARδ), and thus are not regarded as PPARα-selective activators.

SUMMARY OF THE INVENTION

The present inventors have carried out extensive studies in order to obtain a compound which selectively activates α-type PPAR among other PPARs, and have found that a compound represented by the following formula (1) selectively activates PPARα and is useful as a drug for preventing and/or treating, without causing obesity or increase in body weight, pathological conditions including hyperlipidemia, arteriosclerosis, diabetes, complications of diabetes, inflammation, and heart diseases. The present invention has been accomplished on the basis of this finding.

Accordingly, the present invention provides a compound represented by the following formula (1):

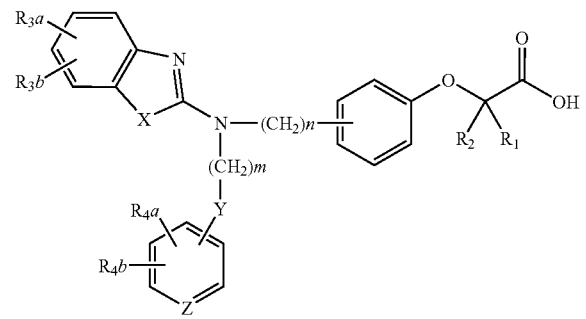

(1)

(wherein each of $R_1$ and $R_2$, which may be identical to or different from each other, represents a hydrogen atom, a methyl group, or an ethyl group; each of $R_{3a}$, $R_{3b}$, $R_{4a}$, and $R_{4b}$, which may be identical to or different from each other, represents a hydrogen atom, a halogen atom, a nitro group, a hydroxyl group, a $C_{1-4}$ alkyl group, a trifluoromethyl group, a $C_{1-4}$ alkoxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, or $R_{3a}$ and $R_{3b}$, or $R_{4a}$ and $R_{4b}$ may be linked together to form an alkylenedioxy group; X represents an oxygen atom, a sulfur atom, or N—$R_5$ ($R_5$ represents a hydrogen atom, a $C_{1-4}$ alkyl group, a $C_{1-4}$ alkylsulfonyl group, or a $C_{1-4}$ alkyloxycarbonyl group); Y represents an oxygen atom, S(O)$_l$ (l is a number of 0 to 2), a carbonyl group, a carbonylamino group, an aminocarbonyl group, a sulfonylamino group, an aminosulfonyl group; Z represents CH or N; n is a number of 1 to 6; and m is a number of 2 to 6) or a salt thereof.

The present invention also provides a drug comprising, as an active ingredient, a compound represented by the above formula (1) or a salt thereof.

The present invention also provides a pharmaceutical composition comprising a compound represented by the above formula (1) or a salt thereof and a pharmacologically acceptable carrier.

The present invention also provides the use, for producing a drug, of a compound represented by the above formula (1) or a salt thereof.

The present invention also provides a method for treating a disease selected from the group consisting of hyperlipidemia, arteriosclerosis, diabetes, complications of diabetes, inflammation and heart diseases, which comprises administering an effective amount of a compound represented by the above formula (1) or a salt thereof to a subject in need.

The compounds of the present invention provide a selective activation effect on PPARα among other PPARs and are useful as therapeutic drugs for preventing and/or treating, without inviting increase in body weight or obesity, pathological conditions such as hyperlipidemia, arteriosclerosis, diabetes, complications of diabetes, inflammation, and heart diseases.

DETAILED DESCRIPTION OF THE INVENTION

Figure 1:
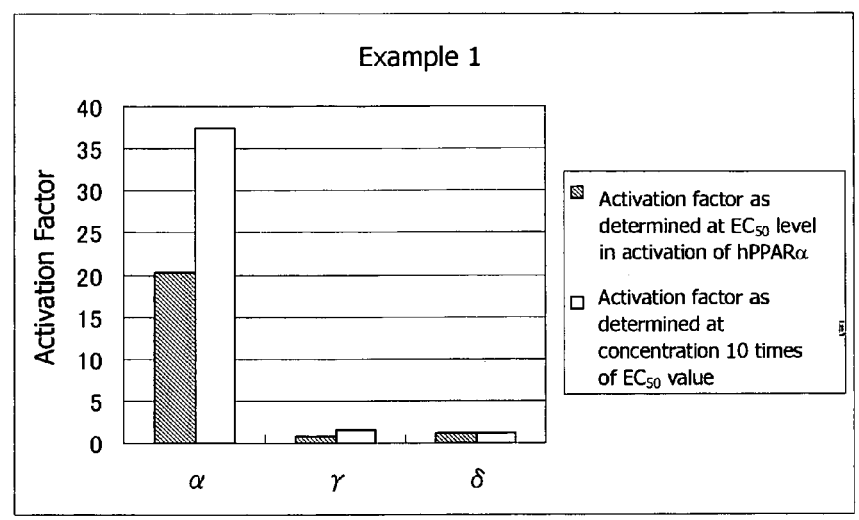
FIG. 1 shows activation factor of the compound of Example 1 with respect to each isoform of PPARs.

As is evident from the formula (1), the compounds of the present invention are characterized by having a structure where a group:

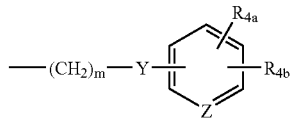

is bonded to a nitrogen atom. Until the present invention, the fact that a compound having the above described structure selectively activates PPARα has remained unknown.

When $R_{3a}$, $R_{3b}$, $R_{4a}$, or $R_{4b}$ in formula (1) is a halogen atom, the halogen atom may be fluorine, chlorine, or bromine, with fluorine and chlorine being preferred.

When $R_{3a}$, $R_{3b}$, $R_{4a}$, $R_{4b}$, or $R_5$ is a $C_{1-4}$ alkyl group, the alkyl group may be methyl, ethyl, n-propyl, isopropyl, or butyl. Of these, methyl is particularly preferred.

When $R_{3a}$, $R_{3b}$, $R_{4a}$, or $R_{4b}$ is a $C_{1-4}$ alkoxy group, the alkoxy group may be methoxy, ethoxy, n-propoxy, isopropoxy, or butoxy. Of these, methoxy is particularly preferred.

When $R_{3a}$, $R_{3b}$, $R_{4a}$, or $R_{4b}$ is a di-$C_{1-4}$ alkylamino group, the dialkylamino group may be dimethylamino, diethylamino, or diisopropylamino. Of these, dimethylamino is particularly preferred.

When $R_{3a}$, $R_{3b}$, $R_{4a}$, or $R_{4b}$ is a $C_{1-4}$ alkylsulfonyloxy group, the alkylsulfonyloxy group may be methylsulfonyloxy or ethylsulfonyloxy. Of these, methylsulfonyloxy is particularly preferred.

When $R_{3a}$, $R_{3b}$, $R_{4a}$, $R_{4b}$, or $R_5$ is a $C_{1-4}$ alkylsulfonyl group, the alkylsulfonyl group may be methylsulfonyl or ethylsulfonyl. Of these, methylsulfonyl is particularly preferred.

When $R_{3a}$, $R_{3b}$, $R_{4a}$, or $R_{4b}$ is a $C_{1-4}$ alkylsulfinyl group, the alkylsulfinyl group may be methylsulfinyl or ethylsulfinyl. Of these, methylsulfinyl is particularly preferred.

When $R_{3a}$, $R_{3b}$, $R_{4a}$, or $R_{4b}$ is a $C_{1-4}$ alkylthio group, the alkylthio group may be methylthio or ethylthio. Of these, methylthio is particularly preferred.

Examples of the alkylenedioxy group which is formed by linking $R_{3a}$ with $R_{3b}$ or by linking $R_{4a}$ with $R_{4b}$ include methylenedioxy and ethylenedioxy. Of these, methylenedioxy is particularly preferred.

When $R_5$ is a $C_{1-4}$ alkyloxycarbonyl group, the alkyloxycarbonyl group may be methyloxycarbonyl or ethyloxycarbonyl. Of these, methyloxycarbonyl is particularly preferred.

In relation to $R_1$ and $R_2$, the following cases are particularly preferred: they are both hydrogen atoms; they are both methyl groups; one is a methyl group and the other is a hydrogen atom; or one is an ethyl group and the other is a hydrogen atom.

X represents an oxygen atom, a sulfur atom, or $N—R_5$, with an oxygen atom being preferred. Y represents an oxygen atom, $S(O)_l$, a carbonyl group, a carbonylamino group, an aminocarbonyl group, a sulfonylamino group, or an aminosulfonyl group. Of these, an oxygen atom is preferred. Z represents CH or N, with CH being preferred. l is a number of 0 to 2, with a number of 2 being preferred. n is a number of 1 to 6, with a number of 1 to 3 being preferred. m is a number of 2 to 6, with a number of 2 to 4 being preferred, and 2 or 3 being particularly preferred.

Examples of the salts of the compounds represented by formula (1) of the present invention include alkali metal salts such as sodium salts and potassium salts; alkaline earth metal salts such as calcium salts and magnesium salts; organic base salts such as ammonium salts and trialkylamine salts; mineral acid salts such as hydrochloric acid salts and sulfuric acid salts; and organic acid salts such as acetic acid salts.

The compound of the present invention may take the form of a solvate such as a hydrate or a geometrical (cis, trans) isomer or an optical isomer. These isomers also fall within the scope of the present invention.

Among the compounds of the present invention, examples of compounds which are preferred due to their high PPARα selectivities include the following compounds or salts thereof:

2-[3-[[N-(benzoxazol-2-yl)-N-3-(4-fluorophenoxy)propyl) aminomethyl]phenoxy]butyric acid, 2-[3-[[N-(benzoxazol-2-yl)-N-2-(4-chlorophenoxy)ethyl) aminoethyl]phenoxy]butyric acid, 2-[3-[[N-(benzoxazol-2-yl)-N-2-(4-fluorophenoxy)ethyl) aminoethyl]phenoxy]butyric acid, 2-[3-[[N-(benzoxazol-2-yl)-N-3-phenoxypropyl)aminomethyl]phenoxy]propionic acid, 3-[[N-(benzoxazol-2-yl)-N-3-phenoxypropyl)aminomethyl] phenoxyacetic acid, 2-[3-[[N-(benzoxazol-2-yl)-N-3-phenoxypropyl)aminomethyl]phenoxy]butyric acid, 2-[3-[[N-(benzoxazol-2-yl)-N-3-(4-methoxyphenoxy)propyl)aminomethyl)phenoxy)butyric acid, 2-[3-[[N-(benzoxazol-2-yl)-N-3-(4-methoxyphenoxy)propyl)aminomethyl]phenoxy]propionic acid.

The compounds of the present invention can be obtained in accordance with, for example, the following production methods described in reaction schemes A to G.

(in the following schemes, $R_1$, $R_2$, $R_{3a}$, $R_{3b}$, $R_{4a}$, $R_{4b}$, m, n, X, Y, and Z have the same meanings as described above; $R_6$ represents a substituent which can protect hydroxyl groups such as a $C_{1-4}$ alkyl group and a trialkylsilyl group (see, for example, "Protective Groups in Organic Synthesis (John Wiley & Sons, Inc.)"); $R_7$ represents a $C_{1-4}$ alkyl group; $R_3$ represents $R_{3a}$ and $R_{3b}$; $R_4$ represents $R_{4a}$ and $R_{4b}$; and p is 1 or 2).

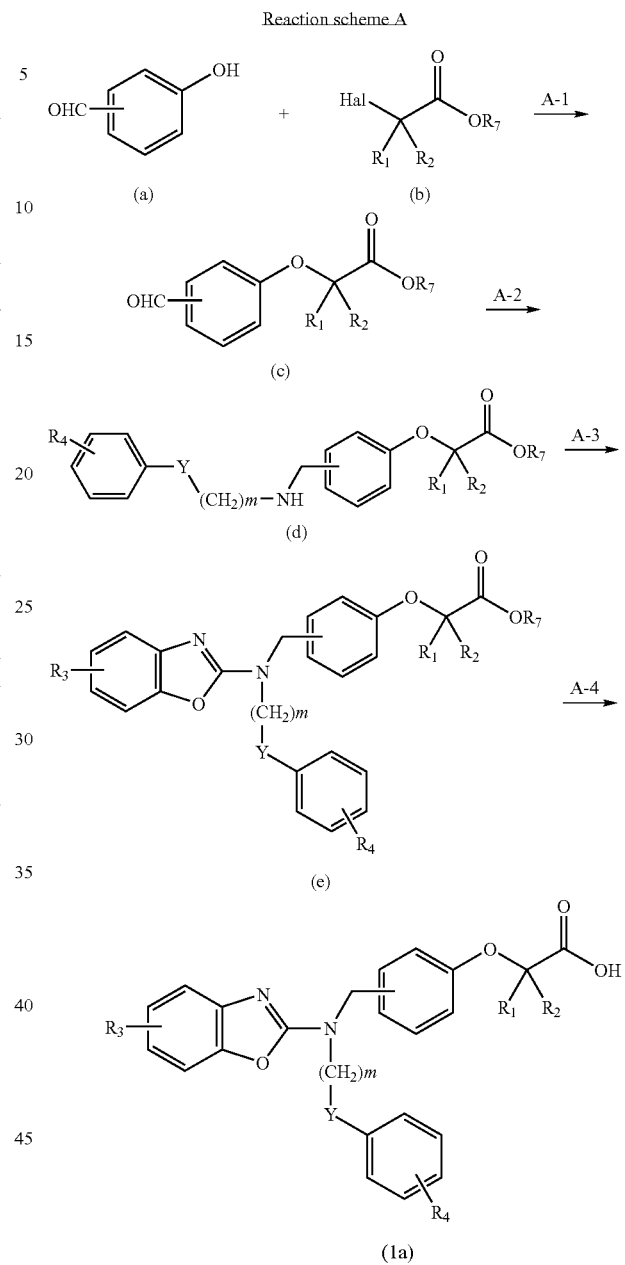

The production method represented by reaction scheme A includes the following steps: A phenol compound (a) is reacted with 2-haloalkylcarboxylic acid ester (b), to thereby produce an aldehyde compound (c); the aldehyde compound (c) is reacted with an amine compound, followed by reduction; the thus-obtained amino compound (d) is reacted with 2-halobenzoxazole, to thereby produce an ester compound (e); and the ester compound (e) is subjected to hydrolysis, to thereby produce the compound (1a) of the present invention.

The first step (A-1) proceeds as follows. A phenol compound (a) is dissolved in a solvent such as N,N-dimethylformamide (DMF), tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Further, a necessary amount of a 2-haloalkylcarboxylic acid ester (b) such as 2-bromoisobutyric acid ester, 2-bromo-n-butyric acid ester, or 2-bromopropionic acid ester is added, and the resultant mixture is allowed to react at a temperature between room temperature and around the boiling point of the solvent under stirring for several hours to 24 hours. The ester is appropriately selected from among tert-butyl esters, ethyl esters, methyl esters, etc.

In the second step (A-2), the aldehyde compound (c) is dissolved in a solvent such as 1,2-dichloroethane, chloroform, dichloromethane, DMF, THF, dioxane, or acetonitrile. Subsequently, a suitably selected amine compound and an acid such as acetic acid are added, followed by reduction with a reducing agent such as sodium triacetoxyborohydride (NaBH(OAc)$_3$). The reaction is carried out by stirring the mixture under cooling or at room temperature for several hours to 24 hours (in an inert gas atmosphere, if necessary).

The third step (A-3) proceeds as follows. The starting amino compound (d) is dissolved in a solvent such as DMF, THF, dioxane, or acetonitrile. 2-Halobenzoxazole such as 2-chlorobenzoxazole is added thereto in the presence of a necessary amount of an inorganic base such as K$_2$CO$_3$, Na$_2$CO$_3$, or Cs$_2$CO$_3$ or an organic base such as triethylamine or diisopropylethylamine. The mixture is allowed to react at a temperature between room temperature and around the boiling point of the solvent under stirring for several hours to 24 hours (in an inert gas atmosphere, if necessary).

The fourth step (A-4) proceeds as follows. In the case where a methyl ester, ethyl ester, or any ester that is easily hydrolyzed with an alkali the starting compound, the ester is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling, or between room temperature and around the boiling point of the solvent. After completion of reaction, the reaction mixture is acidified by use of an acid such as hydrochloric acid. On the other hand, in the case where a tert-butyl ester or any ester that is easily decomposed by an acid is the starting compound, the ester is dissolved in a solvent such as dichloromethane or chloroform, followed by addition of an acid such as trifluoroacetic acid, and the resultant mixture is stirred for several hours to 24 hours under cooling or at room temperature.

Reaction scheme B

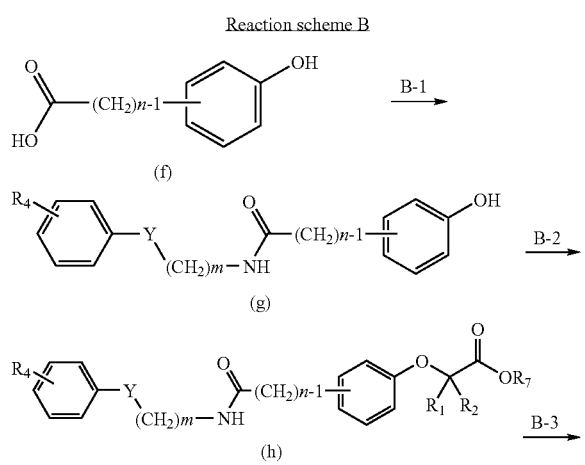

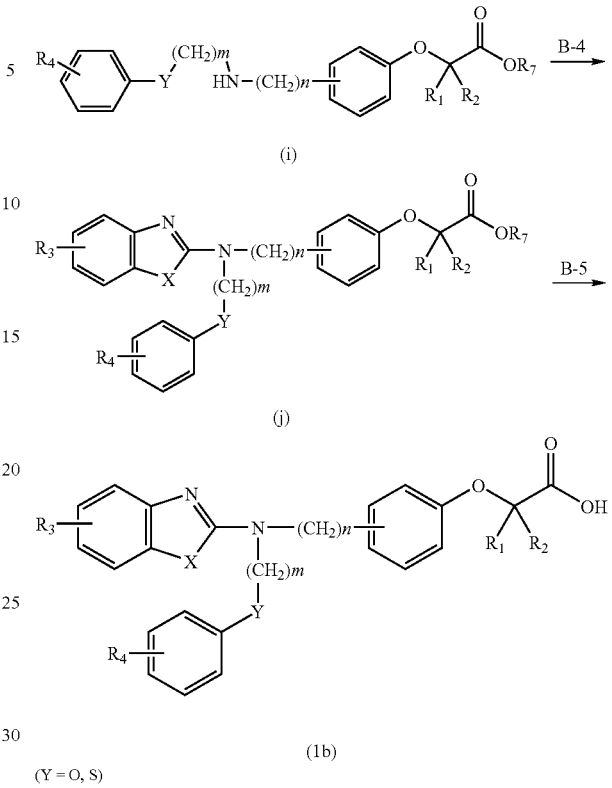

(Y = O, S)

The production method represented by reaction scheme B includes the following steps: The starting carboxylic acid (f) is reacted with an amine, to thereby produce an amidophenol compound (g); the amidophenol compound (g) is reacted with a 2-haloalkylcarboxylic acid ester (b), to thereby produce an amide compound (h); the amide compound (h) is chemically reduced to thereby produce a secondary amino compound (i); the secondary amino compound (i) is reacted with 2-halo-1,3-benzoazole, to thereby produce an ester compound (j); and the ester compound (j) is subjected to hydrolysis, to thereby produce the compound (1b) of the present invention.

The first step (B-1) proceeds as follows. The starting carboxylic acid (f) is dissolved in a solvent such as N,N-dimethylformamide (DMF), tetrahydrofuran (THF), dioxane, acetonitrile, or a mixture of solvents suitably selected therefrom. A suitably selected amine is dissolved in the solvent, and a necessary amount of a condensing agent such as dicyclohexylcarbodiimide or water-soluble carbodiimide (WSC.HCl) (e.g., 1-ethyl-3-(3-dimethylaminopropyl)carbodiimide HCl) is added to the mixture under cooling. Subsequently, according to needs, a compound such as 1-hydroxy-1H-benztriazole (HOBt) or dimethylaminopyridine is added. The resultant mixture is allowed to react at a temperature between room temperature and around the boiling point of the solvent for several hours to 24 hours.

The second step (B-2) proceeds as follows. The phenol compound (g) is dissolved in a solvent such as DMF, THF, dioxane, or acetonitrile. A necessary amount of an inorganic base such as K$_2$CO$_3$, Na$_2$CO$_3$, or Cs$_2$CO$_3$ or an organic base such as triethylamine or diisopropylethylamine is added thereto. Subsequently, a necessary amount of a 2-haloalkylcarboxylic acid ester such as 2-bromoisobutyric acid ester, 2-bromo-n-butyric acid ester, or 2-bromopropionic acid ester is added, and the resultant mixture is allowed to react at a temperature between room temperature and around the boiling point of the solvent under stirring for several hours to 24 hours. The ester is appropriately selected from among tert-butyl esters, ethyl esters, methyl esters, etc.

The third step (B-3) proceeds as follows. The starting amide compound (h) is dissolved in a solvent such as THF or dioxane. Subsequently, if necessary, in an inert gas atmosphere, a necessary amount of a reducing agent such as borane tetrahydrofuran complex ($BH_3.THF$) is added thereto, and the reaction mixture is stirred at room temperature or under heating for several hours to 24 hours.

The fourth step (B-4) proceeds as follows. The starting secondary amino compound (i) is dissolved in a solvent such as DMF, THF, dioxane, or acetonitrile. 2-Halobenzoazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is allowed to react at a temperature between room temperature and around the boiling point of the solvent under stirring for several hours to 24 hours (in an inert gas atmosphere, if necessary).

The fifth step (B-5) proceeds as follows. In the case where a methyl ester, ethyl ester, or any ester that is easily hydrolyzed with an alkali is the starting compound, the ester is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling, or between room temperature and around the boiling point of the solvent. After completion of reaction, the reaction mixture is acidified by use of an acid such as hydrochloric acid. On the other hand, in the case where a tert-butyl ester or any ester that is easily decomposed by an acid is used in the second step, the resultant ester compound which serves as the starting compound of the fifth step is dissolved in a solvent such as dichloromethane or chloroform, followed by addition of an acid such as trifluoroacetic acid, and the resultant mixture is stirred for several hours to 24 hours under cooling or at room temperature.

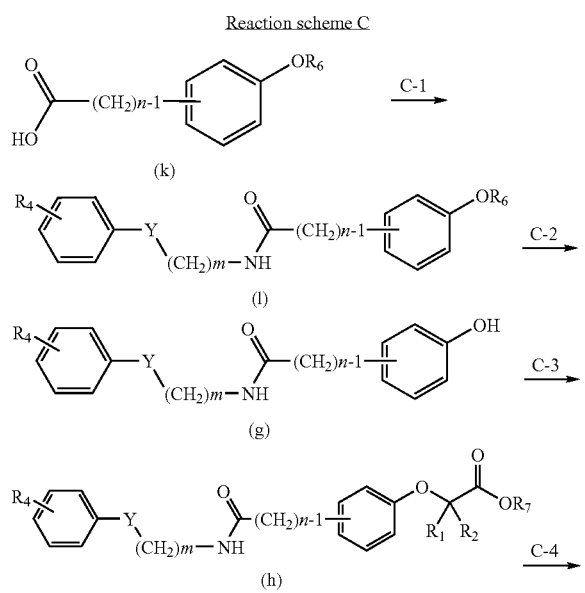

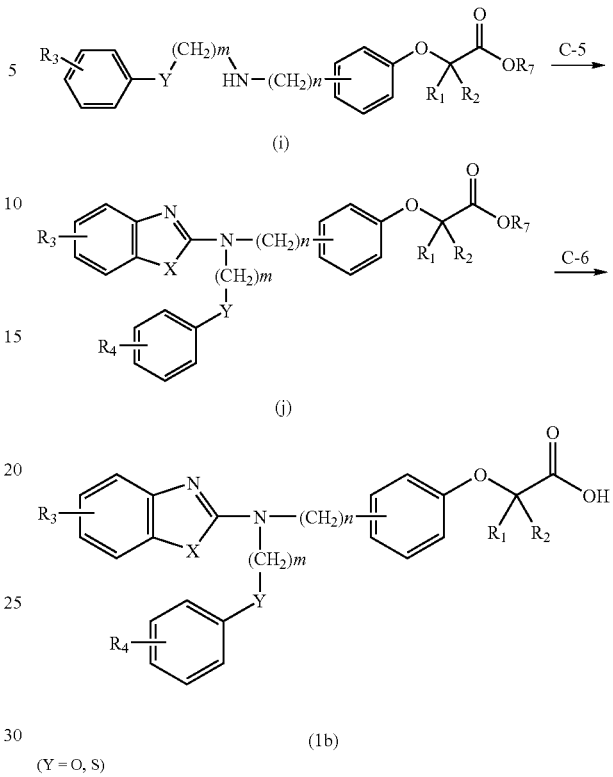

The production method represented by reaction scheme C includes the following steps: A carboxylic acid (k) is reacted with an amine, to thereby produce an amide compound (l); the hydroxyl-protective group is removed from the amide compound (l), to thereby produce a phenol compound (g); the phenol compound (g) is reacted with 2-haloalkylcarboxylic acid ester; the resultant compound is reduced to thereby produce an amino compound (i); the amino compound (i) is reacted with 2-halo-1,3-benzoazole; and the resultant compound is subjected to hydrolysis, to thereby produce the compound of the present invention.

The first step (C-1) proceeds as follows. The starting carboxylic acid (k) is dissolved in a solvent such as N,N-dimethylformamide (DMF), tetrahydrofuran (THF), dioxane, acetonitrile, or a mixture of solvents suitably selected therefrom. A suitably selected amine is dissolved in the solvent, and a necessary amount of a reagent such as dicyclohexylcarbodiimide or WSC.HCl is added to the mixture under cooling. Subsequently, according to needes, a compound such as HOBt or dimethylaminopyridine is added. The resultant mixture is allowed to react at a temperature between room temperature and around the boiling point of the solvent for several hours to 24 hours.

The second step (C-2) proceeds as follows. The amide compound (l) prepared in the first step is dissolved in a solvent such as dichloromethane, chloroform, or chlorobenzene. Thereafter, a Lewis acid such as boron tribromide or aluminum chloride is added thereto, and the mixture is stirred under cooling or at around the boiling point of the solvent for several hours to 24 hours. If $R_6$=H, the reaction in the second step is not required.

The third step (C-3) proceeds as follows. The phenol compound (g) is dissolved in a solvent such as DMF, THF, dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Subsequently, a necessary amount of a 2-haloalkylcarboxylic acid ester such as 2-bromoisobutyric acid ester, 2-bromo-n-butyric acid ester, or 2-bromopropionic acid ester is added, and the resultant mixture is allowed to react at a temperature between room temperature and around the boiling point of the solvent under stirring for several hours to 24 hours. The ester is appropriately selected from among tert-butyl esters, ethyl esters, methyl esters, etc.

The fourth step (C-4) proceeds as follows. The starting amide compound (h) is dissolved in a solvent such as THF or dioxane. Subsequently, if necessary, in an inert gas atmosphere, a necessary amount of a reducing agent such as borane tetrahydrofuran complex ($BH_3$.THF) is added thereto, and the reaction mixture is stirred at room temperature or under heating for several hours to 24 hours.

The fifth step (C-5) proceeds as follows. The starting amino compound (i) is dissolved in a solvent such as DMF, THF, dioxane, or acetonitrile. 2-Halo-1,3-benzoazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is allowed to react at a temperature between room temperature and around the boiling point of the solvent under stirring for several hours to 24 hours (in an inert gas atmosphere, if necessary).

The sixth step (C-6) proceeds as follows. In the case where a methyl ester, ethyl ester, or any ester that is easily hydrolyzed with an alkali is used as the starting compound, the ester is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling, or between room temperature and around the boiling point of the solvent. After completion of reaction, the reaction mixture is acidified by use of an acid such as hydrochloric acid. On the other hand, in the case where a tert-butyl ester or any ester that is easily decomposed by an acid is used as the starting compound, the ester is dissolved in a solvent such as dichloromethane or chloroform, followed by an addition of an acid such as trifluoroacetic acid, and the resultant mixture is stirred for several hours to 24 hours under cooling or at room temperature.

Reaction scheme D

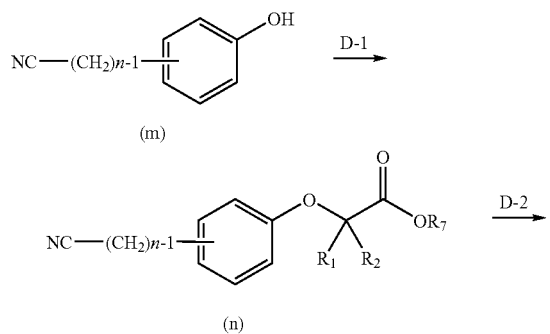

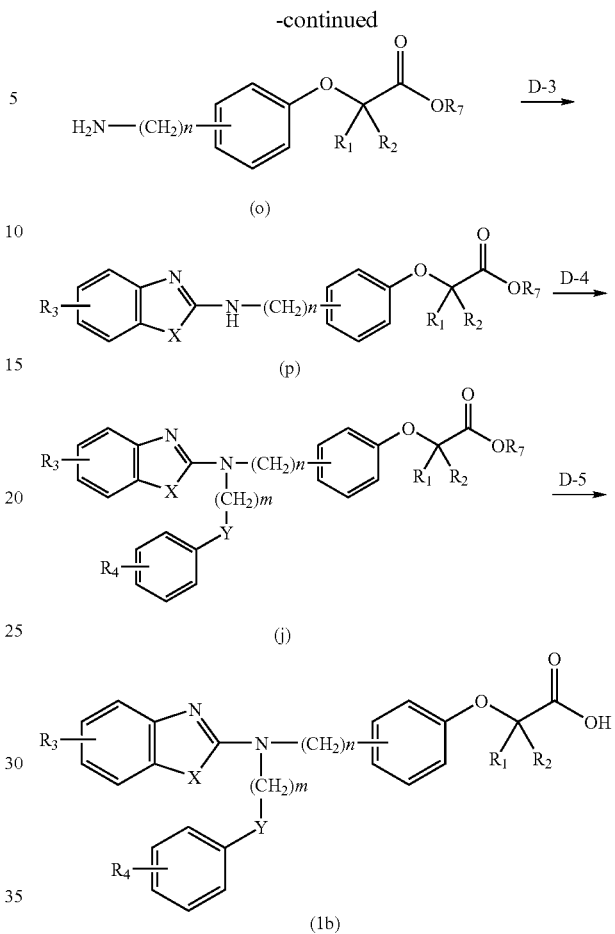

The production method represented by reaction scheme D includes the following steps: A phenol compound (m) is reacted with a 2-haloalkylcarboxylic acid ester, to thereby produce a cyano compound (n); the cyano compound (n) is reduced to thereby produce an amino compound (o); the amino compound (o) is reacted with 2-halo-1,3-benzoazole, to thereby produce an amino compound (p); and the amino compound (p) is reacted with a halide; and the reaction compound is subjected to hydrolysis, to thereby produce the compound (1b) of the present invention.

The first step (D-1) proceeds as follows. A phenol compound (m) is dissolved in a solvent such as N,N-dimethylformamide (DMF), tetrahydrofuran (THF), dioxane, or acetonitrile. A necessary amount of an inorganic base such as potassium carbonate ($K_2CO_3$), sodium carbonate ($Na_2CO_3$), or cesium carbonate ($Cs_2CO_3$) or an organic base such as triethylamine or diisopropylethylamine is added thereto. Subsequently, a necessary amount of a 2-haloalkylcarboxylic acid ester such as 2-bromoisobutyric acid ester, 2-bromo-n-butyric acid ester, or 2-bromopropionic acid ester is added, and the resultant mixture is allowed to react at a temperature between room temperature and around the boiling point of the solvent under stirring for several hours to 24 hours. The ester is appropriately selected from among tert-butyl esters, ethyl esters, methyl esters, etc.

The second step (D-2) proceeds as follows. The starting cyano compound (n) is dissolved in a solvent such as THF or dioxane. Subsequently, if necessary, in an inert gas atmosphere, a necessary amount of a reducing agent such as borane tetrahydrofuran complex (BH$_3$.THF) is added thereto, and the reaction mixture is stirred at room temperature or under heating for several hours to 24 hours.

The third step (D-3) proceeds as follows. The starting amino compound (O) is dissolved in a solvent such as DMF, THF, dioxane, or acetonitrile. 2-Halo-1,3-benzoazole such as 2-chlorobenzoxazole is added thereto in the presence of a necessary amount of an inorganic base such as K$_2$CO$_3$, Na$_2$CO$_3$, or Cs$_2$CO$_3$ or an organic base such as triethylamine or diisopropylethylamine. The mixture is allowed to react at a temperature between room temperature and around the boiling point of the solvent under stirring for several hours to 24 hours (in an inert gas atmosphere, if necessary).

The fourth step (D-4) proceeds as follows. The starting amino compound (p) is dissolved in an inert solvent such as DMF, THF, dioxane, or acetonitrile. A suitably selected halide is added thereto in the presence of a necessary amount of an inorganic base such as K$_2$CO$_3$, Na$_2$CO$_3$, or Cs$_2$CO$_3$ or an organic base such as triethylamine or diisopropylethylamine. The mixture is allowed to react at a temperature between room temperature and around the boiling point of the solvent under stirring for several hours to 24 hours.

The fifth step (D-5) proceeds as follows. In the case where a methyl ester, ethyl ester, or any ester that is easily hydrolyzed with an alkali is used as the starting compound, the ester is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling, or between room temperature and around the boiling point of the solvent. After completion of reaction, the reaction mixture is acidified by use of an acid such as hydrochloric acid. On the other hand, in the case where a tert-butyl ester or any ester that is easily decomposed by an acid is used as the starting compound, the ester is dissolved in a solvent such as dichloromethane or chloroform, followed by addition of an acid such as trifluoroacetic acid, and the resultant mixture is stirred for several hours to 24 hours under cooling or at room temperature.

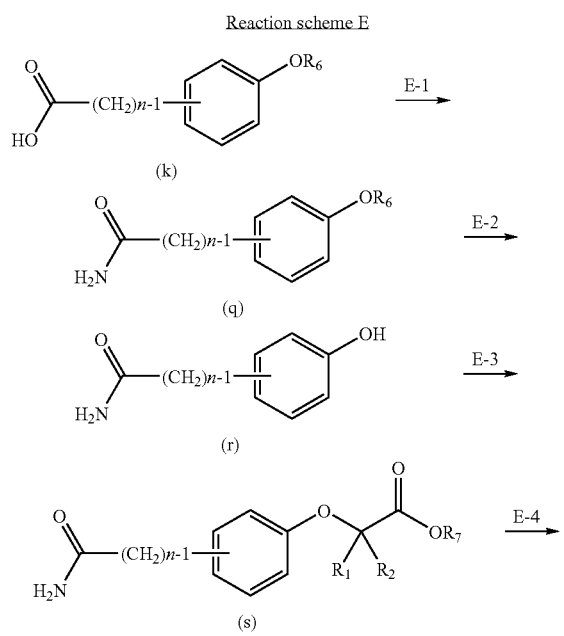

Reaction scheme E

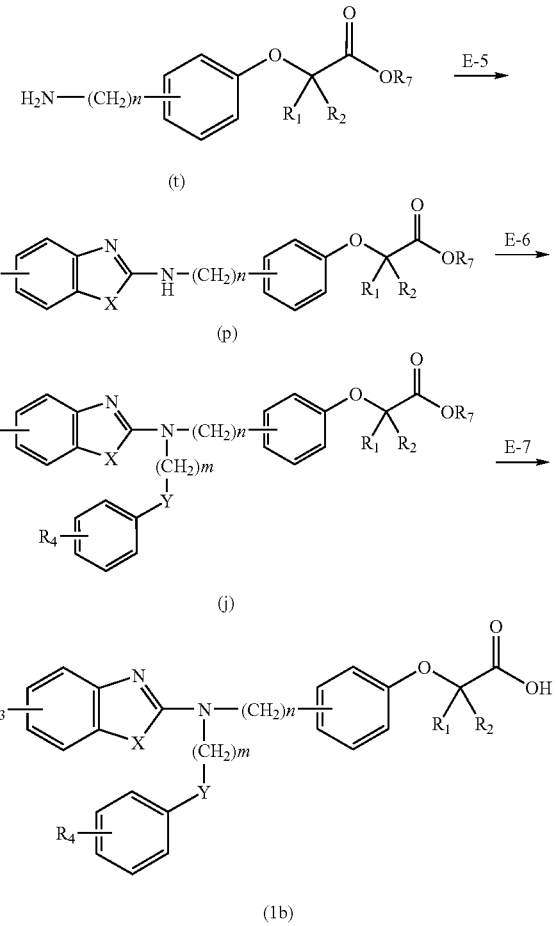

The production method represented by reaction scheme E includes the following steps: The starting carboxylic acid (k) is reacted with ammonia or an ammonium salt, to thereby produce an amide compound (q); the hydroxyl-protective group is removed from the amide compound (q), to thereby produce a phenol compound (r); the pnenol copmpound (r) is reacted with 2-haloalkylcarboxylic acid ester, to thereby produce an amide compound (S); the amide compound (s) is reduced to thereby produce an amino compound (t); the amino compound (t) is reacted with 2-halo-1,3-benzoazole, to thereby produce an amino compound (p); the amino compound (p) is reacted with a halide, to thereby produce an amino compound (j); and the amino compound (j) is subjected to hydrolysis, whereby the compound (1b) of the present invention is obtained.

The first step (E-1) proceeds as follows. The starting carboxylic acid (k) is dissolved in a solvent such as N,N-dimethylformamide (DMF), tetrahydrofuran (THF), dioxane, acetonitrile, or a mixture of solvents suitably selected therefrom. An inorganic base such as potassium carbonate (K$_2$CO$_3$), sodium carbonate (Na$_2$CO$_3$), or cesium carbonate (Cs$_2$CO$_3$) or an organic base such as triethylamine, diisopropylethylamine, or pyridine is added thereto. An anhydride such as ditert-butyl dicarbonate is added to the mixture, followed by stirring for several minutes to 3 hours under cooling or at room temperature. Ammonia or an ammonium salt (e.g., ammonium hydrogencarbonate) is added thereto. The resultant mixture is stirred for several hours to 24 hours under cooling or at room temperature.

The second step (E-2) proceeds as follows. The amide compound (q) prepared in the first step is dissolved in a solvent such as dichloromethane, chloroform, or chlorobenzene, as needed. Thereafter, a Lewis acid such as boron tribromide or aluminum chloride is added thereto, and the mixture is stirred under cooling or at around the boiling point of the solvent for several hours to 24 hours. If $R_6$=H, the reaction in the second step is not required.

The third step (E-3) proceeds as follows. The phenol compound (r) is dissolved in a solvent such as DMF, THF, dioxane, or acetonitrile. A necessary amount of an inorganic base such as $K_2CO_3$, $Na_2CO_3$, or $Cs_2CO_3$ or an organic base such as triethylamine or diisopropylethylamine is added thereto. Subsequently, a necessary amount of a 2-haloalkylcarboxylic acid ester such as 2-bromoisobutyric acid ester, 2-bromo-n-butyric acid ester, or 2-bromopropionic acid ester is added, and the resultant mixture is allowed to react at a temperature between room temperature and around the boiling point of the solvent under stirring for several hours to 24 hours. The ester is appropriately selected from among tert-butyl esters, ethyl esters, methyl esters, etc.

The fourth step (E-4) proceeds as follows. The starting amide compound (s) is dissolved in a solvent such as THF or dioxane. Subsequently, if necessary, in an inert gas atmosphere, a necessary amount of a reducing agent such as borane tetrahydrofuran complex ($BH_3$.THF) is added thereto, and the reaction mixture is stirred at room temperature or under heating for several hours to 24 hours.

The fifth step (E-5) proceeds as follows. The starting amino compound (t) is dissolved in a solvent such as DMF, THF, dioxane, or acetonitrile. 2-Halo-1,3-benzoazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is allowed to react at a temperature between room temperature and around the boiling point of the solvent under stirring for several hours to 24 hours (in an inert gas atmosphere, if necessary).

The sixth step (E-6) proceeds as follows. The starting amino compound (p) is dissolved in an inert solvent such as DMF, THF, dioxane, or acetonitrile. A suitably selected halide is added thereto in the presence of a necessary amount of an inorganic base such as $K_2CO_3$, $Na_2CO_3$, or $Cs_2CO_3$ or an organic base such as triethylamine or diisopropylethylamine. The mixture is allowed to react at a temperature between room temperature and around the boiling point of the solvent under stirring for several hours to 24 hours.

The seventh step (E-7) proceeds as follows. In the case where a methyl ester, ethyl ester, or any ester that is easily hydrolyzed with an alkali is used as the starting compound, the ester is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling, or between room temperature and around the boiling point of the solvent. After completion of reaction, the reaction mixture is acidified by use of an acid such as hydrochloric acid. On the other hand, in the case where a tert-butyl ester or any ester that is easily decomposed by an acid is used as the starting compound, the ester is dissolved in a solvent such as dichloromethane or chloroform, followed by addition of an acid such as trifluoroacetic acid, and the resultant mixture is stirred for several hours to 24 hours under cooling or at room temperature.

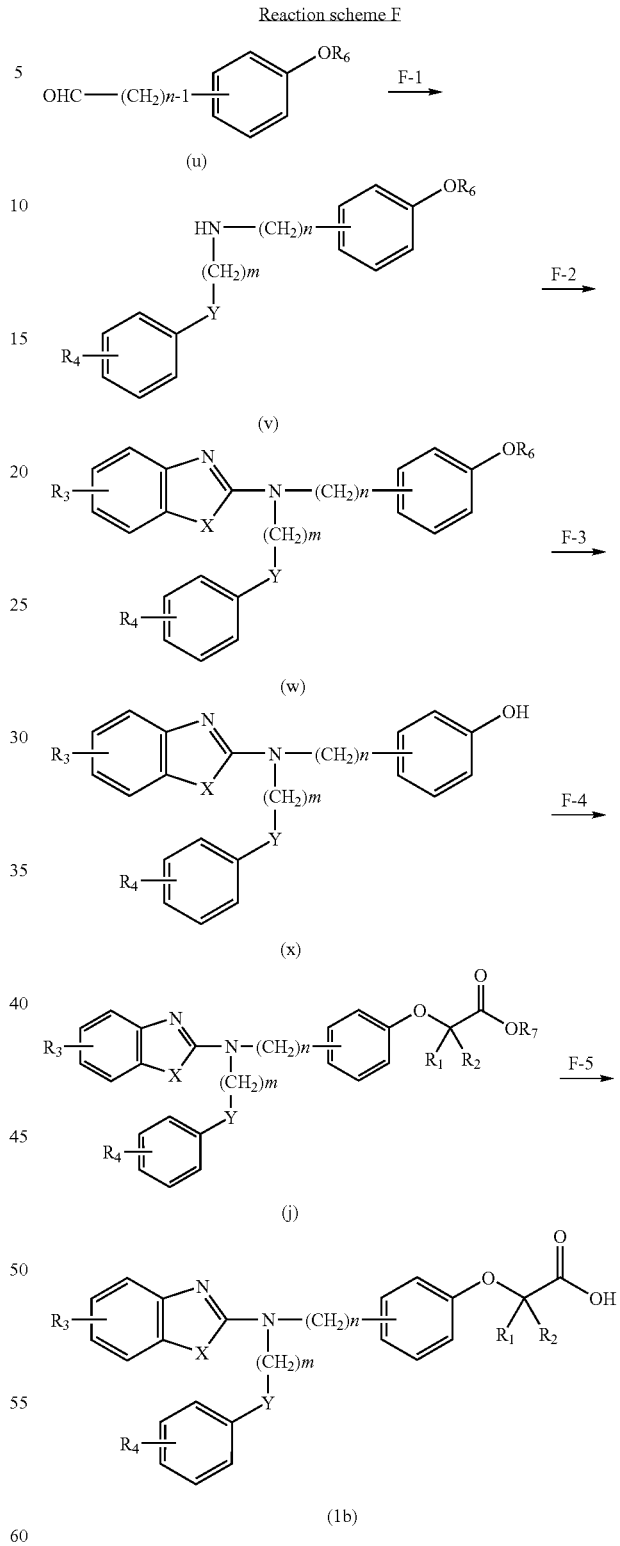

The production method represented by reaction scheme F includes the following steps: The starting aldehyde compound (u) is reacted with an amine compound, followed by reduction; the thus-obtained amino compound (v) is reacted with 2-halo-1,3-benzoazole, to thereby produce the compound (w); the hydroxyl-protective group is removed from the compound (w), to thereby produce a phenol compound (x); the phenol compound is reacted with 2-hydroxycarboxylic acid ester, to thereby produce a compound (j); and the compound (j) is subjected to hydrolysis, to thereby produce the compound (1b) of the present invention.

The first step (F-1) proceeds as follows. The starting aldehyde compound (u) is dissolved in a solvent such as 1,2-dichloroethane, chloroform, dichloromethane, N,N-dimethylformamide (DMF), tetrahydrofuran (THF), dioxane, or acetonitrile. Subsequently, a suitably selected amine compound and an acid such as acetic acid are added, followed by reduction with a reducing agent such as sodium triacetoxyborohydride ($NaBH(OAc)_3$). The reaction is carried out by stirring the mixture under cooling or at room temperature for several hours to 24 hours (in an inert gas atmosphere, if necessary).

The second step (F-2) proceeds as follows. The amino compound (v) prepared in the first step is dissolved in a solvent such as DMF, THF, dioxane, or acetonitrile. 2-Halo-1,3-benzoazole such as 2-chlorobenzoxazole is added thereto in the presence of a necessary amount of an inorganic base such as $K_2CO_3$, $Na_2CO_3$, or $Cs_2CO_3$ or an organic base such as triethylamine or diisopropylethylamine. The mixture is allowed to react at a temperature between room temperature and around the boiling point of the solvent under stirring for several hours to 24 hours (in an inert gas atmosphere, if necessary).

The third step (F-3) proceeds as follows. In the case where an ester that is easily hydrolyzed with an alkali such as an acetyl group is used as the starting compound the ester is dissolved in a solvent such as methanol, ethanol, or THF; a base such as lithium hydroxide, sodium hydroxide, potassium hydroxide, or potassium carbonate or an aqueous solution thereof is added thereto; and the mixture is allowed to react for several hours to 24 hours under cooling or at a temperature between room temperature and around the boiling point of the solvent. After completion of reaction, the reaction mixture is neutralized or acidified by use of an acid such as an aqueous ammonium chloride solution or diluted hydrochloric acid. In the case where the ester is easily decomposed by an acid, as in the case of an ester having a methoxymethyl moiety, the ester is dissolved in a solvent such as dichloromethane or chloroform, and an acid such as hydrochloric acid is added to the solution, followed by stirring the mixture for several hours to 24 hours under cooling or at room temperature. In the case of a silyl group such as tert-butyldimethylsilyl, the silyl group is dissolved in a solvent such as THF, dioxane, acetonitrile, dichloromethane, or chloroform, and a fluoride compound such as tetrabutylammonium fluoride is added to the solution, followed by stirring the mixture for several hours to 24 hours at a temperature between room temperature and around the boiling temperature of the solvent. In this case, the reaction may be performed by dissolving the the silyl group in a solvent such as DMF, ethanol, or methanol, adding a base such as potassium carbonate, cesium carbonate, or lithium hydroxide to the solution, and stirring the mixture for several hours to 24 hours at a temperature between room temperature and around the boiling point of the solvent.

The fourth step (F-4) proceeds as follows. The phenol compound (x) obtained in the third step and a 2-hydroxycarboxylic acid ester such as tert-butyl 2-hydroxybutyrate or ethyl lactate are dissolved in a solvent such as THF, dioxane, acetonitrile, or toluene. Under the Mitsunobu reaction conditions, the solution is stirred at a temperature between room temperature and around the boiling point of the solvent for several hours to 24 hours. Alternatively, a 2-hydroxycarboxylic acid ester such as tert-butyl 2-hydroxybutyrate or ethyl lactate is dissolved in a solvent such as THF, dioxane, acetonitrile, toluene, or DMF. Subsequently, an inorganic base or an organic base such as triethylamine or diisopropylethylamine is added thereto. Subsequently, sulfonyl chloride such as methanesulfonyl chloride or p-toluenesulfonyl chloride is added thereto. The resultant mixture and the phenol compound (x) produced in the third step are mixed together, and the resultant mixture is stirred for several hours to 24 hours under ice-cooling or at a temperature between room temperature and around the boiling point of the solvent. The ester is appropriately selected from among tert-butyl esters, ethyl esters, methyl esters, etc.

The fifth step (F-5) proceeds as follows. In the case where a methyl ester, ethyl ester, or any ester that is easily hydrolyzed with an alkali is used as the starting compound, the ester is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling or at a temperature between room temperature and around the boiling point of the solvent. After completion of reaction, the reaction mixture is acidified by use of an acid such as hydrochloric acid. On the other hand, in the case where a tert-butyl ester or any ester that is easily decomposed by an acid is used as the starting compound, the ester is dissolved in a solvent such as dichloromethane or chloroform, followed by addition of an acid such as trifluoroacetic acid, and the resultant mixture is stirred for several hours to 24 hours under cooling or at room temperature.

This synthesis route enables a successful synthesis of compounds (1b), even when $R_6$ is a hydrogen atom. In this case ($R_6$=H), the process in the third step F-3 is not required.

Reaction scheme G

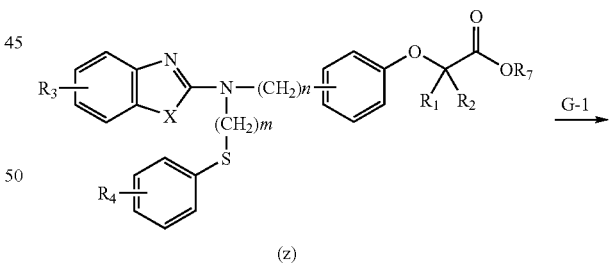

(z)

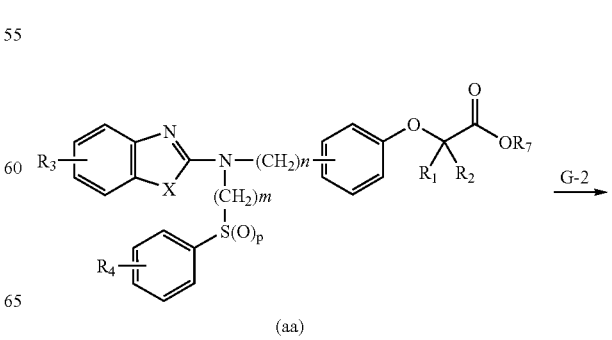

(aa)

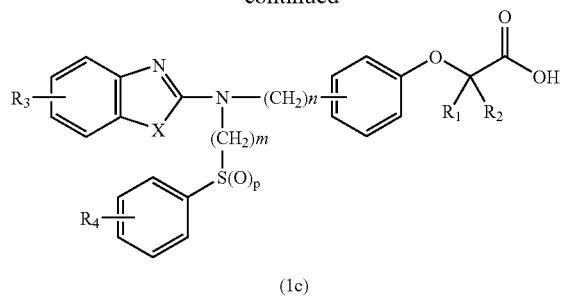

(1c)

(X = O, N—R5)

The production method represented by reaction scheme G includes the following steps: The compound (z) obtained in the course of reaction scheme A is oxidized; and the oxidized compound is subjected to hydrolysis, to thereby produce the compound (1c) of the present invention.

The first step (G-1) proceeds as follows. The compound (z) produced in the fourth step of reaction scheme A is dissolved in a solvent such as chloroform or dichloromethane. Subsequently, the compound (z) is oxidized by use of an peroxide such as m-chloroperoxybenzoic acid or $H_2O_2$ under stirring for several hours to 24 hours under cooling or at room temperature.

The second step (G-2) proceeds as follows. In the case of a methyl ester, an ethyl ester, or any ester that is easily hydrolyzed with an alkali, the ester compound is dissolved in a solvent such as methanol, ethanol, or THF; a base such as lithium hydroxide, sodium hydroxide, or potassium hydroxide, or an aqueous solution thereof is added thereto; and the mixture is allowed to react for several hours to 24 hours under cooling or at a temperature between room temperature and around the boiling point of the solvent. After completion of reaction, the reaction mixture is acidified by use of an acid such as hydrochloric acid. In the case of a tert-butyl ester or any ester that is easily decomposed by an acid, the ester compound is dissolved in a solvent such as dichloromethane or chloroform, and an acid such as trifluoroacetic acid is added to the solution, followed by stirring the mixture for several hours to 24 hours under cooling or at room temperature.

The compounds according to the present invention can be produced through any of the aforementioned methods. The thus-obtained products may be purified in accordance with needs through a customary purification method such as recrystallization or column chromatography. The compounds may be converted to the aforementioned desired salts or solvates through a routine process, in accordance with needs.

As described in relation to the below-mentioned Test Example, the thus-produced compounds of the present invention exert a selective activation effect on PPARα. Thus, these compounds are useful as a drug for preventing and/or treating pathological conditions of mammals (including humans) such as hyperlipidemia, arteriosclerosis, diabetes, complications of diabetes (e.g., diabetic nephropathy), inflammation, and heart diseases, without causing increase in body weight or obesity.

The pharmaceutical of the present invention contains, as an active ingredient, the present compound (1) or a salt thereof. No particular limitation is imposed on the form of administration, and the administration form can be appropriately determined in accordance with the purpose of treatment, and selected from among, for examples, peroral solid forms, peroral liquid forms, injections, suppositories, external preparations, ophthalmic solutions, nasal drops, ear drops, and patches. These administration forms can be produced by mixing the active ingredient with a pharmacologically acceptable carrier and through any preparation methods known in the art.

When an oral solid drug product is prepared, the present compound (1) is mixed with a diluent (and, if necessary, an additive such as a binder, a disintegrant, a lubricant, a coloring agent, a sweetening agent, or a flavoring agent), and the resultant mixture is processed through a routine method, to thereby produce an oral solid drug product such as tablets, granules, powder, or capsules. Such an additive may be an additive generally employed in the art. Examples of the diluent include lactose, sodium chloride, glucose, starch, microcrystalline cellulose, and silicic acid; examples of the binder include water, ethanol, propanol, simple syrup, liquefied gelatin, hydroxypropyl cellulose, methyl cellulose, ethyl cellulose, shellac, calcium phosphate, and polyvinyl pyrrolidone; examples of the disintegrant include agar powder, sodium hydrogencarbonate, sodium lauryl sulfate, and monoglyceryl stearate; examples of the lubricant include purified talc, stearate salt, borax, and polyethylene glycol; examples of the coloring agent include β-carotene, yellow iron sesquioxide, and caramel; and examples of the sweetening agent include saccharose and orange peel.

When a liquid drug product for oral administration is prepared, the present compound (1) is mixed with an additive such as a sweetening agent, a buffer, a stabilizer, or a preservative, and the resultant mixture is processed through a routine method, to thereby produce an orally administered liquid drug product such as internal solution medicine, syrup, or elixir. Such an additive may be an additive generally employed in the art. Examples of the sweetening agent include saccharose; examples of the buffer include sodium citrate; examples of the stabilizer include tragacanth; and examples of the preservative include p-hydroxybenzoate ester.

When an injection is prepared, the present compound (1) is mixed with an additive such as a pH regulator, a stabilizer, or an isotonicity agent, and the resultant mixture is processed through a routine method, to thereby produce an injection such as a subcutaneous injection, an intramuscular injection, or an intraveneous injection. Such an additive may be an additive generally employed in the art. Examples of the pH regulator include sodium phosphate; examples of the stabilizer include sodium pyrosulfite; and examples of the isotonicity agent include sodium chloride.

When a suppository is prepared, the present compound (1) is mixed with an additive such as a carrier or a surfactant, and the resultant mixture is processed through a routine method, to thereby produce a suppository. Such an additive may be an additive generally employed in the art. Examples of the carrier include polyethylene glycol and hard fat, and examples of the surfactant include polysorbate 80.

When an external drug product is prepared, the present compound (1) is mixed with an additive such as a base, a water-soluble polymer, a solvent, a surfactant, or a preservative, and the resultant mixture is processed through a routine method, to thereby produce external preparations such as liquids or solutions, creams, gels, or ointments.

Examples of the base include liquid paraffin, white Vaseline, and purified lanolin; examples of the water-soluble polymer include carboxyvinyl polymer; examples of the solvent include glycerol and water; examples of the surfactant include polyoxyethylene fatty acid ester; and examples of the preservative include p-hydroxybenzoate ester.

When an ophthalmic solution is prepared, the present compound (1) is mixed with an additive such as a pH regulator, a stabilizer, an isotonicity agent, or a preservative, and the resultant mixture is processed through a routine method, to thereby produce an ophthalmic solution. Such an additive may be an additive generally employed in the art. Examples of the pH regulator include sodium phosphate; examples of the stabilizer include sodium pyrosulfite and EDTA; examples of the isotonicity agent include sodium chloride; and examples of the preservative include chlorobutanol.

When a nasal drop is prepared, the present compound (1) is mixed with an additive such as a pH regulator, a stabilizer, an isotonicity agent, or a preservative, and the resultant mixture is processed through a routine method, to thereby produce a nasal drop. Such an additive may be an additive generally employed in the art. Examples of the pH regulator include sodium phosphate; examples of the stabilizer include sodium pyrosulfite and EDTA; examples of the isotonicity agent include sodium chloride; and examples of the preservative include benzalkonium chloride.

When an ear drop is prepared, the present compound (1) is mixed with an additive such as a pH regulator, a buffer, a stabilizer, an isotonicity agent, or a preservative, and the resultant mixture is processed through a routine method, to thereby produce an ear drop. Such an additive may be an additive generally employed in the art. Examples of the pH regulator and the buffer include sodium phosphate; examples of the stabilizer include sodium pyrosulfite and EDTA; examples of the isotonicity agent include sodium chloride; and examples of the preservative include benzalkonium chloride.

When a patch is prepared, the present compound (1) is mixed with an additive such as a tackifier, a solvent, a cross linking agent, or a surfactant, and the resultant mixture is processed through a routine method, to thereby produce a patch such as a hydrated patch or plaster patch. Such an additive may be an additive generally employed in the art. Examples of the tackifier include partially neutralized poly(acrylic acid), sodium polyacrylate, poly(2-ethylhexylacrylate), and styrene-isoprene-styrene block copolymer; examples of the solvent include glycerol and water; examples of the cross linking agent include dihydroxyaluminum aminoacetate and dried aluminum hydroxide gel; and examples of the surfactant include polyoxyethylene fatty acid ester.

The dose of the drug of the present invention differs depending on the age, body weight, and condition of the patient and the manner and frequency of administration, etc. The daily dose of the present compound (1) for an adult is typically 1 to 1,000 mg, and the drug is preferably administered perorally or parenterally once a day or several times a day in a divided manner.

EXAMPLES

The present invention will next be described in detail by way of examples, which should not be construed as limiting the invention.

Production Example 1

Synthesis of Ethyl 2-(3-formylphenoxy)butyrate

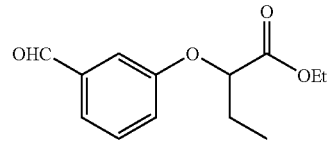

3-Hydroxybenzaldehyde (18.3 g, 0.150 mol) was dissolved in N,N-dimethylformamide (150 mL). Subsequently, potassium carbonate (22.80 g, 0.165 mol), and then ethyl 2-bromobutyrate (29.26 g, 0.150 mol) were added thereto, and the resultant mixture was stirred overnight at 80° C. The temperature of the reaction mixture was returned to room temperature. Ethyl acetate was added. Washing was performed sequentially with water and brine, followed by drying over sodium sulfate. The reaction mixture was subjected to filtration, concentration under reduced pressure, and purification by silica gel column chromatography (n-hexane/ethyl acetate=5/1), whereby a colorless oil was obtained (35.29 g, 0.149 mol, 99.6%).

$^1$H-NMR (400 MHz, CDCl$_3$) δ: 1.10 (t, J=7 Hz, 3H), 1.26 (t, J=7 Hz, 3H), 1.99–2.06 (m, 2H), 4.23 (q, J=7 Hz, 2H), 4.65 (t, J=6 Hz, 1H), 7.17–7.22 (m, 1H), 7.35 (s, 1H), 7.45–7.49 (m, 2H), 9.95 (s, 1H.

Production Example 2

Synthesis of Ethyl 2-[3-[N-[3-(4-fluorophenoxy)propyl]aminomethyl]phenoxy]butyrate

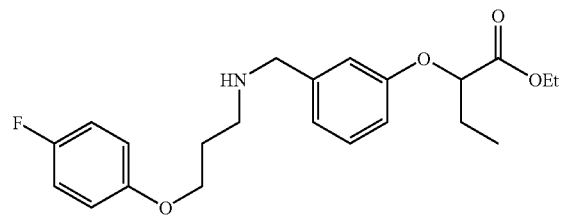

Ethyl 2-(3-formylphenoxy)butyrate (5.0 g, 21.2 mmol) was dissolved in 1,2-dichloroethane (20 mL). Subsequently, 3-(4-fluorophenoxy)propylamine (4.65 g, 27.5 mmol) was added thereto, and the resultant mixture was stirred for 20 minutes. Subsequently, sodium triacetoxyborohydride (95%, 7.1 g, 31.8 mmol) and small amount of acetic acid were added thereto, and the mixture was stirred overnight at room temperature. A saturated aqueous sodium hydrogencarbonate solution was added thereto. The reaction mixture was extracted with chloroform, and the organic layer was washed with brine. The resultant mixture was subjected to drying over anhydrous sodium sulfate, concentration under reduced pressure, and purification by silica gel chromatography (chloroform/methanol=30/1), whereby the target compound was obtained (6.7 g, 81%).

$^1$H-NMR (400 MHz, CDCl$_3$) δ 1.07 (t, J=7 Hz, 3H), 1.24 (t, J=7 Hz, 3H), 1.93–2.01 (m, 4H), 2.80 (t, J=7 Hz, 2H), 3.77 (s, 2H), 4.00 (t, J=6 Hz, 2H), 4.21 (q, J=7 Hz, 2H), 4.55 (t, J=6 Hz, 1H), 6.74–6.84 (m, 3H), 6.89–6.98 (m, 4H), 7.21 (t, J=8 Hz, 1H).

Production Example 3

Synthesis of Ethyl 2-[3-[[N-(benzoxazol-2-yl)-N-3-(4-fluorophenoxy)propyl]aminomethyl]phenoxy]butyrate

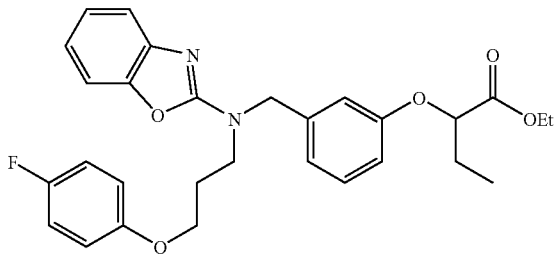

Ethyl 2-[3-[N-[3-(4-fluorophenoxy)propyl]aminomethyl]phenoxy]butyrate (6.2 g, 15.9 mmol) was dissolved in N,N-dimethylformamide (10 mL), and N,N-diisopropylethylamine (3.1 g, 23.8 mmol) was added dropwise thereto. Subsequently, 2-chlorobenzoxazole (2.9 g, 19.0 mmol) was added thereto, and the resultant mixture was stirred for 15 minutes at room temperature, followed by stirring overnight at 50° C. Subsequently, a saturated aqueous sodium hydrogencarbonate solution was added thereto. The reaction mixture was extracted with ethyl acetate, and the organic layer was washed with brine. The resultant mixture was subjected to drying over anhydrous sodium sulfate, concentration under reduced pressure, and purification by silica gel chromatography (n-hexane/ethyl acetate=4/1), whereby the target compound was obtained (7.5 g, 93%).

$^1$H-NMR (400 MHz, CDCl$_3$) δ 1.05 (t, J=7 Hz, 3H), 1.17 (t, J=7 Hz, 3H), 1.96 (quintet, J=7 Hz, 2H), 2.14 (quintet, J=6 Hz, 2H), 3.70 (t, J=7 Hz, 2H), 4.00 (t, J=6 Hz, 2H), 4.12 (q, J=7 Hz, 2H), 4.51 (t, J=6 Hz, 1H), 4.72 (d, J=16 Hz, 1H), 4.77 (d, J=16 Hz, 1H), 6.75–6.81 (m, 3H), 6.86–7.00 (m, 4H), 7.01 (t, J=8 Hz, 1H), 7.17 (t, J=8 Hz, 1H), 7.19–7.23 (m, 2H), 7.36 (d, J=7 Hz, 1H).

Example 1

Synthesis of 2-[3-[[N-(Benzoxazol-2-yl)-N-3-(4-fluorophenoxy)propyl]aminomethyl]phenoxy]butyric acid

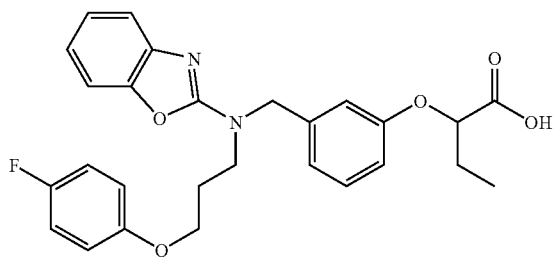

Ethyl 2-[3-[[N-(benzoxazol-2-yl)-N-3-(4-fluorophenoxy)propyl]aminomethyl]phenoxy]butyrate (7.3 g, 14.4 mmol) was dissolved in a methanol-tetrahydrofuran mixed solvent (25 mL), and an aqueous solution of 2 mol/L sodium hydroxide (21.6 mL, 43.2 mmol) was added dropwise thereto. The resultant mixture was stirred for 2 hours at 60° C. and subjected to concentration under reduced pressure. A saturated aqueous sodium hydrogencarbonate solution was added thereto. Subsequently, the reaction mixture was extracted with ethyl acetate, and the organic layer was washed with brine. The resultant mixture was subjected to drying over anhydrous sodium sulfate, concentration under reduced pressure, and purification by silica gel chromatography (chloroform/methanol=60/1), whereby the target compound was obtained (6.7 g, q.).

$^1$H-NMR (400 MHz, CDCl$_3$) δ 1.04 (t, J=7 Hz, 3H), 1.95 (quintet, J=7 Hz, 2H), 2.04 (quintet, J=6 Hz, 2H), 3.56–3.64 (m, 2H), 3.87 (t, J=6 Hz, 2H), 4.50 (t, J=6 Hz, 1H), 4.62 (d, J=16 Hz, 1H), 4.68 (d, J=16 Hz, 1H), 6.73–6.93 (m, 7H), 6.99 (t, J=8 Hz, 1H), 7.10–7.20 (m, 3H), 7.34 (d, J=8 Hz, 1H).

In a manner similar to that described in Example 1, the compounds of Examples 2 through Example 30 were synthesized.

Example 2

Synthesis of 2-[3-[[N-(Benzoxazol-2-yl)-N-2-(4-chlorophenoxy)ethyl]aminomethyl]phenoxy]butyric acid

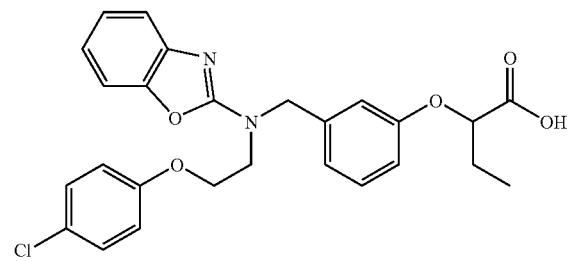

$^1$H-NMR (400 MHz, CDCl$_3$) δ 1.09 (t, J=7 Hz, 3H), 2.00 (quintet, J=7 Hz, 2H), 3.81 (m, 2H), 4.13 (t, J=5 Hz, 2H), 4.57 (t, J=7 Hz, 1H), 4.84 (d, J=6 Hz, 2H), 6.73 (d, J=9 Hz, 2H), 6.86 (d, J=8 Hz, 1H), 6.87 (s, 1H), 6.92 (d, J=8 Hz, 1H), 7.02 (t, J=8 Hz, 1H), 7.13–7.25 (m, 5H), 7.36 (d, J=8 Hz, 1H).

Example 3

Synthesis of 2-[3-[[N-(Benzoxazol-2-yl)-N-2-(4-fluorophenoxy)ethyl]aminomethyl]phenoxy]butyric acid

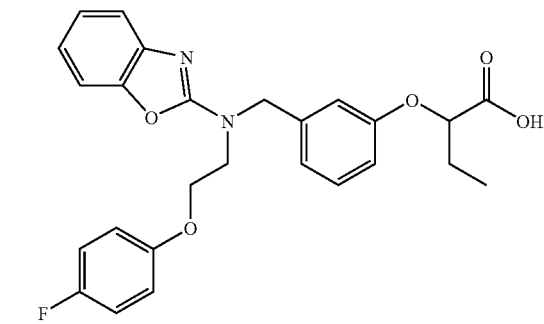

$^1$H NMR (270 MHz, CDCl$_3$) δ 1.08 (t, J=8 Hz, 3H), 2.01 (quintet, J=7 Hz, 2H), 3.78 (m, 2H), 4.08 (t, J=5 Hz, 2H), 4.56 (t, J=7 Hz, 1H), 4.81 (d, J=16 Hz, 1H), 4.88 (d, J=16 Hz, 1H), 6.69–6.78 (m, 2H), 6.82–6.96 (m, 5H), 7.03 (t, J=8 Hz, 1H), 7.12–7.29 (m, 3H), 7.36 (d, J=8 Hz, 1H).

Example 4

Synthesis of 2-[3-[[N-(Benzoxazol-2-yl)-N-2-(4-methoxyphenoxy)ethyl]aminomethyl]phenoxy]butyric acid

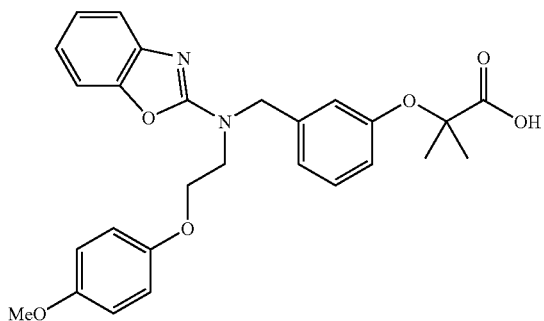

¹H-NMR (400 MHz, CDCl₃) δ 1.59 (s, 6H), 3.74 (s, 3H), 3.78 (t, J=5 Hz, 2H), 4.09 (t, J=5 Hz, 2H), 4.84 (s, 2H), 6.71–6.81 (m, 4H), 6.81–7.05 (m, 5H), 7.10–7.25 (m, 2H), 7.35 (d, J=8 Hz, 1H).

Example 5

Synthesis of 2-[3-[[N-(Benzoxazol-2-yl)-N-3-(4-fluorophenoxy)propyl]aminomethyl]phenoxy]-2-methylpropionic acid

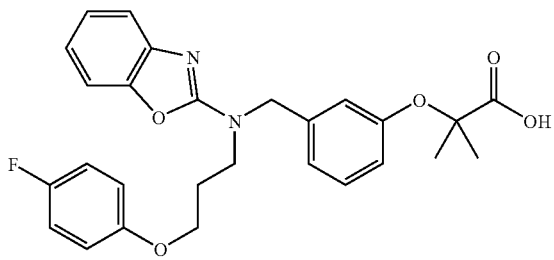

¹H-NMR (400 MHz, CDCl₃) δ 1.56 (s, 6H), 2.04 (quintet, J=7 Hz, 2H), 3.59 (t, J=7 Hz, 2H), 3.88 (t, J=6 Hz, 2H), 4.64 (s, 2H), 6.74–6.94 (m, 7H), 6.99 (t, J=8 Hz, 1H), 7.11–7.19 (m, 3H), 7.36 (d, J=7 Hz, 1H).

Example 6

Synthesis of 2-[3-[[N-(Benzoxazol-2-yl)-N-2-(4-chlorophenoxy)ethyl]aminomethyl]phenoxy]-2-methylpropionic acid

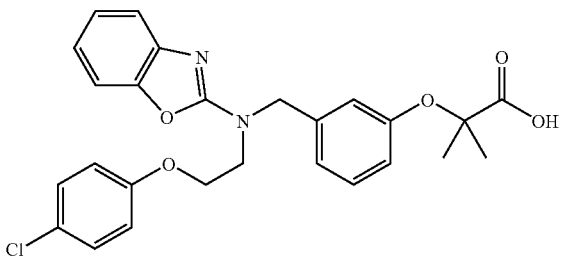

¹H-NMR (400 MHz, CDCl₃) δ 1.56 (s, 6H), 3.81 (t, J=5 Hz, 2H), 4.13 (t, J=5 Hz, 2H), 4.83 (s, 2H), 6.74 (d, J=9 Hz, 2H), 6.85 (d, J=8 Hz, 1H), 6.89 (s, 1H), 6.96 (d, J=8 Hz, 1H), 7.02 (t, J=8 Hz, 1H), 7.13–7.25 (m, 5H), 7.36 (d, J=7 Hz, 1H).

Example 7

Synthesis of 2-[4-[[N-(Benzoxazol-2-yl)-N-2-(3-dimethylaminophenoxy)ethyl]aminomethyl]phenoxy]-2-methylpropionic acid

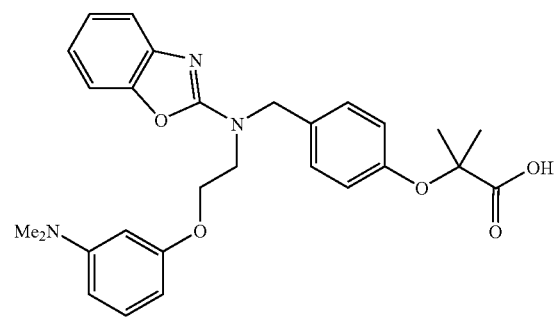

¹H NMR (400 MHz, CDCl₃) δ 1.58 (s, 6H), 3.11 (s, 6H), 3.96 (m, 2H), 4.11 (m, 2H), 4.86 (s, 2H), 6.71–6.85 (m, 4H), 6.98 (d, J=8 Hz, 1H), 7.09–7.37 (m, 6H), 7.49 (d, J=8 Hz, 1H).

Example 8

Synthesis of 2-[3-[[N-(Benzoxazol-2-yl)-N-3-(4-methanesulfonyloxyphenoxy)propyl]aminomethyl]phenoxy]-2-methylpropionic acid

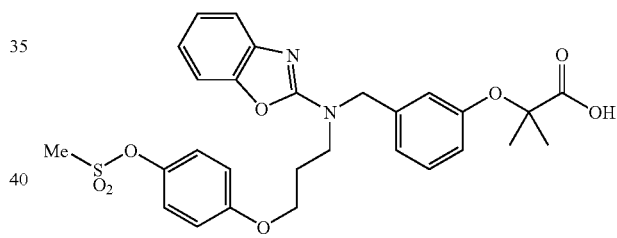

¹H-NMR (400 MHz, CDCl₃) δ 1.53 (s, 6H), 2.12 (br s, 2H), 3.09 (s, 3H), 3.74 (t, J=7 Hz, 2H), 3.97 (t, J=6 Hz, 2H), 4.74 (s, 2H), 6.80–6.91 (m, 5H), 7.11–7.26 (m, 6H), 7.44 (d, J=7 Hz, 1H).

Example 9

Synthesis of 2-[3-[[N-(Benzoxazol-2-yl)-N-3-phenoxypropyl]aminomethyl]phenoxy]propionic acid

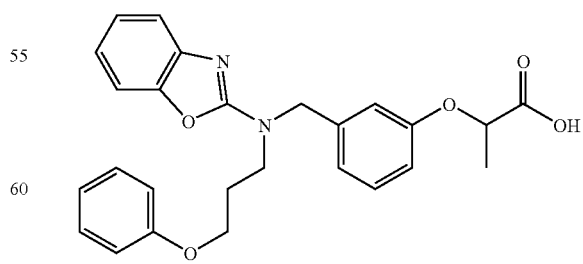

¹H NMR (400 MHz, CDCl₃) δ 1.61 (d, J=7 Hz, 3H), 2.06 (quintet, J=6 Hz, 2H), 3.61 (m, 2H), 3.92 (t, J=6 Hz, 2H), 4.60–4.73 (m, 3H), 6.80–6.95 (m, 6H), 7.00 (t, J=7 Hz, 1H), 7.10–7.26 (m, 5H), 7.36 (d, J=7 Hz, 1H).

Example 10

Synthesis of 2-[4-[[N-(Benzoxazol-2-yl)-N-3-(4-methanesulfonyloxyphenoxy)propyl]aminomethyl]phenoxy]-2-methylpropionic acid

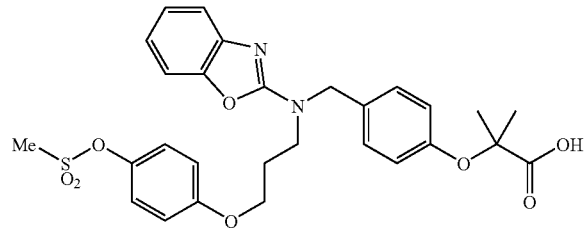

$^1$H-NMR (400 MHz, CDCl$_3$) δ 1.58 (s, 6H), 2.15 (br s, 2H), 3.09 (s, 3H), 3.80 (t, J=7 Hz, 2H), 4.00 (t, J=6 Hz, 2H), 4.79 (s, 2H), 6.83 (d, J=9 Hz, 2H), 6.89 (d, J=9 Hz, 2H), 7.16 (d, J=9 Hz, 2H), 7.19 (d, J=9 Hz, 2H), 7.21–7.29 (m, 2H), 7.31 (t, J=8 Hz, 1H), 7.54 (d, J=8 Hz, 1H), 11.40 (br s, 1H).

Sodium 2-[4-[[N-(benzoxazol-2-yl)-N-3-(4-methanesulfonyloxyphenoxy)propyl]aminomethyl]phenoxy]-2-methylpropionate

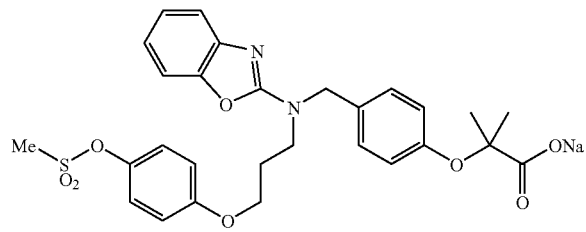

2-[4-[[N-(Benzoxazol-2-yl)-N-3-(4-methanesulfonyloxyphenoxy)propyl]aminomethyl]phenoxy]-2-methylpropionic acid (5.96 g, 10.7 mmol) was dissolved in methanol. A solution of NaOMe (580 mg, 10.7 mmol) in methanol was added thereto at room temperature, and then the resultant mixture was stirred for 1 hour. Subsequently, the reaction mixture was subjected to concentration under reduced pressure, and n-hexane was added to the resultant concentrate. The thus-obtained solid was purified, whereby a white amorphous powder was obtained (5.2 g, 84%).

$^1$H-NMR (400 MHz, CDCl$_3$) δ 1.61 (s, 6H), 2.03 (br s, 2H), 3.08 (s, 3H), 3.56 (br s 2H), 3.88 (br s, 2H), 4.64 (s, 2H), 6.81–6.83 (m, 4H), 7.01 (t, J=7 Hz, 1H), 7.08 (d, J=8 Hz, 2H), 7.14–1.18 (m, 4H), 7.46 (d, J=8 Hz, 1H).

Example 11

Synthesis of 2-[3-[[N-(Benzoxazol-2-yl)-N-3-phenoxypropyl]aminomethyl]phenoxy]-2-methylpropionic acid

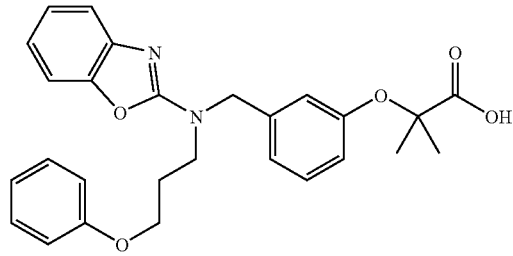

MS (m/z) 460 (M$^+$).

Sodium 2-[3-[[N-(benzoxazol-2-yl)-N-3-phenoxypropyl]aminomethyl]phenoxy]-2-methylpropionate

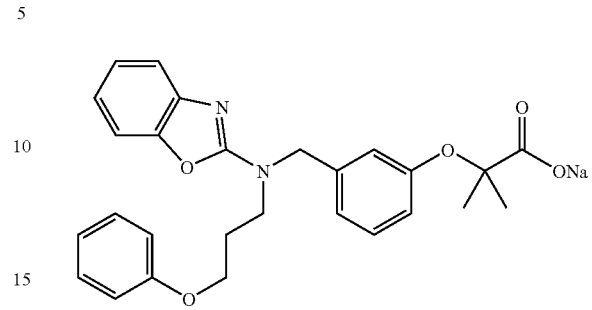

$^1$H-NMR (400 MHz, CDCl$_3$) δ 1.36 (s, 6H), 2.80 (quintet, J=7 Hz, 2H), 3.64 (t, J=7 Hz, 2H), 3.94 (t, J=6 Hz, 2H), 4.62 (s, 2H), 6.73 (d, J=8 Hz, 1H), 6.82–6.86 (m, 4H), 6.89–6.96 (m, 2H), 7.04–7.15 (m, 3H), 7.21–7.26 (m, 2H), 7.30 (d, J=8 Hz, 1H).

Example 12

Synthesis of 3-[[N-(Benzoxazol-2-yl)-N-3-phenoxypropyl]aminomethyl]phenoxyacetic acid

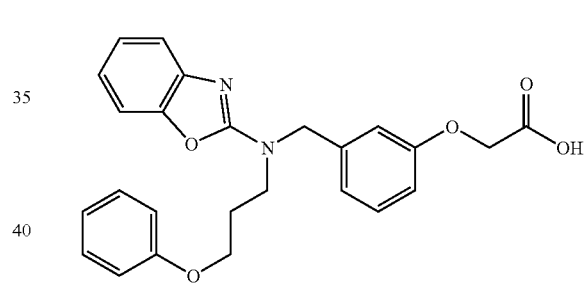

MS (m/z) 432 (M$^+$).

Sodium 3-[[N-(benzoxazol-2-yl)-N-3-phenoxypropyl]aminomethyl]phenoxyacetate

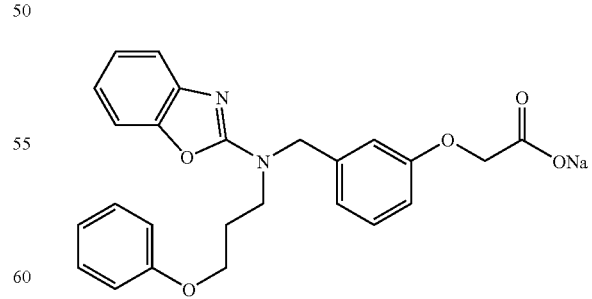

$^1$H-NMR (400 MHz, CD$_3$OD) δ 2.09 (quintet, J=7 Hz, 2H), 3.69 (t, J=7 Hz, 2H), 3.97 (t, J=6 Hz, 2H), 4.52 (s, 2H), 4.74 (s, 2H), 6.83–6.91 (m, 6H), 6.99 (td, J=8, 1 Hz, 1H), 7.13 (td, J=8, 1 Hz, 1H), 7.18–7.27 (m, 5H).

Example 13

Synthesis of 2-[3-[[N-(Benzoxazol-2-yl)-N-3-phenoxypropyl]aminomethyl]phenoxy]butyric acid

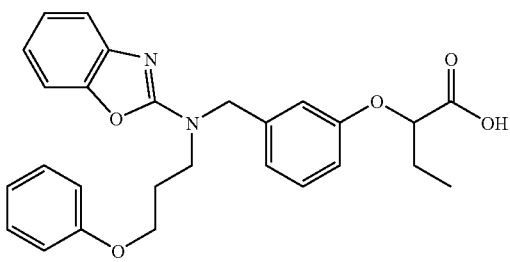

MS (m/z) 460 (M+).

Sodium 2-[3-[[N-(benzoxazol-2-yl)-N-3-phenoxypropyl]aminomethyl]phenoxy]butyrate

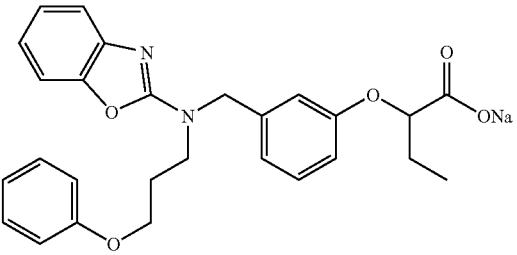

$^1$H-NMR (400 MHz, DMSO-$d_6$) δ 0.90 (t, J=7 Hz, 3H), 1.67–1.75 (m, 2H), 2.09–2.11 (m, 2H), 3.67 (t, J=7 Hz, 2H), 3.99–4.03 (m, 3H), 4.69 (s, 2H), 6.65–6.75 (m, 3H), 6.90–7.00 (m, 4H), 7.13 (t, J=8 Hz, 2H), 7.24–7.29 (m, 3H), 7.33 (d, J=7 Hz, 1H).

Example 14

Synthesis of 2-[3-[[N-(Benzoxazol-2-yl)-N-3-(4-methoxyphenoxy)propyl]aminomethyl]phenoxy]butyric acid

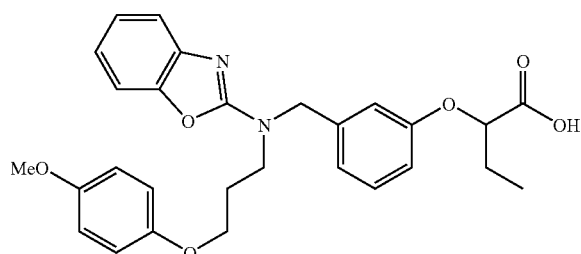

MS (m/z) 490 (M+).

Sodium 2-[3-[[N-(benzoxazol-2-yl)-N-3-(4-methoxyphenoxy)propyl]aminomethyl]phenoxy]butyrate

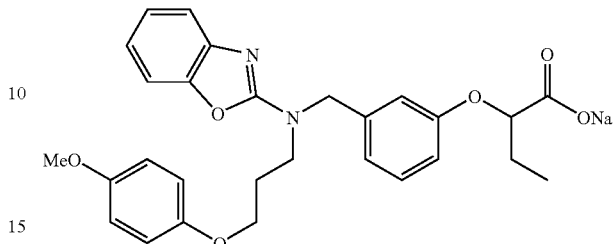

$^1$H-NMR (400 MHz, CD$_3$OD) δ 1.03 (t, J=7 Hz, 3H), 1.87–1.92 (m, 2H), 2.09 (quintet, J=6.6 Hz, 2H), 3.67–3.73 (m, 5H), 3.95 (t, J=6 Hz, 2H), 4.35 (t, J=6 Hz, 1H), 4.74 (s, 2H), 6.78–6.90 (m, 7H), 7.00 (td, J=8, 1 Hz, 1H), 7.14–7.27 (m, 4H).

Example 15

Synthesis of 2-[3-[[N-(Benzoxazol-2-yl)-N-3-(4-methoxyphenoxy)propyl]aminomethyl]phenoxy]-2-methylpropionic acid

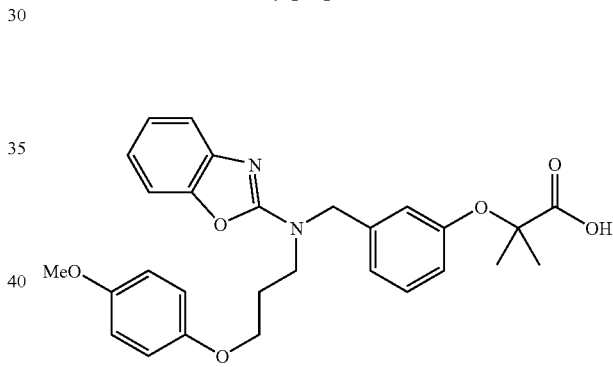

MS (m/z) 490 (M+).

Sodium 2-[3-[[N-(benzoxazol-2-yl)-N-3-(4-methoxyphenoxy)propyl]aminomethyl]phenoxy]-2-methylpropionate

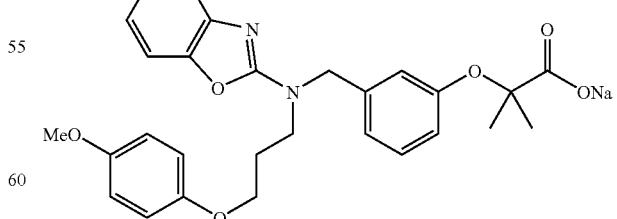

$^1$H-NMR (400 MHz, CDCl$_3$) δ 1.35 (s, 6H), 2.03 (quintet, J=7 Hz, 2H), 3.60 (t, J=7 Hz, 2H), 3.70 (s, 3H), 3.87 (t, J=6 Hz, 2H), 4.59 (s, 2H), 6.70–6.83 (m, 6H), 6.93 (t, J=8 Hz, 1H), 7.00–7.02 (m, 2H), 7.08 (t, J=8 Hz, 1H), 7.13 (d, J=8 Hz, 1H), 7.29 (d, J=8 Hz, 1H).

Example 16

Synthesis of 2-[3-[[N-(Benzoxazol-2-yl)-N-3-(4-chlorophenoxy)propyl]aminomethyl]phenoxy]-2-methylpropionic acid

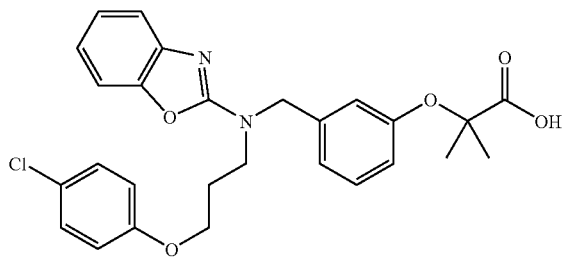

MS (m/z) 494 (M+), 496 (M⁺+2).

Sodium 2-[3-[[N-(benzoxazol-2-yl)-N-3-(4-chlorophenoxy)propyl]aminomethyl]phenoxy]-2-methyl-propionate

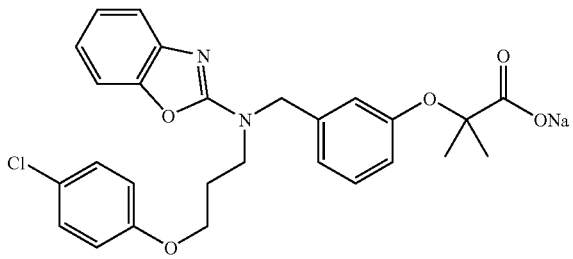

¹H-NMR (400 MHz, DMSO-$d_6$) δ 1.35 (s, 6H), 2.08 (quintet, J=7 Hz, 2H), 3.64 (t, J=7 Hz, 2H), 4.01 (t, J=6 Hz, 2H), 4.66 (s, 2H), 6.71 (d, J=8 Hz, 1H), 6.72–6.76 (m, 2H), 6.94–7.00 (m, 3H), 7.08 (t, J=8 Hz, 1H), 7.13 (t, J=8 Hz, 1H), 7.26–7.35 (m, 4H).

Example 17

Synthesis of 2-[4-[[N-(Benzoxazol-2-yl)-N-3-(3-dimethylaminophenoxy)propyl]aminomethyl]phenoxy]-2-methylpropionic acid

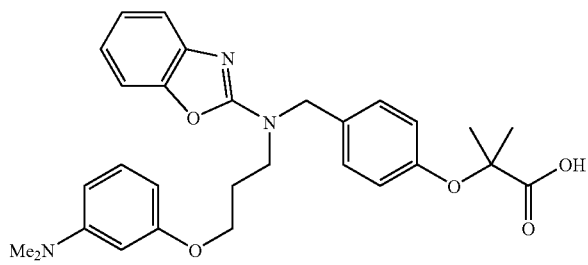

MS (m/z) 489 (M⁺).

Sodium 2-[4-[[N-(benzoxazol-2-yl)-N-3-(3-dimethylaminophenoxy)propyl]aminomethyl]phenoxy]-2-methylpropionate

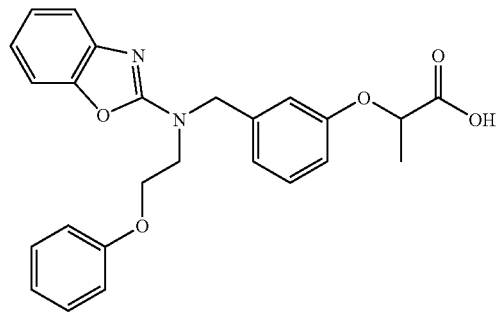

¹H-NMR (400 MHz, CD$_3$OD) δ 1.52 (s, 6H), 2.05–2.08 (m, 2H), 2.87 (s, 6H), 3.86 (t, J=5 Hz, 2H), 4.18 (t, J=5 Hz, 2H), 4.80 (s, 2H), 6.30–6.47 (m, 3H), 6.84 (dd, J=7, 2 Hz, 2H), 7.03–7.09 (m, 2H), 7.15–7.31 (m, 5H).

Example 18

Synthesis of 2-[3-[[N-(Benzoxazol-2-yl)-N-2-phenoxyethyl]aminomethyl]phenoxy]propionic acid

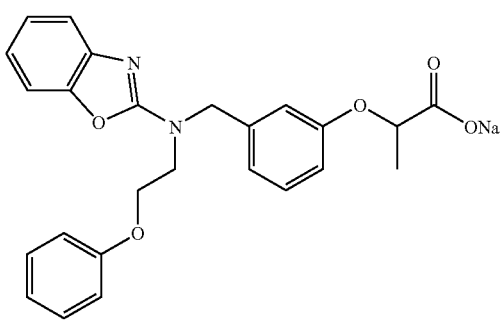

MS (m/z) 432 (M⁺).

Sodium 2-[3-[[N-(benzoxazol-2-yl)-N-2-phenoxyethyl]aminomethyl]phenoxy]propionate

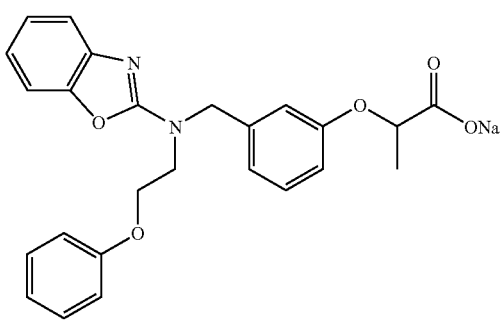

¹H-NMR (400 MHz, DMSO-$d_6$) δ 1.46 (d, J=7 Hz, 3H), 3.87 (t, J=6 Hz, 2H), 4.23 (t, J=6 Hz, 2H), 4.75–4.80 (m, 3H), 6.76 (dd, J=8, 2 Hz, 1H), 6.88–6.93 (m, 4H), 7.02 (t, J=8 Hz, 1H), 7.16 (t, J=8 Hz, 1H), 7.24 (t, J=8 Hz, 1H), 7.28–7.32 (m, 4H), 7.40 (d, J=8 Hz, 1H).

Exsample 19

Synthesis of 2-[3-[[N-(Benzoxazol-2-yl)-N-3-(3-dimethylaminophenoxy)propyl]aminomethyl]phenoxy]propionic acid

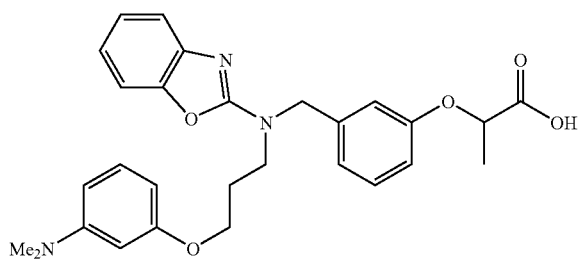

MS (m/z) 489 (M+).

Sodium 2-[3-[[N-(benzoxazol-2-yl)-N-3-(3-dimethylaminophenoxy)propyl]aminomethyl]phenoxy]propionate

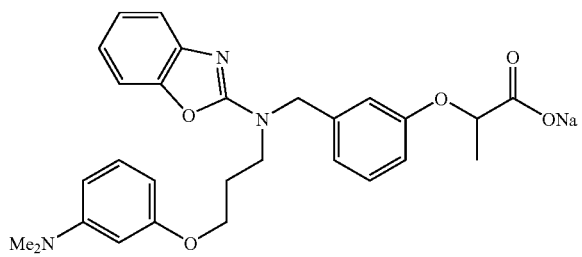

$^1$H-NMR (400 MHz, CDCl$_3$) δ 1.38 (d, J=7 Hz, 3H), 2.04–2.08 (m, 2H), 2.86 (s, 6H), 3.60–3.65 (m, 2H), 3.93 (t, J=6 Hz, 2H), 4.51–4.55 (m, 1H), 4.57 (d, J=16 Hz, 1H), 4.66 (d, J=16 Hz, 1H), 6.25–6.28 (m, 2H), 6.36 (dd, J=11, 2 Hz, 1H), 6.70 (d, J=8 Hz, 1H), 6.77 (d, J=8 Hz, 2H), 6.94 (t, J=8 Hz, 1H), 7.02–7.11 (m, 3H), 7.15 (d, J=8 Hz, 1H), 7.31 (d, J=8 Hz, 1H).

Exsample 20

2-[3-[[N-(Benzoxazol-2-yl)-N-3-(4-methoxyphenoxy)propyl]aminomethyl]phenoxy]propionic acid

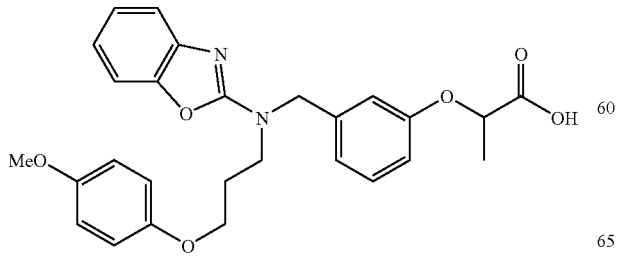

MS (m/z) 476 (M+).

Sodium 2-[3-[[N-(benzoxazol-2-yl)-N-3-(4-methoxyphenoxy)propyl]aminomethyl]phenoxy]propionate

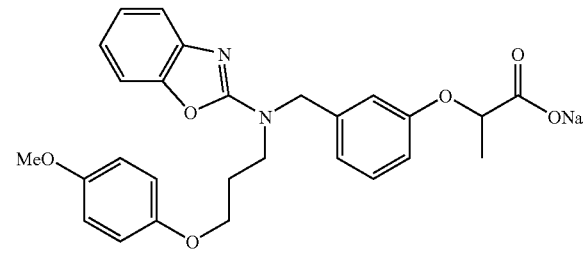

$^1$H-NMR (400 MHz, CD$_3$OD) δ 1.50 (d, J=7 Hz, 3H), 2.09 (quintet, J=7 Hz, 2H), 3.68–3.75 (m, 5H), 3.94 (t, J=6 Hz, 2H), 4.58 (q, J=7 Hz, 1H), 4.74 (s, 2H), 6.78–6.87 (m, 7H), 7.00 (td, J=8, 1 Hz, 1H), 7.12–7.27 (m, 4H).

Example 21

Synthesis of 2-[3-[[N-(Benzoxazol-2-yl)-N-2-phenoxyethyl]aminomethyl]phenoxy]-2-methylpropionic acid

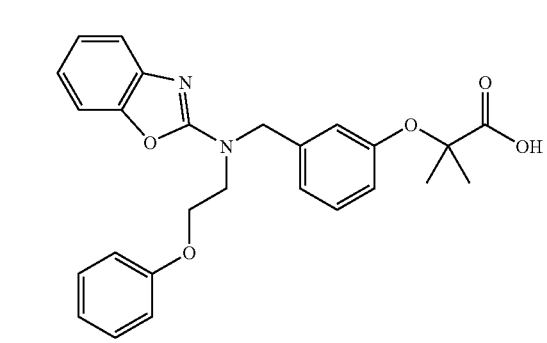

MS (m/z) 446 (M+).

Example 22

Synthesis of 2-[4-[[N-(Benzoxazol-2-yl)-N-2-phenoxyethyl]aminomethyl]phenoxy]-2-methylpropionic acid

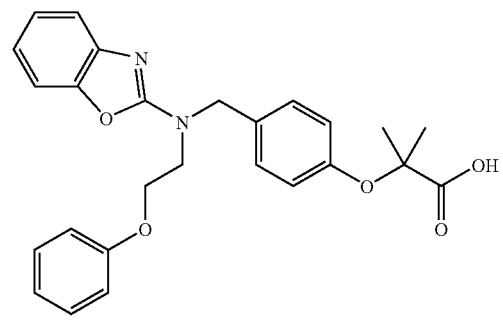

MS (m/z) 446 (M+).

Example 23

Synthesis of 2-[2-[[N-(Benzoxazol-2-yl)-N-2-phenoxyethyl]aminomethyl]phenoxy]-2-methylpropionic acid

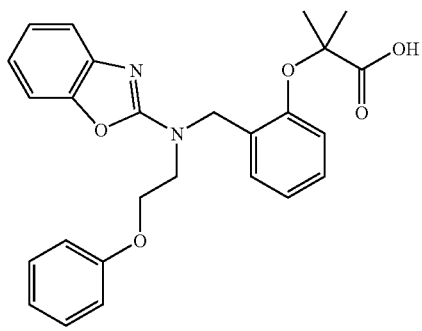

MS (m/z) 446 (M+).

Example 24

Synthesis of 2-[3-[[N-(Benzoxazol-2-yl)-N-2-phenoxyethyl]aminomethyl]phenoxy]butyric acid

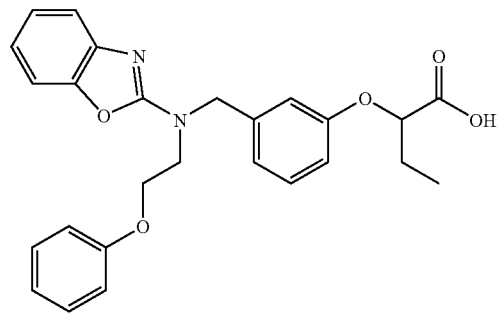

MS (m/z) 446 (M+).

Example 25

Synthesis of 2-[3-[[N-(Benzoxazol-2-yl)-N-2-(3-dimethylaminophenoxy)ethyl]aminomethyl]phenoxy]-2-methylpropionic acid

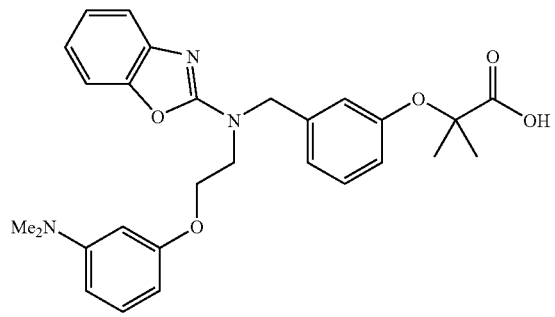

MS (m/z) 489 (M+).

Example 26

Synthesis of 2-[3-[[N-(Benzoxazol-2-yl)-N-3-(3-dimethylaminophenoxy)propyl]aminomethyl]phenoxy]-2-methylpropionic acid

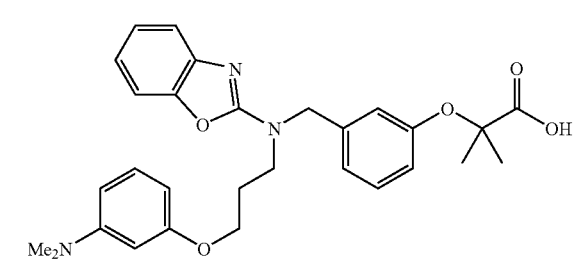

MS (m/z) 503 (M+).

Example 27

Synthesis of 2-[4-[[N-(Benzoxazol-2-yl)-N-2-(4-methoxyphenoxy)ethyl]aminomethyl]phenoxy]-2-methylpropionic acid

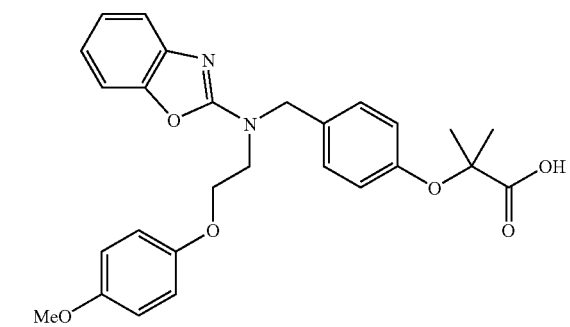

MS (m/z) 476 (M+).

Example 28

Synthesis of 2-[4-[[N-(Benzoxazol-2-yl)-N-3-(4-methoxyphenoxy)propyl]aminomethyl]phenoxy]-2-methylpropionic acid

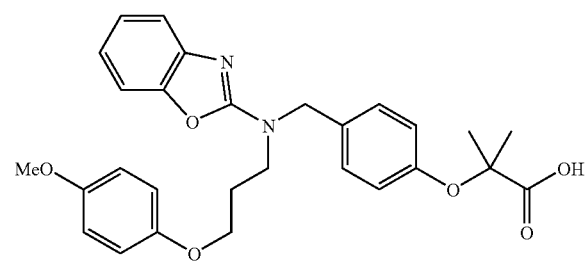

MS (m/z) 490 (M+).

Example 29

Synthesis of 2-[4-[[N-(Benzoxazol-2-yl)-N-2-(4-chlorophenoxy)ethyl]aminomethyl]phenoxy]-2-methylpropionic acid

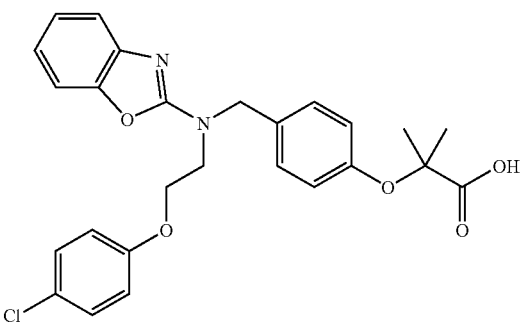

MS (m/z) 480 (M⁺), 482 (M⁺+2).

Example 30

Synthesis of 2-[4-[[N-(Benzoxazol-2-yl)-N-3-(4-chlorophenoxy)propyl]aminomethyl]phenoxy]-2-methylpropionic acid

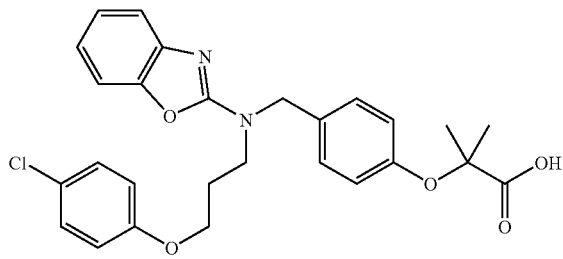

MS (m/z) 494 (M⁺), 496 (M⁺+2).

Production Example 4

N-2-Phenoxyethyl-3-hydroxyphenylacetamide

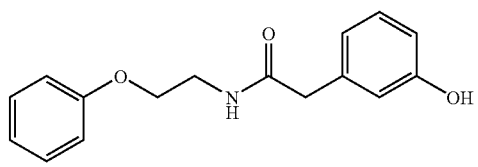

3-Hydroxyphenylacetate (1.5 g, 9.88 mmol) was dissolved in dichloromethane. WSC.HCl (2.82 g, 14.76 mmol) and 2-phenoxyethylamine (1.5 g, 10.95 mmol) were added thereto, and then the resultant mixture was stirred for 4 hours at room temperature. After completion of reaction, water was added to the reaction mixture. The resultant mixture was extracted with chloroform, followed by washing with brine. The resultant mixture was subjected to drying over anhydrous sodium sulfate, concentration under reduced pressure, and purification by chromatography, whereby 2.85 g, a stoichiometric amount, of the target compound was obtained as a pale yellow oil.

$^1$H NMR (400 MHz, CDCl$_3$) δ 3.38 (s, 2H) 3.61 (q, J=5 Hz, 2H) 4.00 (t, J=5 Hz, 2H), 5.97 (br, 1H), 6.72 (m, 4H), 6.96 (t, J=8 Hz, 1H), 7.26 (m, 4H).

Production Example 5

Synthesis of tert-Butyl 2-[3-(N-2-phenoxyethylaminocarbonylmethyl)phenoxy]propionate

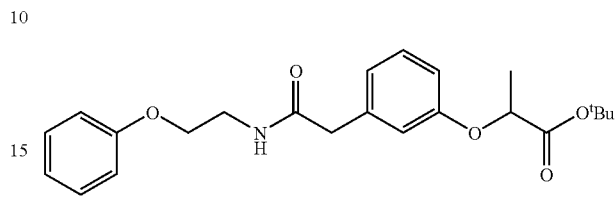

N-2-Phenoxyethyl-3-hydroxyphenylacetoamide (1.4 g, 5.16 mmol) was dissolved in acetonitrile (10 mL). tert-Butyl 2-bromopropionate (1.3 g, 6.19 mmol) and potassium carbonate (1.07 g, 7.74 mmol) were added thereto, and then the resultant mixture was stirred overnight at 80° C. After completion of reaction, the reaction mixture was subjected to concentration under reduced pressure. Ethyl acetate was added thereto. The mixture was washed with water and brine and dried over anhydrous sodium sulfate. The dried mixture was subjected to concentration under reduced pressure and purification by chromatography, whereby 1.14 g of the target compound was obtained as a pale yellow oil (yield 54%).

Production Example 6

Synthesis of tert-Butyl 2-[3-[2-(N-2-phenoxyethyl)aminoethyl]phenoxy]propionate

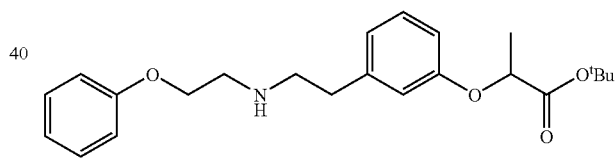

tert-Butyl 2-[3-(2-phenoxyehtylaminocarbonylmethyl)phenoxy]propionate (1.14 g, 2.86 mmol) was dissolved in tetrahydrofuran (5 mL) under argon atmosphere. The mixture was cooled to 0° C., and then a 1M borane-THF complex in THF solution (8.5 mL, 8.5 mmol) was added thereto. The resultant mixture was stirred for 30 minutes, followed by stirring for 3 hours at 50° C. After completion of reaction, the reaction mixture was allowed to cool. Subsequently, methanol was added thereto and subjected to concentration under reduced pressure. Subsequently, chloroform was added to the concentrate. The mixture was washed with water and brine and dried over anhydrous sodium sulfate. The dried mixture was subjected to concentration under reduced pressure and purification by chromatography, whereby 940 mg of the target compound was obtained as a colorless oil (yield 85%).

$^1$H NMR (400 MHz, CDCl$_3$) δ 1.43 (s, 9H,) 1.56 (d, J=7 Hz, 3H), 2.79 (t, J=7 Hz, 2H), 2.93 (t, J=7 Hz, 2H), 3.01 (t, J=5 Hz, 2H), 4.05 (t, J=5 Hz, 2H), 4.60 (q, J=7 Hz, 1H), 6.69 (dd, J=2, 8 Hz, 1H), 6.75 (s, 1H), 6.82 (d, J=8 Hz, 1H), 6.92 (m, 3H), 7.18 (t, J=8 Hz, 1H), 7.26 (m, 2H).

Production Example 7

Synthesis of tert-Butyl 2-[3-[2-[N-(benzoxazol-2-yl)-N-2-phenoxyethyl]aminoethyl]phenoxy]propionate

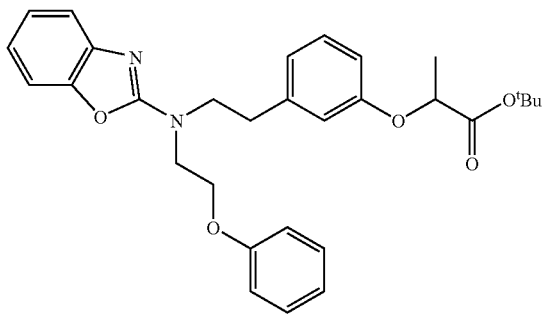

tert-Butyl 2-[3-[2-(N-2-phenoxyehtyl)aminoethyl]phenoxy]propionate (200 mg, 0.519 mmol) was dissolved in N,N-dimethylformamide. Subsequently, 2-chlorobenzoxazole (95 mg, 0.623 mmol) and diisopropylethylamine (0.1 mL, 0.623 mmol) were added thereto, and the mixture was stirred overnight at 80° C. After completion of reaction, ethyl acetate was added. Washing was performed with water and brine, followed by drying over magnesium sulfate. The reaction mixture was subjected to concentration under reduced pressure, and purification by chromatography, whereby 266 mg, a stoichiometric amount, of the target compound was obtained as a yellow oil.

$^1$H NMR (400 MHz, CDCl$_3$) δ 1.43 (s, 9H) 1.57 (d, J=8 Hz, 3H), 3.02 (t, J=8 Hz, 2H), 3.86 (m, 4H), 4.20 (t, J=5 Hz, 2H), 4.60 (q, J=7 Hz, 1H), 6.69 (dd, J=2, 8 Hz, 1H), 6.91 (m, 6H), 7.18 (t, J=8 Hz, 1H), 7.26 (m, 4H), 7.36 (d, J=8 Hz, 1H).

Example 31

Synthesis of 2-[3-[2-[N-(Benzoxazol-2-yl)-N-2-phenoxyethyl]aminoethyl]phenoxy]propionic acid

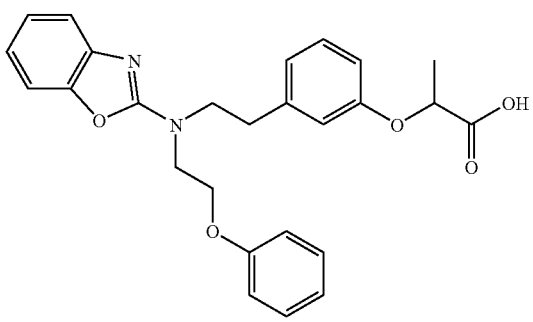

tert-Butyl 2-[3-[2-[N-(benzoxazol-2-yl)-N-2-phenoxyehtyl]aminoethyl]phenoxy]propionate (266 mg, 0.530 mmol) was dissolved in dichloromethane (3 mL). Subsequently, trifluoroacetic acid (1 mL) was added thereto, and the mixture was stirred for 1 hour at room temperature. After completion of reaction, the reaction mixture was subjected to concentration under reduced pressure, and the residue was subjected to purification by preparative TLC, whereby 115 mg of the target compound was obtained as a yellow oil (yield 54%).

$^1$H NMR (400 MHz, CDCl$_3$) δ 1.60 (d, J=7 Hz, 3H), 3.02 (t, J=6 Hz, 2H), 3.68–4.19 (m, 6H), 4.60 (q, J=7 Hz, 1H), 6.58 (s, 1H), 6.79 (d, J=8 Hz, 1H), 6.85 (d, J=8 Hz, 2H), 6.90–6.97 (m, 2H), 7.12 (t, J=8 Hz, 1H), 7.26 (m, 5H), 7.44 (d, J=8 Hz, 1H).

In a manner similar to that described in Example 31, the compounds of Examples 32 through Example 73 were synthesized.

Example 32

Synthesis of 2-[3-[3-[N-(Benzoxazol-2-yl)-N-2-phenoxyethyl]aminopropyl]phenoxy]-2-methylpropionic acid

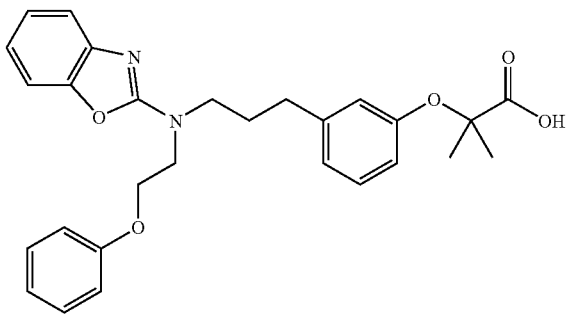

MS (m/z) 474 (M$^+$).

Example 33

Synthesis of 2-[4-[3-[N-(Benzoxazol-2-yl)-N-2-phenoxyethyl]aminopropyl]phenoxy]-2-methylpropionic acid

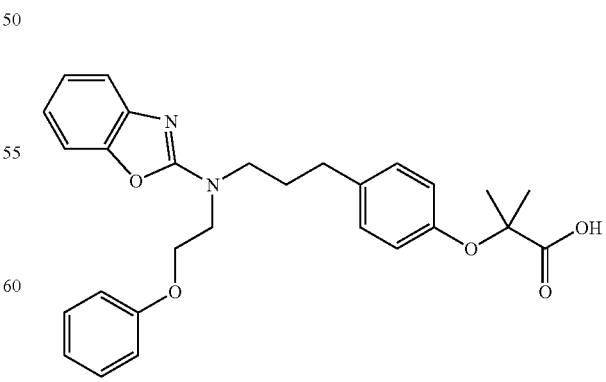

MS (m/z) 474 (M$^+$).

Example 34

Synthesis of 2-[3-[2-[N-(Benzoxazol-2-yl)-N-2-(4-fluorophenoxy)ethyl]aminoethyl]phenoxy]propionic acid

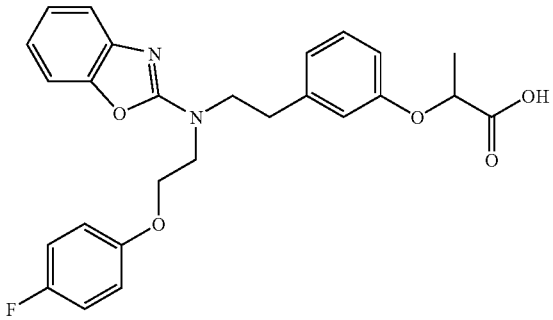

MS (m/z) 464 (M⁺).

Example 35

Synthesis of 2-[3-[2-[N-(5-Fluorobenzoxazol-2-yl)-N-2-(4-fluorophenoxy)ethyl]aminoethyl]phenoxy] propionic acid

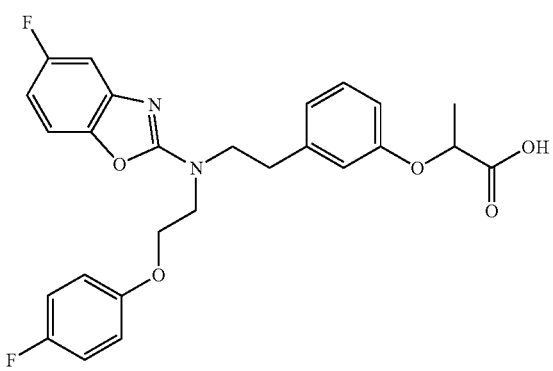

¹H-NMR (400 MHz, CDCl₃) δ 1.57 (d, J=7 Hz, 3H), 2.90 (t, J=7 Hz, 2H), 3.64–3.80 (m, 6H), 4.65 (q, J=7 Hz, 1H), 6.67–7.12 (m, 11H).

Example 36

Synthesis of 2-[3-[2-[N-(5-Chlorobenzoxazol-2-yl)-N-2-(4-fluorophenoxy)ethyl]aminoethyl]phenoxy] propionic acid

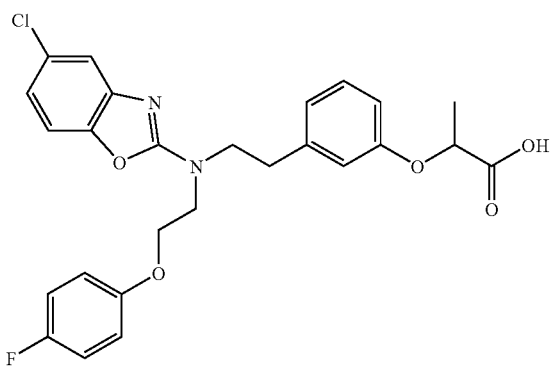

MS (m/z) 498 (M⁺), 500 (M⁺+2).

Example 37

Synthesis of 2-[3-[2-[N-2-(4-Fluorphenoxy)ethyl-N-(5-methoxybenzoxazol-2-yl)]aminoethyl]phenoxy] propionic acid

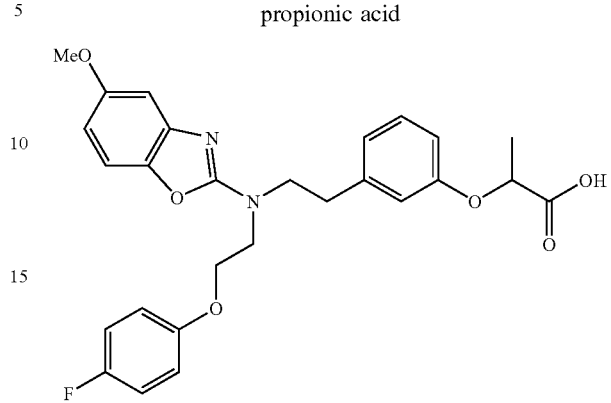

¹H-NMR (400 MHz, CDCl₃) δ 1.50 (d, J=7 Hz, 3H), 2.84 (t, J=7 Hz, 2H), 3.53–3.95 (m, 9H), 4.61 (q, J=7 Hz, 1H), 6.51 (dd, J=3, 9 Hz, 1H), 6.63–6.92 (m, 7H), 7.02–7.30 (m, 3H).

Example 38

Synthesis of 2-[3-[2-[N-(Benzoxazol-2-yl)-N-3-phenoxypropyl]aminoethyl]phenoxy]butyric acid

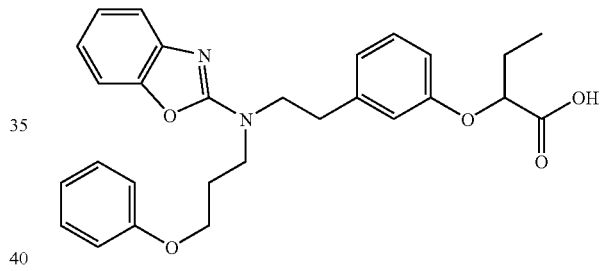

¹H NMR (400 MHz, CDCl₃) δ 1.07 (t, J=7 Hz, 3H), 2.01 (m, 4H), 2.87 (t, J=7 Hz, 2H), 3.45–3.74 (4H, m), 3.92 (t, J=6 Hz, 2H), 4.55 (t, J=6 Hz, 1H), 6.77 (m, 2H), 6.85 (d, J=8 Hz, 2H), 6.90–7.26 (m, 8H), 7.33 (d, J=8 Hz, 1H).

Example 39

Synthesis of 2-[3-[2-[N-(5-Fluorobenzoxazol-2-yl)-N-3-phenoxypropyl]aminoethyl]phenoxy]butyric acid

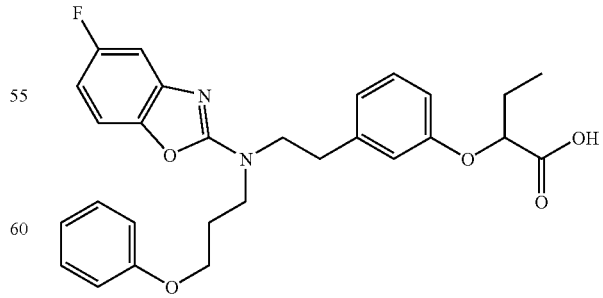

¹H NMR (400 MHz, CDCl₃) δ 1.07 (t, J=8 Hz, 3H), 2.00 (m, 4H), 2.91 (t, J=7 Hz, 2H), 3.49–3.74 (m, 4H), 3.95 (t, J=6 Hz, 2H), 4.56 (q, J=6 Hz, 1H), 6.65–7.26 (m, 11H), 8.06 (d, J=7 Hz, 1H).

Example 40

Synthesis of 2-[3-[2-[N-(5-Chlorobenzoxazol-2-yl)-N-3-phenoxypropyl]aminoethyl]phenoxy]butyric acid

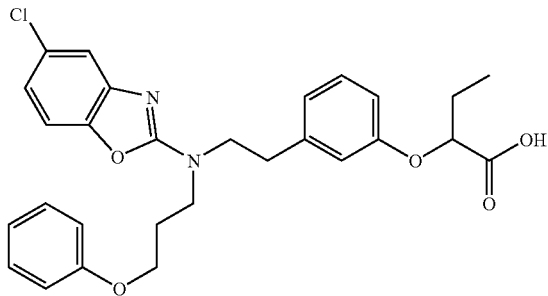

MS (m/z) 508 (M$^+$), 510 (M$^+$+2).

Example 41

Synthesis of 2-[3-[2-[N-(Benzoxazol-2-yl)-N-2-phenoxyethyl]aminoethyl]phenoxy]butyric acid

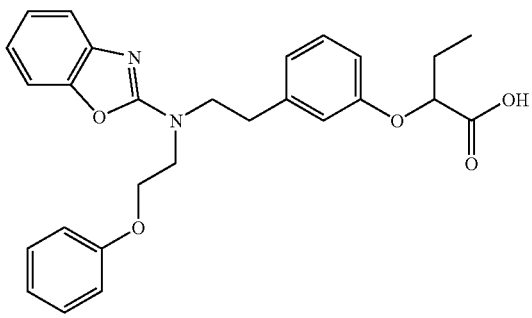

$^1$H NMR (400 MHz, CDCl$_3$) δ 1.08 (t, J=7 Hz, 3H), 2.00 (m, 2H), 2.95 (t, J=7 Hz, 2H), 3.61 (m, 1H), 3.77–4.14 (m, 5H), 4.52 (q, J=6 Hz, 1H), 6.71 (s, 1H), 6.80 (m, 2H), 6.85 (d, J=7 Hz, 1H), 6.92 (t, J=7 Hz, 1H), 7.04 (t, J=8 Hz, 1H), 7.16–7.26 (m, 6H), 7.37 (d, J=8 Hz, 1H).

Example 42

Synthesis of 2-[3-[2-[N-(5-Methoxybenzoxazol-2-yl)-N-2-phenoxyethyl]aminoethyl]phenoxy]butyric acid

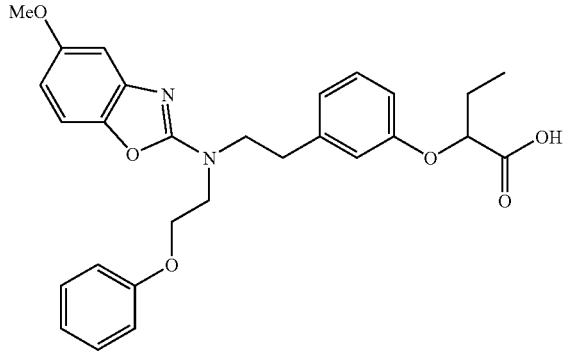

MS (m/z) 490 (M$^+$).

Example 43

Synthesis of 2-[3-[2-[N-(5-Fluorobenzoxazol-2-yl)-N-2-phenoxyethyl]aminoethyl]phenoxy]propionic acid

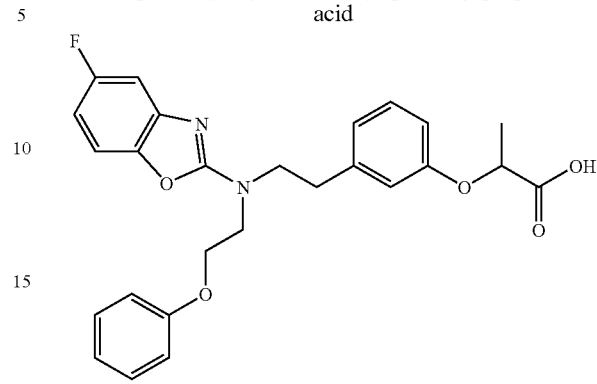

$^1$H NMR (400 MHz, CDCl$_3$) δ 1.60 (d, J=7 Hz, 3H), 3.00 (t, J=7 Hz, 2H), 3.70–4.18 (m, 6H), 4.67 (q, J=7 Hz, 1H), 6.62 (s, 1H), 6.79 (m, 2H), 6.85 (d, J=8 Hz, 2H), 6.90 (d, J=8 Hz, 1H), 6.95 (t, J=7 Hz, 1H), 7.10–7.30 (m, 5H).

Example 44

Synthesis of 2-[3-[2-[N-(5-Methoxybenzoxazol-2-yl)-N-2-phenoxyethyl]aminoethyl]phenoxy]propionic acid

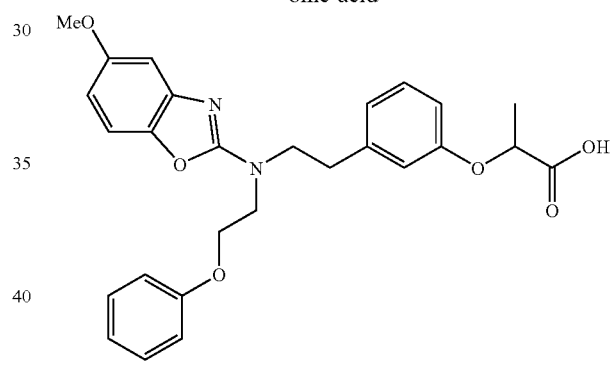

$^1$H NMR (400 MHz, CDCl$_3$) δ 1.59 (d, J=7 Hz, 3H), 3.00 (t, J=6 Hz, 2H), 3.67 (m, 1H), 3.80 (s, 3H), 3.90–4.21 (m, 5H), 4.58 (q, J=7 Hz, 1H), 6.49 (s, 1H), 6.72 (dd, J=2, 9 Hz, 1H), 6.79–6.98 (m, 6H), 7.09 (d, J=9 Hz, 2H), 7.21–7.30 (m, 2H).

Example 45

Synthesis of 2-[3-[2-[N-(Benzoxazol-2-yl)-N-2-(4-methoxyphenoxy)ethyl]aminoethyl]phenoxy]butyric acid

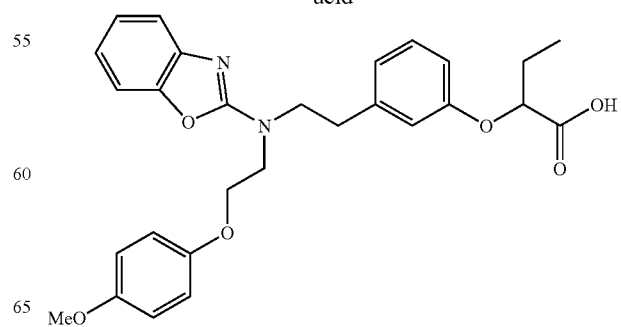

MS (m/z) 490 (M$^+$).

Example 46

Synthesis of 2-[3-[2-[N-(5-Fluorobenzoxazol-2-yl)-N-2-(4-methoxyphenoxy)ethyl]aminoethyl]phenoxy]butyric acid

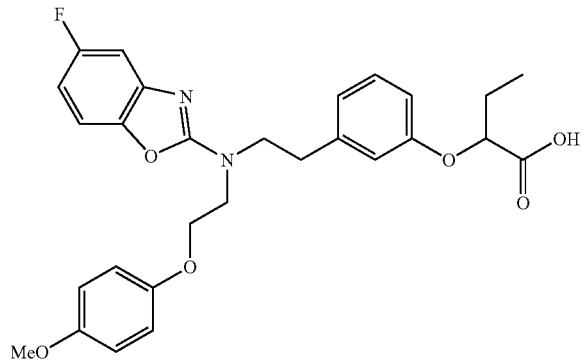

MS (m/z) 508 (M+).

Example 47

Synthesis of 2-[3-[2-[N-(5-Chlorobenzoxazol-2-yl)-N-2-(4-methoxyphenoxy)ethyl]aminoethyl]phenoxy]butyric acid

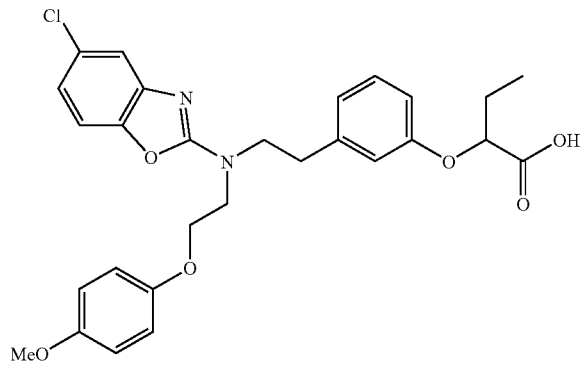

MS (m/z) 524 (M+), 526 (M++2).

Example 48

Synthesis of 2-[3-[2-[N-(5-Methoxybenzoxazol-2-yl)-N-2-(4-methoxyphenoxy)ethyl]aminoethyl]phenoxy]butyric acid

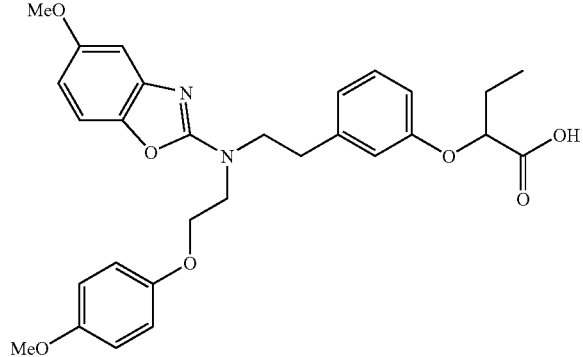

MS (m/z) 520 (M+).

Example 49

Synthesis of 2-[3-[2-[N-(5-Fluorobenzoxazol-2-yl)-N-3-(4-methoxyphenoxy)propyl]aminoethyl]phenoxy]butyric acid

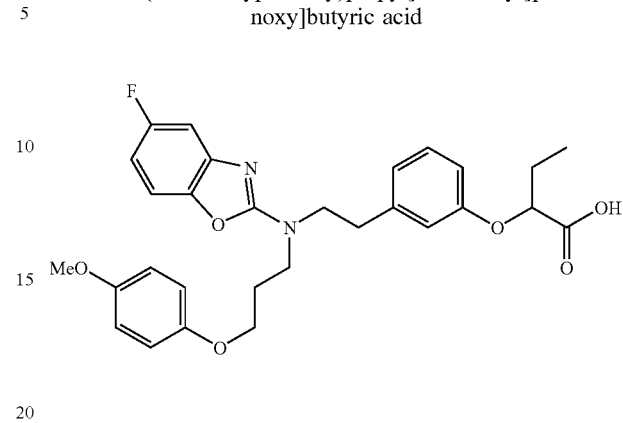

$^1$H NMR (400 MHz, CDCl$_3$) δ 1.07 (t, J=8 Hz, 3H), 2.01 (m, 4H), 2.92 (m, 2H), 3.49–3.74 (m, 7H), 3.91 (t, J=6 Hz, 2H), 4.56 (q, J=6 Hz, 1H), 6.74–7.26 (m, 11H).

Example 50

Synthesis of 2-[3-[2-[N-(Benzoxazol-2-yl)-N-3-(4-fluorophenoxy)propyl]aminoethyl]phenoxy]butyric acid

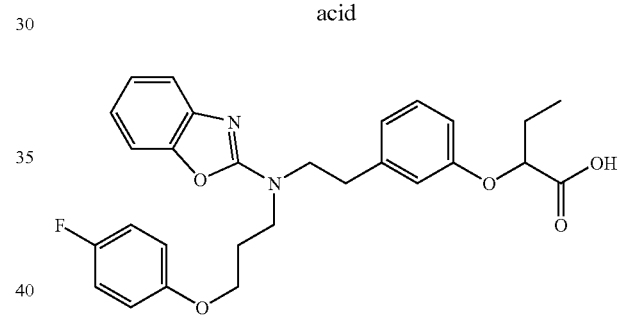

MS (m/z) 492 (M+).

Example 51

Synthesis of 2-[3-[2-[N-3-(4-Fluorophenoxy)propyl-N-(5-methoxybenzoxazol-2-yl)]aminoethyl]phenoxy]butyric acid

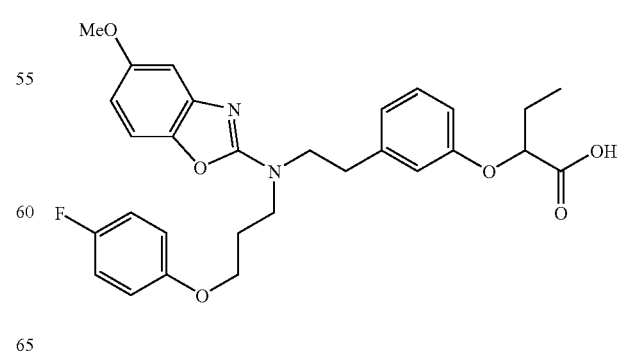

MS (m/z) 522 (M+).

Example 52

Synthesis of 2-[3-[2-[N-3-(4-Chlorophenoxy)propyl-N-(5-methoxybenzoxazol-2-yl)]aminoethyl]phenoxy]butyric acid

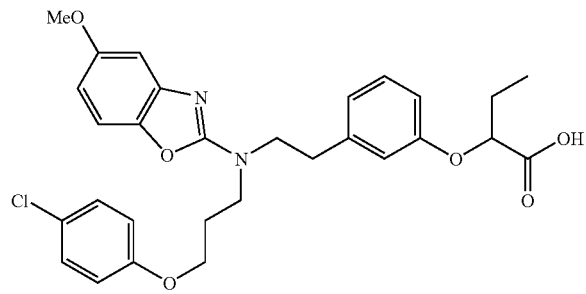

MS (m/z) 538 (M$^+$), 540 (M$^+$+2).

Example 53

Synthesis of 2-[3-[2-[N-(Benzoxazol-2-yl)-N-3-(4-chlorophenoxy)propyl]aminoethyl]phenoxy]butyric acid

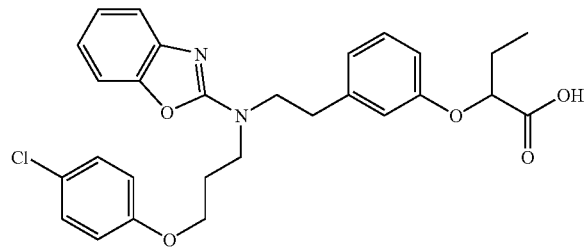

MS (m/z) 508 (M$^+$), 510 (M$^+$+2).

Example 54

Synthesis of 2-[3-[2-[N-(Benzoxazol-2-yl)-N-2-(4-chlorophenoxy)ethyl]aminoethyl]phenoxy]butyric acid

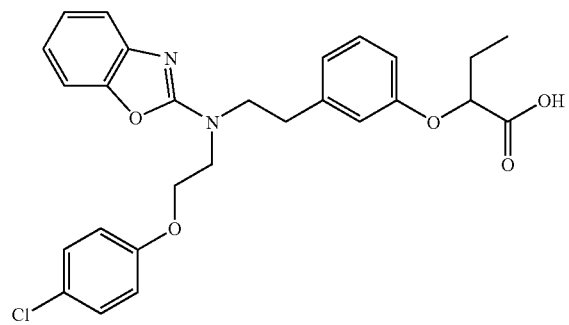

$^1$H-NMR (400 MHz, CD$_3$OD) δ 0.94 (t, J=7 Hz, 3H), 1.77–1.85 (m, 2H), 2.88 (t, J=7 Hz, 2H), 3.71 (t, J=5 Hz, 2H), 3.74 (t, J=7 Hz, 2H), 4.03 (t, J=5 Hz, 2H), 4.45 (t, J=5 Hz, 1H), 6.61–7.19 (m, 12H).

Example 55

Synthesis of 2-[3-[2-[N-(5-Chlorobenzoxazol-2-yl)-N-2-(4-chlorophenoxy)ethyl]aminoethyl]phenoxy]butyric acid

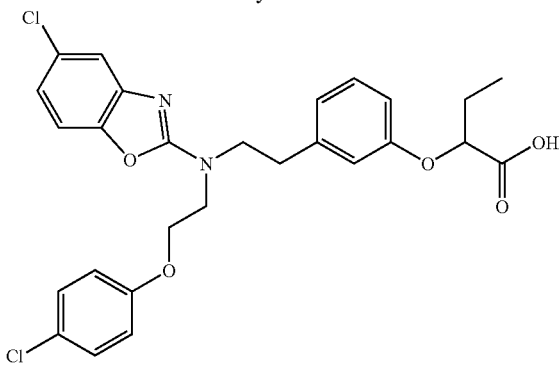

$^1$H-NMR (400 MHz, CD$_3$OD) δ 0.94 (t, J=7 Hz, 3H), 1.77–1.87 (m, 2H), 2.89 (t, J=7 Hz, 2H), 3.71–3.77 (m, 4H), 4.04 (t, J=5 Hz, 2H), 4.44 (t, J=6 Hz, 1H), 6.61–7.14 (m, 11H).

Example 56

Synthesis of 2-[3-[2-[N-2-(4-Chlorophenoxy)ethyl-N-(5-methoxybenzoxazol-2-yl)]aminoethyl]phenoxy]butyric acid

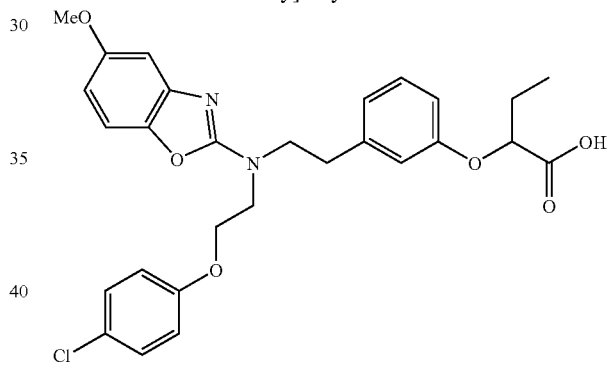

$^1$H-NMR (400 MHz, CD$_3$OD) δ 0.94 (t, J=7 Hz, 3H), 1.77–1.85 (m, 2H), 2.88 (t, J=7 Hz, 2H), 3.68 (s, 3H), 3.70–3.74 (m, 4H), 4.02 (t, J=5 Hz, 2H), 4.45 (t, J=6 Hz, 1H), 6.48–7.12 (m, 11H).

Example 57

Synthesis of 2-[3-[2-[N-(Benzothiazol-2-yl)-N-2-(4-chlorophenoxy)ethyl]aminoethyl]phenoxy]butyric acid

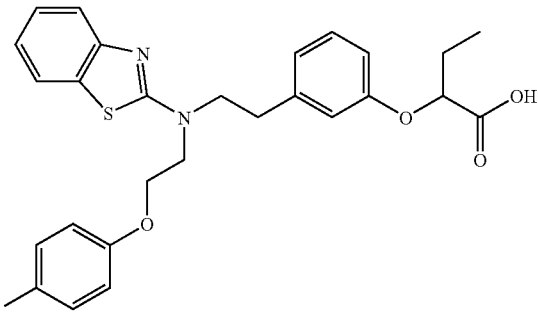

$^1$H-NMR (400 MHz, CD$_3$OD) δ 1.04 (t, J=7 Hz, 3H), 1.88–1.93 (m, 2H), 3.00 (t, J=7 Hz, 2H), 3.80 (t, J=7 Hz,

2H), 3.84 (t, J=5 Hz, 2H), 4.15 (t, J=5 Hz, 2H), 4.53 (t, J=5 Hz, 1H), 6.74–7.63 (m, 12H).

Example 58

Synthesis of 2-[3-[2-[N-(Benzoxazol-2-yl)-N-2-(4-methoxyphenoxy)ethyl]aminoethyl]phenoxy]propionic acid

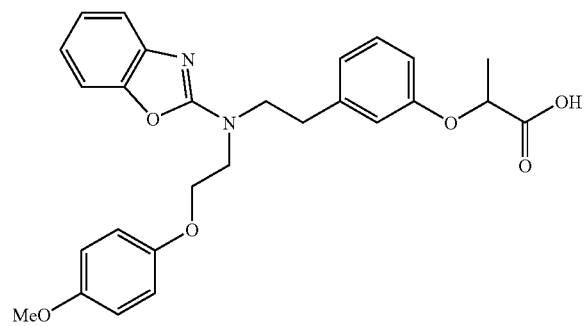

MS (m/z) 476 (M+).

Example 59

Synthesis of 2-[3-[2-[N-(5-Fluorobenzoxazol-2-yl)-N-2-(4-methoxyphenoxy)ethyl]aminoethyl]phenoxy]propionic acid

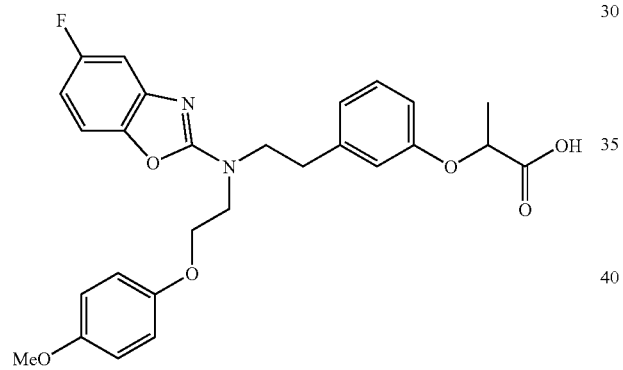

MS (m/z) 494 (M+).

Example 60

Synthesis of 2-[3-[2-[N-(5-Chlorobenzoxazol-2-yl)-N-2-(4-methoxyphenoxy)ethyl]aminoethyl]phenoxy]propionic acid

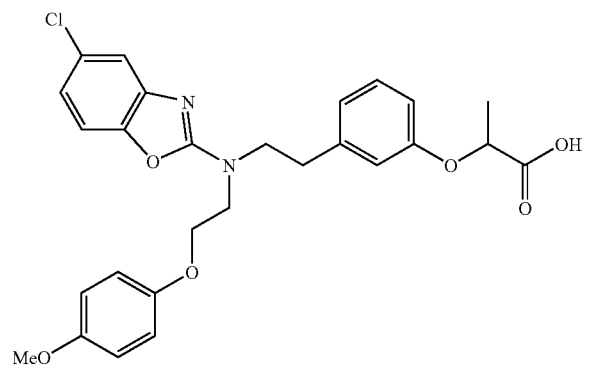

MS (m/z) 510 (M+), 512 (M++2).

Example 61

Synthesis of 2-[3-[2-[N-(5-Methoxybenzoxazol-2-yl)-N-2-(4-methoxyphenoxy)ethyl]aminoethyl]phenoxy]propionic acid

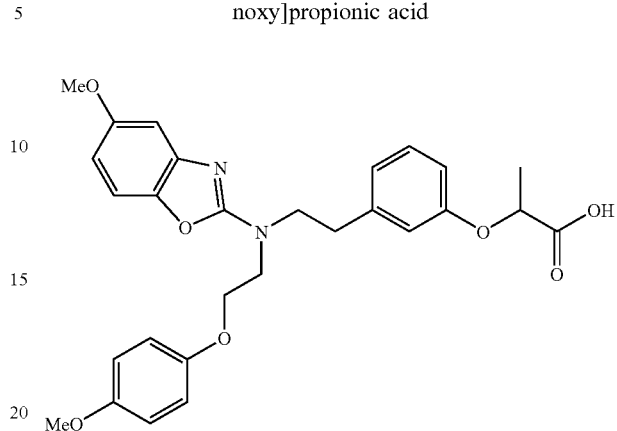

MS (m/z) 506 (M+).

Example 62

Synthesis of 2-[3-[2-[N-(Benzoxazol-2-yl)-N-3-phenoxypropyl]aminoethyl]phenoxy]propionic acid

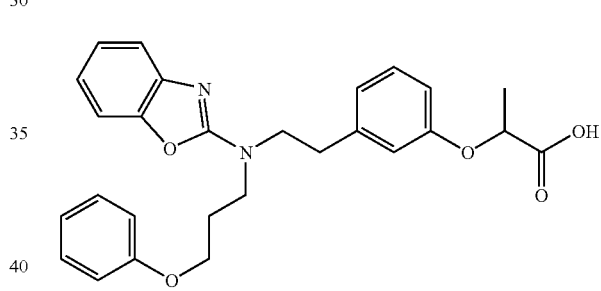

MS (m/z) 460 (M+).

Example 63

Synthesis of 2-[3-[2-[N-(5-Fluorobenzoxazol-2-yl)-N-3-phenoxypropyl]aminoethyl]phenoxy]propionic acid

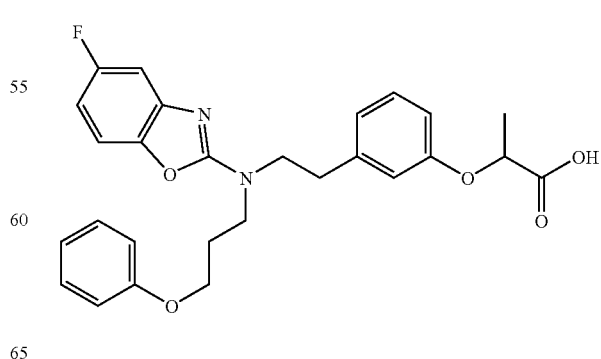

MS (m/z) 478 (M+).

Example 64

Synthesis of 2-[3-[2-[N-(5-Chlorobenzoxazol-2-yl)-N-3-phenoxypropyl]aminoethyl]phenoxy]propionic acid

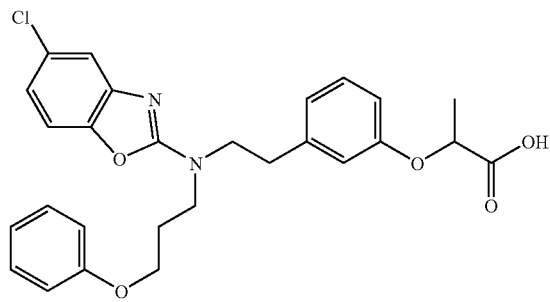

MS (m/z) 494 (M⁺), 496 (M⁺+2).

Example 65

Synthesis of 2-[3-[2-[N-(5-Methoxybenzoxazol-2-yl)-N-3-phenoxypropyl]aminoethyl]phenoxy]propionic acid

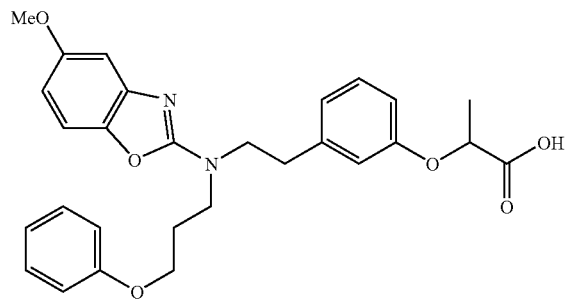

MS (m/z) 490 (M⁺).

Example 66

Synthesis of 2-[3-[2-[N-(Benzoxazol-2-yl)-N-3-(4-chlorophenoxy)propyl]aminoethyl]phenoxy]propionic acid

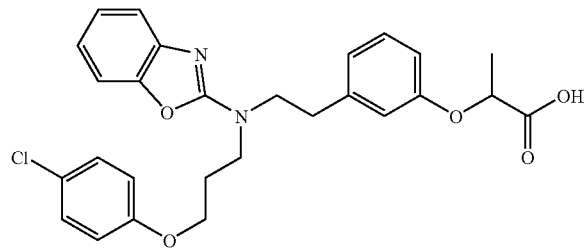

MS (m/z) 494 (M⁺), 496 (M⁺+2).

Example 67

Synthesis of 2-[3-[2-[N-3-(4-Chlorophenoxy)propyl-N-(5-fluorobenzoxazol-2-yl)]aminoethyl]phenoxy]propionic acid

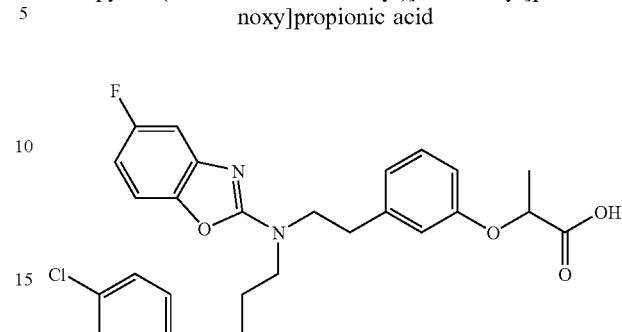

MS (m/z) 512 (M⁺), 514 (M⁺+2).

Example 68

Synthesis of 2-[3-[2-[N-(5-Chlorobenzoxazol-2-yl)-N-3-(4-chlorophenoxy)propyl]aminoethyl]phenoxy]propionic acid

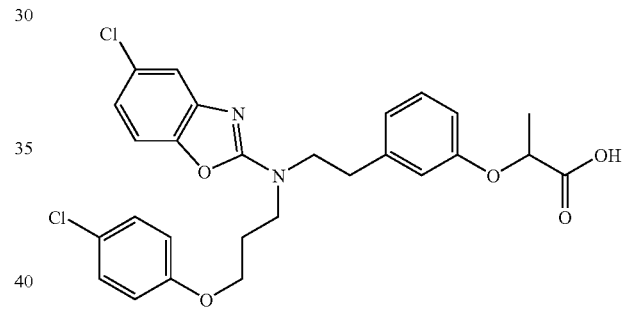

MS (m/z) 528 (M⁺), 530 (M⁺+2), 532 (M⁺+4).

Example 69

Synthesis of 2-[3-[2-[N-3-(4-Chlorophenoxy)propyl-N-(5-methoxybenzoxazol-2-yl)]aminoethyl]phenoxy]propionic acid

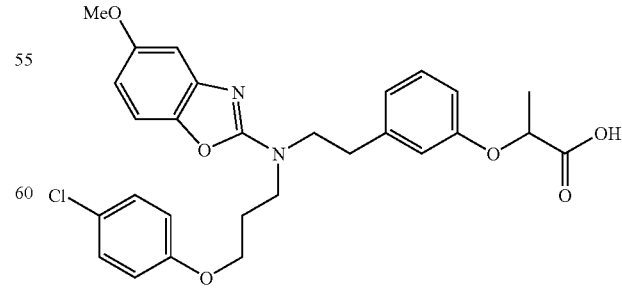

MS (m/z) 524 (M⁺), 526 (M⁺+2).

Example 70

Synthesis of 2-[3-[2-[N-(Benzoxazol-2-yl)-N-3-(4-fluorophenoxy)propyl]aminoethyl]phenoxy]propionic acid

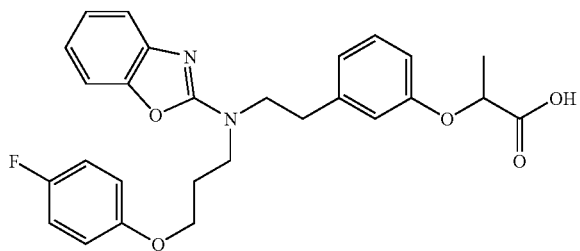

MS (m/z) 478 (M+).

Example 71

Synthesis of 2-[3-[2-[N-(5-Fluorobenzoxazol-2-yl)-N-3-(4-fluorophenoxy)propyl]aminoethyl]phenoxy]propionic acid

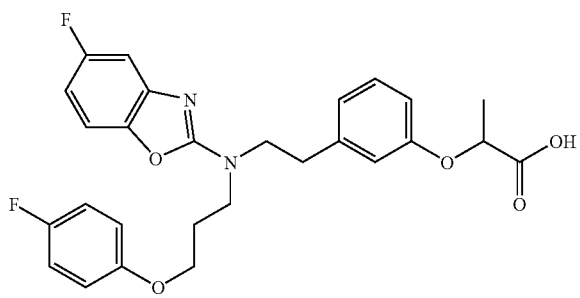

MS (m/z) 496 (M+).

Example 72

Synthesis of 2-[3-[2-[N-(5-Chlorobenzoxazol-2-yl)-N-3-(4-fluorophenoxy)propyl]aminoethyl]phenoxy]propionic acid

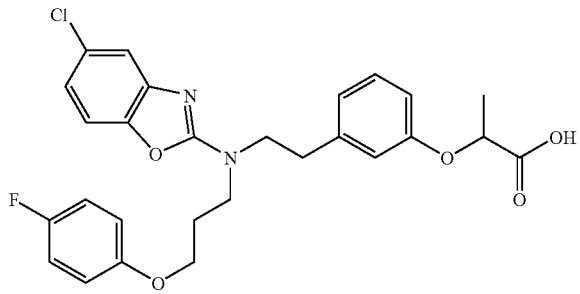

MS (m/z) 512 (M+), 514 (M++2).

Example 73

Synthesis of 2-[3-[2-[N-3-(4-Fluorophenoxy)propyl-N-(5-methoxybenzoxazol-2-yl)]aminoethyl]phenoxy]propionic acid

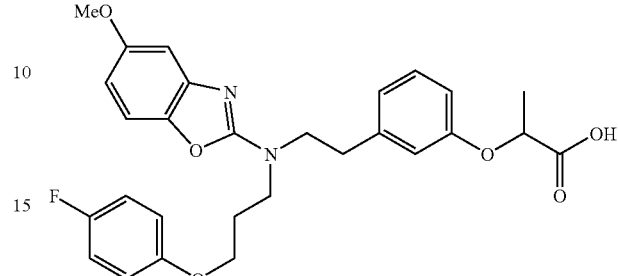

MS (m/z) 508 (M+).

Production Example 8

Synthesis of N-(4-Chlorophenoxyethyl)-3-(2-methoxyphenyl)propanamide

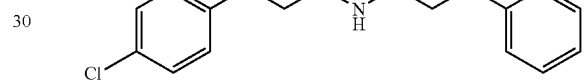

3-(2-Methoxyphenyl)propionic acid (8.3 g, 46.2 mmol) was dissolved in tetrahydrofuran (20 mL), and 4-chlorophenoxyethylamine (10.3 g, 60.0 mmol) was added dropwise thereto at room temperature. Subsequently, a solution (10 mL) of WSC.HCl (11.5 g, 60.0 mmol) in methylene chloride was slowly added dropwise thereto under ice-cooling, followed by stirring overnight. Under ice cooling, diluted hydrochloric acid was added dropwise thereto, followed by extraction with chloroform. The organic layer was washed with brine, and the resultant mixture was subjected to drying over anhydrous sodium sulfate, concentration under reduced pressure, and purification by silica gel chromatography (chloroform/methanol=20/1), whereby the target compound was obtained (12.8 g, 83%).

$^1$H-NMR (400 MHz, CDCl$_3$) δ 2.50 (t, J=8 Hz, 2H), 2.95 (t, J=8 Hz, 2H), 3.59–3.63 (m, 2H), 3.81 (s, 3H), 3.91 (t, J=5 Hz, 2H), 5.87 (br s, 1H), 6.75–6.84 (m, 4H), 7.12 (d, J=7 Hz, 2H), 7.23 (d, J=9 Hz, 2H).

Production Example 9

Synthesis of N-(4-Chlorophenoxyethyl)-3-(2-hydroxyphenyl)propanamide

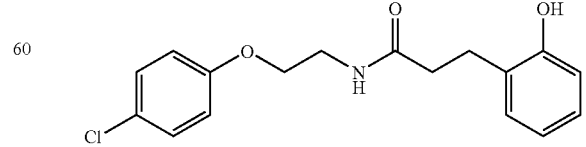

N-(4-Chlorophenoxyethyl)-3-(2-methoxyphenyl)propanamide (12.8 g, 38.3 mmol) was dissolved in methylene chloride (10.0 mL). Subsequently, a 1.0M-boron tribromide/ methylene chloride solution (49.8 mL, 49.8 mmol) was slowly added dropwise thereto under ice-cooling, followed by stirring for 1 hour at room temperature. Subsequently, water was slowly added dropwise thereto under ice-cooling, followed by stirring for 30 minutes. The resultant mixture was extracted with chloroform. The organic layer was washed with brine, and the resultant mixture was subjected to drying over anhydrous sodium sulfate, concentration under reduced pressure, and purification by column chromatography (n-hexane/ethyl acetate=20/1), whereby a white solid was obtained (11.6 g, 95%).

$^1$H-NMR (400 MHz, CDCl$_3$) δ 2.64 (t, J=6 Hz, 2H), 2.92 (t, J=6 Hz, 2H,), 3.61–3.65 (m, 2H), 3.94 (t, J=5 Hz, 2H), 5.99 (br s, 1H), 6.75 (d, J=9 Hz, 2H), 6.82 (t, J=7 Hz, 1H), 6.88 (d, J=7 Hz, 1H), 7.04 (d, J=7 Hz, 1H), 7.07 (t, J=7 Hz, 1H), 7.21 (d, J=9 Hz, 2H), 8.66 (s, 1H).

Production Example 10

Synthesis of tert-Butyl 2-[2-[2-[N-2-(4-chlorophenoxy)ethylaminocarbonyl]ethyl]phenoxy]-2-methylpropionate

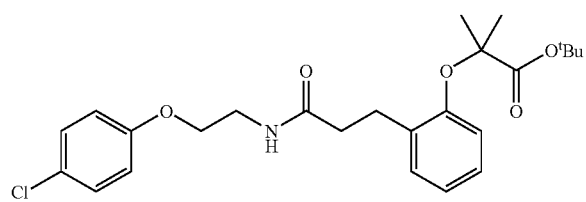

N-(4-Chlorophenoxyethyl)-3-(2-hydroxyphenyl)propanamide (11.6 g, 36.3 mmol) was dissolved in acetonitrile (15 mL), and potassium carbonate (15.0 g, 109 mmol) was added thereto. Subsequently, tert-butyl 2-bromoisobutyrate (20.2 g, 90.7 mmol) was added thereto, followed by stirring for 4 days at 70° C. Subsequently, water was added thereto, and the resultant mixture was extracted with ethyl acetate. The organic layer was washed with brine, and the resultant mixture was subjected to drying over anhydrous sodium sulfate, concentration under reduced pressure, and purification by silica gel chromatography (chloroform/methanol=50/1), whereby the target compound was obtained (7.4 g, 44%).

Production Example 11

Synthesis of tert-Butyl 2-[2-[3-[N-2-(4-chlorophenoxy)ethyl]aminopropyl]phenoxy]-2-methylpropionate

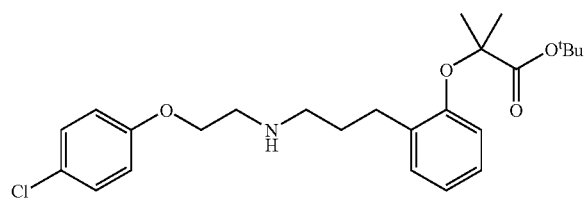

tert-Butyl 2-[2-[2-[2-(4-chlorophenoxy)ethylaminocarbonyl]ethyl]phenoxy]-2-methylpropionate (7.4 g, 16.0 mmol) was dissolved in tetrahydrofuran (5.0 mL). Subsequently, a 1.0M borane-tetrahydrofuran complex in tetrahydrofuran solution (32.0 mL, 32.0 mmol) was added dropwise at room temperature, and the mixture was stirred for three hours at 50° C. Concentrated hydrochloric acid was added under ice-cooling, and the mixture was stirred for three hours at room temperature. Aqueous 80% ethylamine solution was added dropwise under ice-cooling, and the mixture was extracted with ethyl acetate. The organic layer was washed with brine, followed by drying over anhydrous sodium sulfate, concentration under reduced pressure, and purification by silica gel chromatography (chloroform/methanol=50/1), whereby the target compound was obtained (3.9 g, 54%).

$^1$H-NMR (400 MHz, CDCl$_3$) δ 1.40 (s, 9H), 1.58 (s, 6H), 1.83 (quintet, J=7 Hz, 2H), 2.67 (t, J=8 Hz, 2H), 2.70 (t, J=7 Hz, 2H), 2.99 (t, J=5 Hz, 2H), 4.03 (t, J=5 Hz, 2H), 6.68 (d, J=8 Hz, 1H), 6.82 (t, J=9 Hz, 2H), 6.84–6.88 (m, 1H), 7.05 (t, J=8 Hz, 1H), 7.12 (d, J=8 Hz, 1H), 7.22 (d, J=9 Hz, 2H).

Production Example 12

Synthesis of tert-Butyl 2-[2-[3-[N-(benzoxazol-2-yl)-N-2-(4-chlorophenoxy)ethyl]aminopropyl]phenoxy]-2-methylpropionate

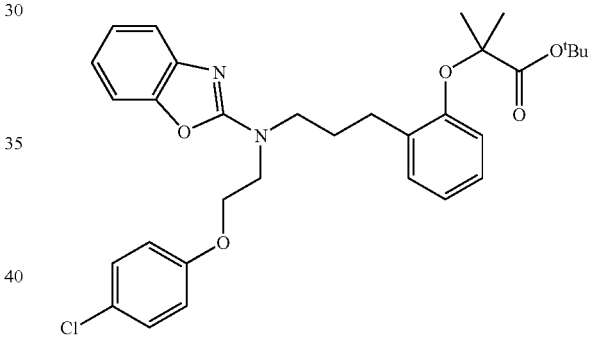

tert-Butyl 2-[2-[3-[N-2-(4-chlorophenoxy)ethyl]aminopropyl]phenoxy]-2-methylpropionate (3.9 g, 8.71 mmol) was dissolved in DMF (5.0 mL), and diisopropylethylamine (1.4 g, 10.5 mmol) was added dropwise thereto. Subsequently, 2-chlorobenzoxazole (1.6 g, 10.5 mmol) was added dropwise thereto, and the mixture was stirred overnight at 70° C. Subsequently, water was added thereto, and the mixture was extracted with ethyl acetate. The organic layer was washed with brine, followed by drying over anhydrous sodium sulfate. The dried mixture was subjected to concentration under reduced pressure, and purification by silica gel chromatography (n-hexane/ethyl acetate=4/1), whereby the target compound was obtained (4.5 g, 90%).

$^1$H-NMR (400 MHz, CDCl$_3$) δ 1.37 (s, 9H), 1.57 (s, 6H), 2.02–2.10 (m, 2H), 2.71 (t, J=8 Hz, 2H), 3.70 (t, J=8 Hz, 2H), 3.93 (t, J=6 Hz, 2H), 4.22 (t, J=5 Hz, 2H), 6.68 (d, J=8 Hz, 1H), 6.78 (t, J=9 Hz, 2H), 6.87 (t, J=8 Hz, 1H), 7.00 (t, J=8 Hz, 1H), 7.04–7.22 (m, 3H), 7.20 (d, J=9 Hz, 2H), 7.23 (d, J=8 Hz, 1H), 7.35 (d, J=8 Hz, 1H).

Example 74

Synthesis of 2-[2-[3-[N-(Benzoxazol-2-yl)-N-2-(4-chlorophenoxy)ethyl]aminopropyl]phenoxy]-2-methylpropionic acid

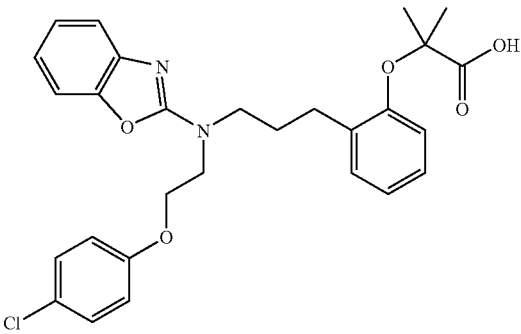

tert-Butyl 2-[2-[3-[N-(benzoxazol-2-yl)-N-2-(4-chlorophenoxy)ethyl]aminopropyl]phenoxy]-2-methylpropionate (4.5 g, 7.87 mmol) was dissolved in methylene chloride (10.0 mL). Subsequently, 50%-trifluoroacetic acid/methylene chloride solution (6.8 g) was added dropwise thereto, and the mixture was stirred for three hours at room temperature. The resultant mixture was subjected to concentration under reduced pressure, toluene azeotrope, and purification by silica gel chromatography (chloroform/methanol=50/1), whereby the target compound was obtained (3.3 g, 83%).

$^1$H-NMR (400 MHz, CDCl$_3$) δ 1.61 (s, 6H), 1.94–2.14 (br, 2H), 2.69 (t, J=8 Hz, 2H), 3.64 (t, J=8 Hz, 2H), 3.85 (t, J=5 Hz, 2H), 4.09 (t, 5 Hz, 2H), 6.70 (d, J=9 Hz, 2H), 6.81 (d, J=8 Hz, 1H), 6.89 (t, J=7 Hz, 1H), 7.00 (t, J=7 Hz, 1H), 7.10–7.19 (m, 3H), 7.16 (d, J=9 Hz, 2H), 7.21 (d, J=8 Hz, 1H), 7.35 (d, J=8 Hz, 1H).

Sodium 2-[2-[3-[N-(benzoxazol-2-yl)-N-2-(4-chlorophenoxy)ethyl]aminopropyl]phenoxy]-2-methylpropionate

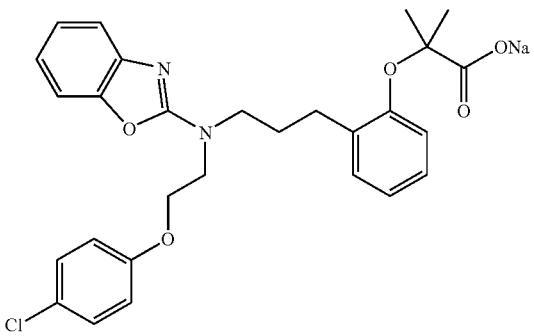

2-[2-[3-[N-(Benzoxazol-2-yl)-N-2-(4-chlorophenoxy)ethyl]aminopropyl]phenoxy]-2-methylpropionic acid (3.2 g, 6.28 mmol) was dissolved in methanol. A solution of NaOMe (340 mg, 6.28 mmol) in methanol was added thereto at room temperature, and then the resultant mixture was stirred for 1 hour. Subsequently, the reaction mixture was subjected to concentration under reduced pressure, and n-hexane was added to the resultant concentrate. The thus-obtained solid was purified, whereby a white amorphous powder was obtained (2.7 g, 81%).

$^1$H-NMR (400 MHz, CDCl$_3$) δ 1.35 (s, 6H), 1.80–2.00 (br, 2H), 2.48–2.60 (br, 2H), 3.45–3.60 (br, 2H), 3.80 (br s, 2H), 4.05–4.13 (br, 2H), 6.70 (d, J=9 Hz, 2H), 6.75–6.80 (m, 2H), 6.87–7.01 (m, 3H), 7.08 (t, J=8 Hz, 1H), 7.13–7.18 (m, 1H), 7.14 (d, J=9 Hz, 2H), 7.28 (t, J=8 Hz, 1H) MS (FAB) m/z: 533[(M$^+$+1)+2], 531 (M$^+$+1).

In a manner similar to that described in Example 74, the compound of Examples 75 was synthesized.

Example 75

Synthesis of 2-[2-[3-[N-(Benzoxazol-2-yl)-N-2-phenoxyethyl]aminopropyl]phenoxy]-2-methylpropionic acid

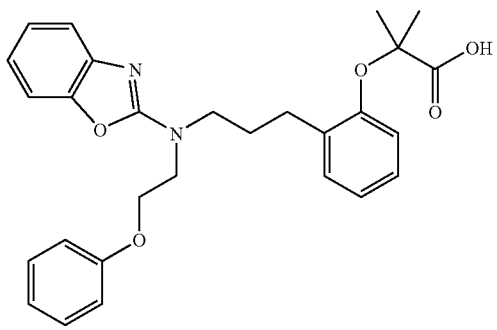

MS (m/z) 474 (M$^+$).

Production Example 13

Synthesis of tert-Butyl 2-[4-(cyanomethyl)phenoxy]-2-methylpropionate

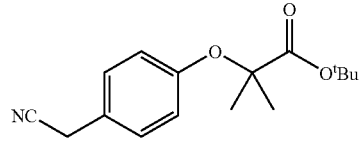

4-Hydroxyphenylacetonitrile (13.3 g, 100 mmol) and potassium carbonate (20.73 g, 150 mmol) were added to dimethylformamide (75 mL). Subsequently, tert-butyl 2-bromoisobutyrate (50.41 mL, 250 mmol) was added thereto, and the mixture was stirred for 24 hours at 80° C. The temperature of the reaction mixture was returned to room temperature, and ethyl acetate was added thereto. Washing was performed sequentially with water and brine, followed by drying over sodium sulfate. The resultant mixture was subjected to concentration under reduced pressure and purification by silica gel column chromatography (n-hexane/ethyl acetate=7/1), whereby the target compound was obtained (18.62 g, 67.62 mmol, 67.6%).

Production Example 14

Synthesis of tert-Butyl 2-[4-(2-aminoethyl)phenoxy]-2-methylpropionate

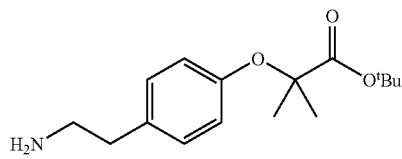

tert-Butyl 2-[4-(cyanomethyl)phenoxy]-2-methylpropionate (5.50 g, 20.0 mmol) was dissolved in tetrahydrofuran (90 mL). Subsequently, in a nitrogen atmosphere, borane-tetrahydrofuran complex in tetrahydrofuran solution [1.08M BH$_3$-THF in THF (92.6 mL, 100 mmol)] was added thereto, and the mixture was stirred for three hours at 50° C. Subsequently, 1M hydrochloric acid was gradually added at 0° C., and the resultant mixture was stirred for one hour at room temperature. Thereafter, the reaction mixture was made basic with sodium carbonate. Tetrahydrofuran was evaporated, and then chloroform was added. Washing was performed sequentially with water and brine, followed by drying over sodium sulfate. The reaction mixture was subjected to concentration under reduced pressure and purification by silica gel column chromatography (chloroform/methanol=10/1), whereby the target compound was obtained (5.16 g, 13.02 mmol, 65.1%).

$^1$H NMR (400 MHz, CDCl$_3$) δ1.44 (s, 9H), 1.54 (s, 6H), 2.67 (t, J=7 Hz, 2H), 2.92 (t, J=7 Hz, 2H), 6.86 (m, 2H), 7.09 (m, 2H,).

Production Example 15

Synthesis of tert-Butyl 2-[4-[2-N-(benzoxazol-2-yl) aminoethyl]phenoxy]-2-methylpropionate

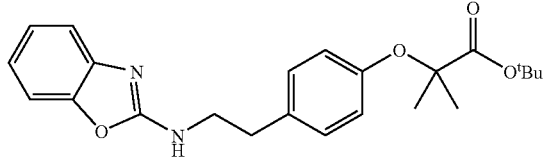

tert-Butyl 2-[4-(2-aminoethyl)phenoxy]-2-methylpropionate (290 mg, 1.04 mmol) was dissolved in tetrahydrofuran (4 mL). Subsequently, diisopropylethylamine (272 μL, 1.56 mmol), and then 2-chlorobenzoxazole (145 μL, 1.25 mmol) were added thereto, and the mixture was stirred under argon atmosphere for 15 hours at room temperature. Ethyl acetate was added to the reaction mixture. Washing was performed sequentially with water and brine, followed by drying over sodium sulfate. The reaction mixture was subjected to filtration, concentration under reduced pressure, and separation by silica gel column chromatography (n-hexane/ethyl acetate=10/1), whereby the target compound was obtained (367 mg, 0.925 mmol, 88.9%).

Production Example 16

Synthesis of tert-Butyl 2-[4-[2-[N-(benzoxazol-2-yl)-N-2-(4-chlorophenoxy)ethyl]aminoethyl]phenoxy]-2-methylpropionate

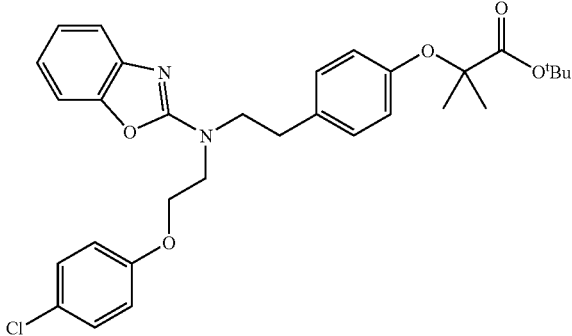

tert-Butyl 2-[4-[2-N-(benzoxazol-2-yl)aminoethyl]phenoxy]-2-methylpropionate (50 mg, 0.126 mmol) was dissolved in acetonitrile (3 mL). Subsequently, cesium carbonate (62 mg, 0.189 mmol) and 2-(4-chlorophenoxy)-1-bromoethane (59 mg, 0.252 mmol) were added thereto, and the mixture was stirred for 14 hours at 70° C. The temperature of the mixture was returned to room temperature, and ethyl acetate was added. The resultant mixture was sequentially washed with water and brine, followed by drying over sodium sulfate. The mixture was subjected to concentration under reduced pressure and purification by preparative TLC (silica gel, n-hexane/ethyl acetate=10/1), whereby the target compound was obtained (26 mg, 0.0474 mmol, 37.6%).

Examples 76

Synthesis of 2-[4-[2-[N-(Benzoxazol-2-yl)-N-2-(4-chlorophenoxy)ethyl]aminoethyl]phenoxy]-2-methylpropionic acid

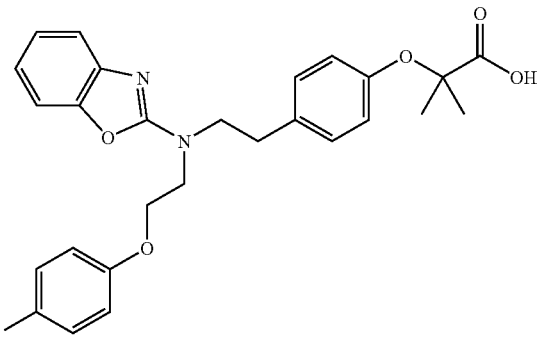

tert-Butyl 2-[4-[2-[N-(benzoxazol-2-yl)-N-2-(4-chlorophenoxy)ethyl]aminoethyl]phenoxy]-2-methylpropionate (26 mg, 0.0474 mmol) was dissolved in dichloromethane (6 mL). Subsequently, trifluoroacetic acid (0.5 mL) was added thereto, and the mixture was stirred for 5 hours at room temperature. The mixture was subjected to concentration under reduced pressure and toluene azeotrope. Thereafter, chloroform was added thereto, and the mixture was sequentially washed with water and brine, followed by drying over sodium sulfate. The resultant mixture was subjected to concentration under reduced pressure and purification by preparative TLC (silica gel, chloroform/methanol=10/1), whereby the target compound was obtained (23 mg, 0.0467 mmol, 98.5%).

MS (FAB) m/z: 495 (M$^+$+1).

In a manner similar to that described in Example 76, the compounds of Examples 77 through 79 were synthesized.

Example 77

Synthesis of 2-[4-[2-[N-(Benzoxazol-2-yl)-N-2-phenoxyethyl]aminoethyl]phenoxy]-2-methylpropionic acid

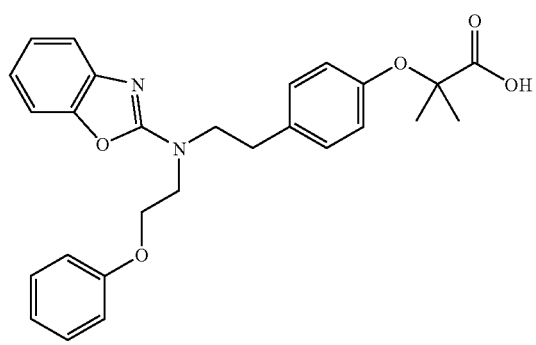

MS (m/z) 460 (M$^+$).

Example 78

Synthesis of 2-[3-[2-[N-(Benzoxazol-2-yl)-N-2-phenoxyethyl]aminoethyl]phenoxy]-2-methylpropionic acid

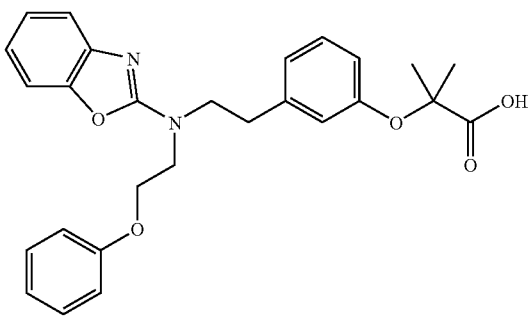

MS (m/z) 460 (M+).

Example 79

Synthesis of 2-[3-[2-[N-(Benzoxazol-2-yl)-N-2-(4-chlorophenoxy)ethyl]aminoethyl]phenoxy]-2-methylpropionic acid

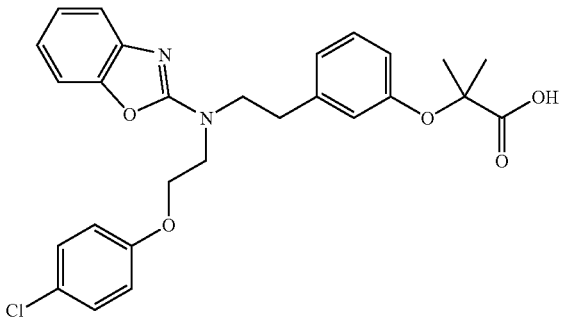

MS (FAB) m/z: 495 (M++1), 497[(M++1)+2].

Production Example 17

Synthesis of 2-Methoxyphenylacetamide

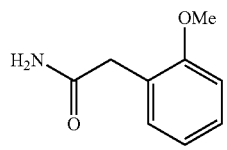

2-Methoxyphenylacetic acid (10.0 g, 60.1 mmol) was dissolved in acetonitrile (15 mL). Subsequently, pyridine (2.84 g, 36.1 mmol) and di-tert-butyl dicarbonate [Boc$_2$O (19.6 g, 90.2 mmol)] were added thereto. The mixture was stirred for 10 minutes at room temperature, and then ammonium hydrogencarbonate (7.1 g, 90.2 mmol) were added. After completion of reaction, the reaction mixture was concentrated under reduced pressure. Thereafter, the resultant concentrate was added to water, and the resultant mixture was extracted with chloroform, followed by washing sequentially with 1M hydrochloric acid and brine. The resultant mixture was subjected to drying over magnesium sulfate and concentration under reduced pressure. The resultant concentrate was used in Production Example 18 without purification.

Production Example 18

Synthesis of 2-Hydroxyphenylacetamide

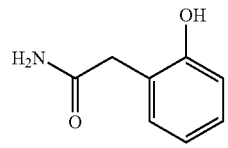

2-Methoxyphenyl acetamide (13.0 g, 78.6 mmol) was dissolved in methylene chloride (10.0 mL). Subsequently, 1.0M boron tribromide in methylene chloride solution (157 mL, 157 mmol) was slowly added dropwise under ice-cooling, and the mixture was stirred for one hour at room temperature. Subsequently, water was slowly added thereto under ice-cooling, and the mixture was stirred for 30 minutes. The mixture was extracted with chloroform, followed by washing the organic layer with brine, drying over anhydrous sodium sulfate. The reaction mixture was subjected to concentration under reduced pressure and purification by column chromatography (n-hexane/ethyl acetate=20/1), whereby a white solid was obtained (1.8 g, 11.9 mmol, 15%).

Production Example 19

Synthesis of tert-Butyl 2-[2-(aminocarbonylmethyl)phenoxy]-2-methylpropionate

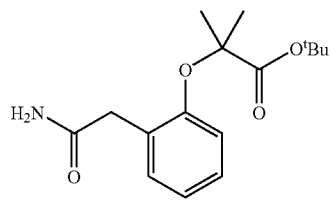

2-Hydroxyphenyl acetamide (1.2 g, 7.93 mmol) was dissolved in acetonitrile (10 mL), and potassium carbonate (5.5 g, 39.6 mmol) was added to the solution. Subsequently, to the mixture, tert-butyl 2-bromoisobutyrate (8.9 g, 39.6 mmol) was added, followed by stirring at 80° C. After completion of reaction, water was added to the mixture. The resultant mixture was extracted with ethyl acetate, followed by washing the organic layer with water. The mixture was subjected to drying over sodium sulfate, concentration under reduced pressure, and purification by silica gel chromatography (chloroform/methanol=40/1), whereby the target compound was obtained (1.4 g, 4.87 mmol, 61%).

$^1$H-NMR (400 MHz, CDCl$_3$) δ 1.43 (s, 9H), 1.65 (s, 6H), 3.59 (s, 2H), 6.10–6.35 (br, 2H), 6.75 (d, J=8 Hz, 1H), 6.94 (t, J=7 Hz, 1H), 7.17 (t, J=8 Hz, 1H), 7.25 (d, J=7 Hz, 1H).

Production Example 20

Synthesis of tert-Butyl 2-[2-(2-aminoethyl)phenoxy]-2-methylpropionate

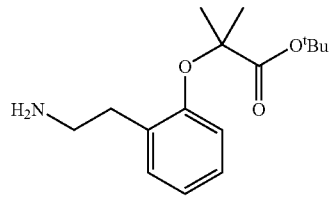

tert-Butyl 2-[2-(aminocarbonylmethyl)phenoxy]-2-methylpropionate (1.4 g, 4.87 mmol) was dissolved in tetrahydrofuran (5.0 mL). Subsequently, under nitrogen atmosphere, borane-THF complex in THF solution [1.0M $BH_3$-THF in THF (14.6 mL, 14.6 mmol)] was added thereto, the mixture was stirred for three hours at 50° C. Thereafter, concentrated hydrochloric acid was gradually added thereto at 0° C. The resultant mixture was stirred for one hour at room temperature and made basic with an aqueous ethylamine solution. Ethyl acetate was added thereto. The mixture was sequentially washed with water and brine, followed by drying over sodium sulfate. The mixture was subjected to concentration under reduced pressure and purification by silica gel column chromatography (chloroform/methanol=30/1), whereby the target compound was obtained (830 mg, 2.97 mmol, 61%).

$^1$H-NMR (400 MHz, $CDCl_3$) δ 1.43 (s, 9H), 1.65 (s, 6H), 2.09 (br s., 2H), 2.79 (t, J=7 Hz, 2H), 2.97 (t, J=7 Hz, 2H), 6.69 (d, J=8 Hz, 1H), 6.88 (t, J=7 Hz, 1H), 7.07 (d, J=8 Hz, 1H), 7.14 (d, J=7 Hz, 1H).

Production Example 21

Synthesis of tert-Butyl 2-[2-[2-N-(benzoxazol-2-yl)aminoethyl]phenoxy]-2-methylpropionate

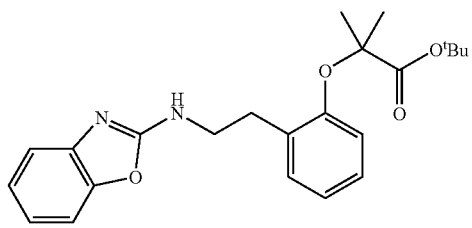

tert-Butyl 2-[2-(2-aminoethyl)phenoxy]-2-methylpropionate (762 mg, 2.73 mmol) was dissolved in tetrahydrofuran (5.0 mL). Subsequently, diisopropylethylamine (422.6 mg, 3.27 mmol), and then 2-chlorobenzoxazole (502.4 mg, 3.27 mmol) were added thereto, and the mixture was stirred overnight at room temperature. Ethyl acetate was added to the reaction mixture. Washing was performed sequentially with water and brine, followed by drying over sodium sulfate. Thereafter, the reaction mixture was subjected to filtration, concentration under reduced pressure, and purification by silica gel column chromatography (n-hexane/ethyl acetate=6/1), whereby the target compound was obtained (977 mg, 2.46 mmol, 90%).

Production Example 22

Synthesis of tert-Butyl 2-[2-[2-[N-(benzoxazol-2-yl)-N-2-phenoxyethyl]aminoethyl]phenoxy]-2-methylpropionate

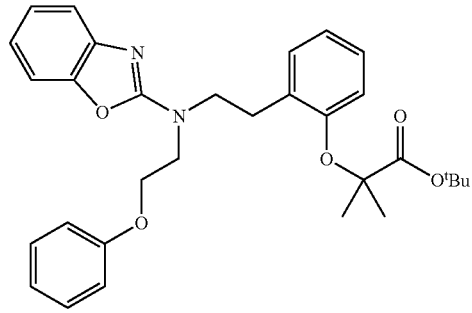

tert-Butyl 2-[2-[2-(N-benzoxazol-2-yl)aminoethyl]phenoxy]-2-methylpropionate (157 mg, 0.40 mmol) was dissolved in acetonitrile (3.0 mL). Subsequently, cesium carbonate (282 mg, 0.87 mmol) and 2-phenoxyethyl bromide (160 mg, 0.80 mmol) were added thereto, and the mixture was stirred overnight at 80° C. The temperature of the reaction mixture was returned to room temperature, and ethyl acetate was added. Washing was performed sequentially with water and brine, followed by drying over sodium sulfate. The reaction mixture was subjected to concentration under reduced pressure and purification by silica gel column chromatography (n-hexane/ethyl acetate=4/1), whereby the target compound was obtained (85.3 mg, 0.17 mmol, 41%).

Production Example 80

Synthesis of 2-[2-[2-[N-(Benzoxazol-2-yl)-N-2-phenoxyethyl]aminoethyl]phenoxy]-2-methylpropionic acid

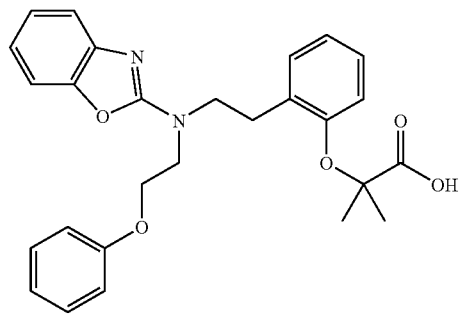

tert-Butyl 2-[2-[2-[N-(benzoxazol-2-yl)-N-2-phenoxyethyl]aminoethyl]phenoxy]-2-methylpropionate (85.3 mg, 0.17 mmol) was dissolved in methylene chloride (3.0 mL). Subsequently, 50% trifluoroacetic acid in methylene chloride solution was added thereto, and the mixture was stirred for three hours at room temperature. The resultant mixture was subjected to concentration under reduced pressure and toluene azeotrope. Chloroform was added to the resultant mixture, and washing was performed sequentially with water and brine, followed by drying over sodium sulfate, concentration under reduced pressure, and purification by preparative TLC (silica gel, chloroform/methanol=20/1), whereby the target compound was obtained (63.5 mg, 0.14 mmol, 81%).

MS (m/z) 460 ($M^+$).

In a manner similar to that described in Example 80, the compound of Example 81 was synthesized.

Production Example 81

Synthesis of 2-[2-[2-[N-(Benzoxazol-2-yl)-N-2-(4-chlorophenoxy)ethyl]aminoethyl]phenoxy]-2-methylpropionic acid

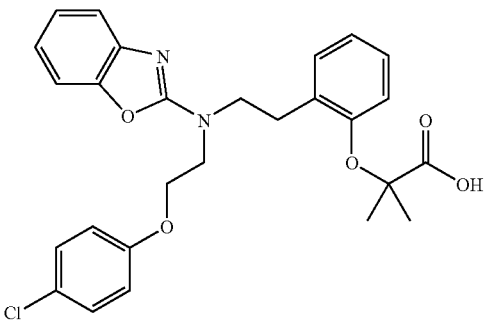

MS (m/z) 494 (M⁺), 496 (M⁺+2).

Production Example 23

Synthesis of 3-tert-Butyldimethylsilyloxybenzaldehyde

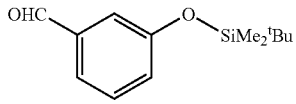

3-Hydroxybenzaldehyde (5.0 g, 40.9 mmol) was dissolved in acetonitrile (10.0 mL). Subsequently, potassium carbonate (11.3 g, 81.9 mmol), and then tert-butyldimethylchlorosilane (7.4 g, 49.1 mmol) were added thereto, and the resultant mixture was stirred at room temperature. After completion of reaction, ethyl acetate was added thereto, followed by washing sequentially with water and brine, and drying over anhydrous sodium sulfate. The reaction mixture was subjected to filtration, concentration under reduced pressure, and purification by silica gel column chromatography (n-hexane/ethyl acetate=20/1), whereby the target compound was obtained (9.1 g, 94%).

¹H-NMR (400 MHz, CDCl₃) δ 0.00 (s, 6H), 0.77 (s, 9H), 6.88 (d, J=8 Hz, 1H), 7.10 (s, 1H), 7.18 (t, J=8 Hz, 1H), 7.25 (d, J=8 Hz, 1H), 9.73 (s, 1H).

Production Example 24

Synthesis of N-3-(4-Methoxyphenoxy)propyl-3-tert-butyldimethylsilyloxybenzylamine

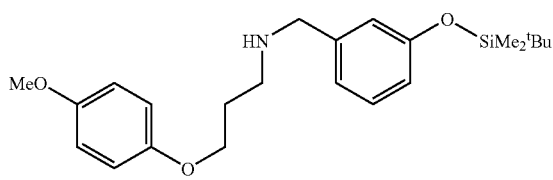

3-tert-Butyldimethylsilyloxybenzaldehyde (1.5 g, 6.34 mmol) was dissolved in 1,2-dichloroethane (10.0 mL). Subsequently, 3-(4-methoxyphenoxy)propylamine (1.5 g, 8.25 mmol) was added thereto, and the resultant mixture was stirred for 20 minutes. At room temperature, sodium triacetoxyborohydride (1.75 g, 8.25 mmol) and acetic acid (495 mg, 8.25 mmol) were added thereto, and the mixture was stirred overnight. A saturated aqueous sodium hydrogencarbonate solution was added thereto. The reaction mixture was extracted with chloroform, and the organic layer was washed with brine. The resultant mixture was subjected to drying over anhydrous sodium sulfate, concentration under reduced pressure, and purification by silica gel chromatography (chloroform/methanol=50/1), whereby the target compound was obtained (1.9 g, 78%).

¹H-NMR (400 MHz, CDCl₃) δ 0.00 (s, 6H), 0.73 (s, 9H), 1.81 (m, 2H), 2.66 (br. s, 2H), 3.58 (s, 3H), 3.61 (s, 2H), 3.81 (t, J=6 Hz, 2H), 6.55 (d, J=7 Hz, 1H), 6.63 (br. s, 5H), 6.73 (d, J=7 Hz, 1H), 6.99 (t, J=7 Hz, 1H).

Production Example 25

Synthesis of N-(Benzoxazol-2-yl)-N-3-(4-methoxyphenoxy)propyl-3-tert-butyldimethylsilyloxybenzylamine

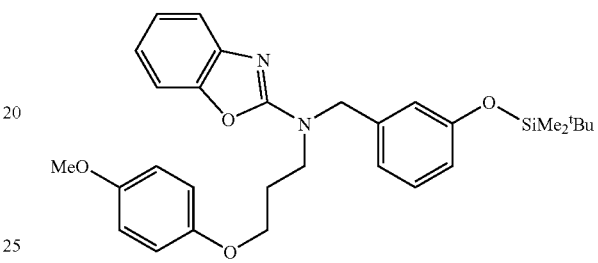

N-3-(4-methoxyphenoxy)propyl-3-tert-butyldimethylsilyloxybenzylamine (1.9 g, 5.0 mmol) was dissolved in N,N-dimethylformamide (3.0 mL). Subsequently, N,N-diisopropylethylamine (768 mg, 5.9 mmol) was added dropwise thereto. To the solution, 2-chlorobenzoxazole (912 mg, 5.94 mmol) was added. The mixture was stirred for 15 minutes at room temperature, and then stirred overnight at 70° C. The resultant mixture was extracted with ethyl acetate, followed by washing the organic layer with brine, drying over anhydrous sodium sulfate, and concentration under reduced pressure. The resultant mixture was subjected to purification by silica gel column chromatography (n-hexane/ethyl acetate=10/1), whereby the target compound was obtained (1.9 g, 73%).

¹H NMR (400 MHz, CDCl₃) δ 0.05 (s, 9H), 0.85 (s, 6H), 2.04 (m, 2H), 3.60 (t, J=7 Hz, 2H), 3.67 (s, 3H), 3.87 (t, J=6 Hz, 2H), 4.63 (s, 2H), 6.65–6.80 (m, 7H), 6.91 (t, J=7 Hz, 1H), 7.05–7.09 (m, 2H), 7.12 (d, J=8 Hz, 1H), 7.27 (d, J=8 Hz, 1H).

Production Example 26

Synthesis of N-(Benzoxazol-2-yl)-N-3-(4-methoxyphenoxy)propyl-3-hydroxybenzylamine

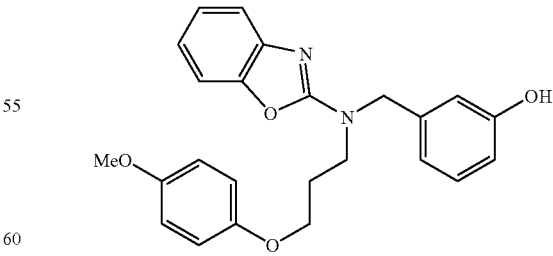

N-(Benzoxazol-2-yl)-N-3-(4-methoxyphenoxy)propyl-3-tert-butyldimethylsilyloxybenzylamine (1.9 g, 3.6 mmol) was dissolved in solvent mixture of N,N-dimethylformamide/H₂O (10/1) (5.0 mL). Subsequently, cesium carbonate (1.2 g, 3.6 mmol) was added thereto. The mixture was stirred for 3 hours at room temperature, followed by concentration under reduced pressure. Hydrochloric acid (1.0 mol/L) was added thereto. The resultant mixture was extracted with ethyl acetate, followed by washing the organic layer with brine, drying over anhydrous sodium sulfate, and concentration under reduced pressure. The resultant mixture was subjected to purification by silica gel chromatography (n-hexane/ethyl acetate=5/1), whereby the target compound was obtained (1.3 g, 89%).

$^1$H-NMR (400 MHz, CDCl$_3$) δ 1.98 (quintet, J=7 Hz, 2H), 3.37 (t, J=7 Hz, 2H), 3.75 (s, 3H), 3.86 (t, J=6 Hz, 2H), 4.61 (s, 2H), 6.65–6.81 (m, 7H), 6.90–7.13 (m, 5H).

Production Example 27

Synthesis of Ethyl (R)-2-[3-[[N-(benzoxazol-2-yl)-N-3-(4-methoxyphenoxy)propyl]aminomethyl]phenoxy]propionate

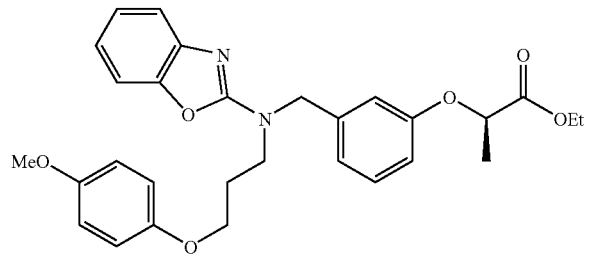

N-(Benzoxazol-2-yl)-N-3-(4-methoxyphenoxy)propyl-3-hydroxybenzylamine (244 mg, 0.6 mmol) was dissolved in toluene (5.0 mL). Subsequently, (S)-ethyl lactate (78.4 mg, 0.66 mmol) and triphenylphosphine (174 mg, 0.66 mmol) were added thereto. Under argon atmosphere, a 40% diethylazodicarboxylate in toluene solution (289 mL, 0.66 mmol) was slowly added thereto at 0° C., and the mixture was stirred at room temperature. After completion of reaction, the resultant mixture was subjected to concentration under reduced pressure, followed by addition of water, extraction with ethyl acetate, and washing the organic layer with brine. The mixture was dried over anhydrous sodium sulfate, followed by concentration under reduced pressure and purification by silica gel chromatography (n-hexane/ethyl acetate=9/1), whereby the target compound was obtained (180 mg, 60%).

$^1$H-NMR (400 MHz, CDCl$_3$) δ 1.16 (t, J=7 Hz, 3H), 1.56 (d, J=7 Hz, 3H), 2.12 (quintet, J=7 Hz, 2H), 3.67 (t, J=7 Hz, 2H), 3.74 (s, 3H), 3.94 (t, J=6 Hz, 2H), 4.07–4.18 (m, 2H), 4.68 (q, J=7 Hz, 1H), 4.72 (s, 2H), 6.75 (d, J=8 Hz, 1H), 6.79 (s, 4H), 6.83 (br. s, 1H), 6.88 (d, J=8 Hz, 1H), 6.99 (t, J=8 Hz, 1H), 7.14 (t, J=8 Hz, 1H), 7.18–7.22 (m, 2H), 7.35 (d, J=8 Hz, 1H).

Example 82

Synthesis of (R)-2-[3-[[N-(Benzoxazol-2-yl)-N-3-(4-methoxyphenoxy)propyl]aminomethyl]phenoxy] propionic acid

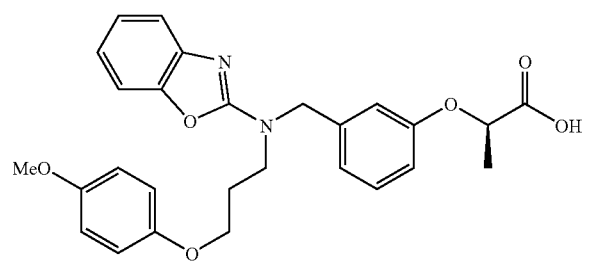

Ethyl (R)-2-[3-[[N-(benzoxazol-2-yl)-N-(3-(4-methoxyphenoxy)propyl)aminomethyl]phenoxy]propionate (180 mg, 0.36 mmol) was dissolved in solvent mixture of tetrahydrofuran/H$_2$O (6/1) (4.0 mL). Subsequently, lithium hydroxide.H$_2$O (25.9 mg, 0.43 mmol) was added thereto, and the mixture was stirred for one hour at 0° C. Under ice-cooling, the resultant mixture was acidified with aqueous 1M HCl solution, and then subjected to extraction with ethyl acetate and sequentially washing with water and brine. The mixture was dried over sodium sulfate, followed by concentration under reduced pressure and purification by silica gel column chromatography (chloroform/methanol=10/1), whereby the target compound was obtained (112 mg, 65%).

$^1$H NMR (400 MHz, CDCl$_3$) δ 1.40 (br s, 3H), 2.01 (m, 2H), 3.58 (t, J=7 Hz, 2H), 3.70 (s, 3H), 3.84 (t, J=6 Hz, 2H), 4.55 (br s, 1H), 4.59 (s, 2H), 6.70–6.81 (m, 7H), 6.93 (t, J=8 Hz, 1H), 7.03–7.14 (m, 3H), 7.31 (d, J=8 Hz, 1H).

Also, the compounds shown in Tables 1 to 7 below have been synthesized.

TABLE 1

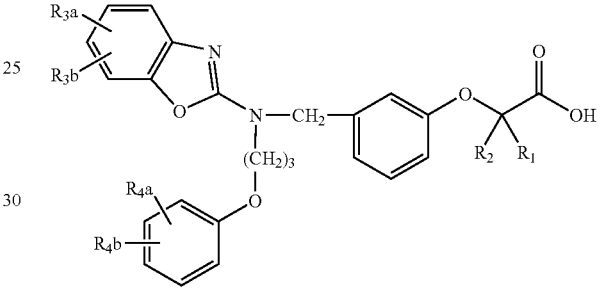

| Examples | R$_1$ | R$_2$ | R$_{3a}$ | R$_{3b}$ | R$_{4a}$ | R$_{4b}$ |
|---|---|---|---|---|---|---|
| 83 | Me | H | 5-MeSO$_3$ | H | H | H |
| 84 | Et | H | 5-MeSO$_3$ | H | H | H |
| 85 | Me | H | 5-MeSO$_2$ | H | H | H |
| 86 | Et | H | 5-MeSO$_2$ | H | H | H |
| 87 | Me | H | H | H | 4-MeSO$_2$ | H |
| 88 | Et | H | H | H | 4-MeSO$_2$ | H |
| 89 | Me | Me | 5-F | H | H | H |
| 90 | Me | Me | 5-Cl | H | H | H |
| 91 | Me | Me | 5-MeO | H | H | H |
| 92 | Me | Me | H | H | 4-F | H |
| 93 | Me | Me | 5-F | H | 4-F | H |
| 94 | Me | Me | 5-Cl | H | 4-F | H |
| 95 | Me | Me | 5-MeO | H | 4-F | H |
| 96 | Et | H | 4-F | H | H | H |
| 97 | Me | H | 4-F | H | H | H |
| 98 | Et | H | 5-F | H | H | H |
| 99 | Me | H | 5-F | H | H | H |

TABLE 2

| Examples | R$_1$ | R$_2$ | R$_{3a}$ | R$_{3b}$ | R$_{4a}$ | R$_{4b}$ |
|---|---|---|---|---|---|---|
| 100 | Et | H | 6-F | H | H | H |
| 101 | Me | H | 6-F | H | H | H |
| 102 | Et | H | 7-F | H | H | H |
| 103 | Me | H | 7-F | H | H | H |
| 104 | Et | H | 4-F | H | 4-F | H |
| 105 | Me | H | 4-F | H | 4-F | H |
| 106 | Et | H | 5-F | H | 4-F | H |
| 107 | Me | H | 5-F | H | 4-F | H |
| 108 | Et | H | 6-F | H | 4-F | H |
| 109 | Me | H | 6-F | H | 4-F | H |
| 110 | Et | H | 7-F | H | 4-F | H |
| 111 | Me | H | 7-F | H | 4-F | H |
| 112 | Et | H | 4-F | 6-F | H | H |
| 113 | Me | H | 4-F | 6-F | H | H |

TABLE 2-continued

| Examples | R₁ | R₂ | R₃ₐ | R₃ᵦ | R₄ₐ | R₄ᵦ |
|---|---|---|---|---|---|---|
| 114 | Et | H | H | H | 3-NO₂ | H |
| 115 | Me | H | H | H | 3-NO₂ | H |
| 116 | Et | H | H | H | 4-Me | H |
| 117 | Me | H | H | H | 4-Me | H |
| 118 | Et | H | 5-CF₃ | H | 4-F | H |
| 119 | Me | H | 5-CF₃ | H | 4-F | H |
| 120 | Et | H | 5-CF₃ | H | H | H |
| 121 | Me | H | 5-CF₃ | H | H | H |
| 122 | Et | H | 5-CH₃ | H | 4-F | H |
| 123 | Me | H | 5-CH₃ | H | 4-F | H |
| 124 | Et | H | 5-CH₃ | H | H | H |

TABLE 3

| Examples | R₁ | R₂ | R₃ₐ | R₃ᵦ | R₄ₐ | R₄ᵦ |
|---|---|---|---|---|---|---|
| 125 | Me | H | 5-CH₃ | H | H | H |
| 126 | Et | H | H | H | 3,4-OCH₂O | |
| 127 | Me | H | H | H | 3,4-OCH₂O | |
| 128 | Et | H | 5,6-OCH₂O | | H | H |
| 129 | Me | H | 5,6-OCH₂O | | H | H |
| 130 | Et | H | H | H | 2-Me | 4-Me |
| 131 | Me | H | H | H | 2-Me | 4-Me |
| 132 | Et | H | H | H | 3-Me | 4-Me |
| 133 | Me | H | H | H | 3-Me | 4-Me |
| 134 | Et | H | H | H | 2-F | 4-F |
| 135 | Me | H | H | H | 2-F | 4-F |
| 136 | Et | H | H | H | 3-F | 4-F |
| 137 | Me | H | H | H | 3-F | 4-F |

TABLE 4

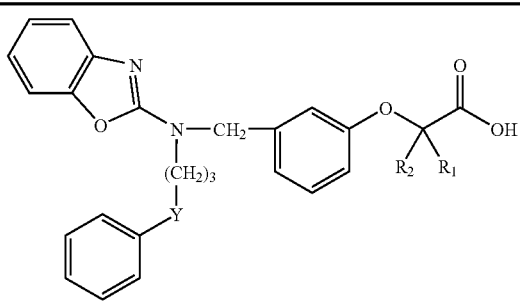

| Examples | R₁ | R₂ | Y |
|---|---|---|---|
| 138 | Et | H | S |
| 139 | Me | H | S |
| 140 | Et | H | SO |
| 141 | Me | H | SO |
| 142 | Et | H | SO₂ |
| 143 | Me | H | SO₂ |
| 144 | Et | H | CO |
| 145 | Me | H | CO |
| 146 | Et | H | CONH |
| 147 | Me | H | CONH |
| 148 | Et | H | NHCO |
| 149 | Me | H | NHCO |
| 150 | Et | H | SO₂NH |
| 151 | Me | H | SO₂NH |
| 152 | Et | H | NHSO₂ |
| 153 | Me | H | NHSO₂ |
| 154 | Et | H | NH |
| 155 | Me | H | NH |

TABLE 4-continued

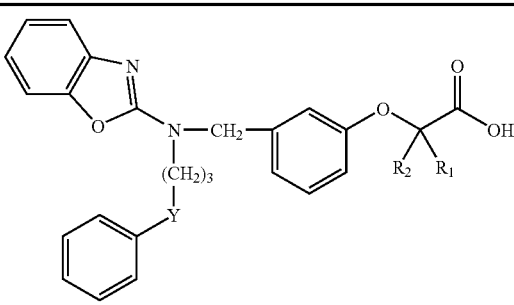

| Examples | R₁ | R₂ | Y |
|---|---|---|---|
| 156 | Et | H | NMe |
| 157 | Me | H | NMe |

TABLE 5

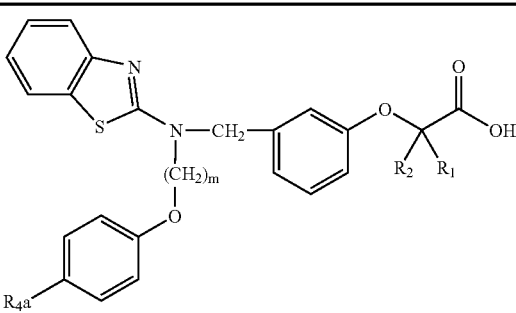

| Exampls | R₁ | R₂ | R₄ₐ | m |
|---|---|---|---|---|
| 158 | Et | H | H | 2 |
| 159 | Et | H | F | 2 |
| 160 | Et | H | Cl | 2 |
| 161 | Et | H | MeO | 2 |
| 162 | Me | H | H | 2 |
| 163 | Me | H | F | 2 |
| 164 | Me | H | Cl | 2 |
| 165 | Me | H | MeO | 2 |
| 166 | Et | H | H | 3 |
| 167 | Et | H | F | 3 |
| 168 | Et | H | Cl | 3 |
| 169 | Et | H | MeO | 3 |
| 170 | Me | H | H | 3 |
| 171 | Me | H | F | 3 |
| 172 | Me | H | Cl | 3 |
| 173 | Me | H | MeO | 3 |

TABLE 6

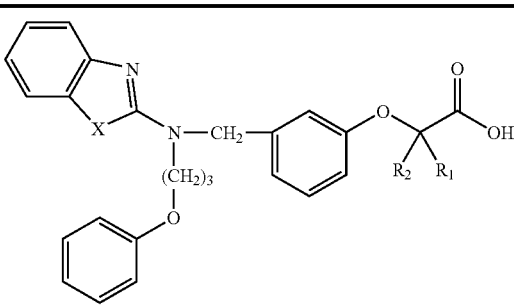

| Examples | R₁ | R₂ | X |
|---|---|---|---|
| 174 | Et | H | NH |
| 175 | Me | H | NH |

TABLE 6-continued

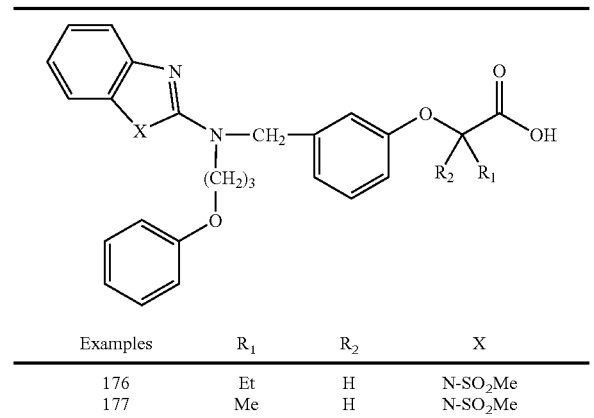

| Examples | $R_1$ | $R_2$ | X |
|---|---|---|---|
| 176 | Et | H | $N-SO_2Me$ |
| 177 | Me | H | $N-SO_2Me$ |

TABLE 7

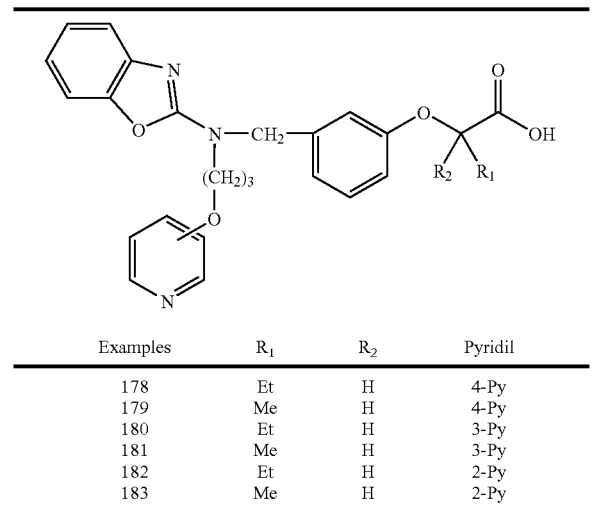

| Examples | $R_1$ | $R_2$ | Pyridil |
|---|---|---|---|
| 178 | Et | H | 4-Py |
| 179 | Me | H | 4-Py |
| 180 | Et | H | 3-Py |
| 181 | Me | H | 3-Py |
| 182 | Et | H | 2-Py |
| 183 | Me | H | 2-Py |

Test Example 1

PPAR activating effects of the compounds of the present invention represented by formula (1) and comparative compounds disclosed in WO 02/46176 (hereinafter referred to as compounds A, B, and C) were determined through the following method (Proc. Natl. Acad. Sci., 92, pp. 7297–7301, 1995; Journal of Lipid Research, 40, pp. 2099–2110, 1999; and Proc. Natl. Acad. Sci, 98, pp. 5306–5311, 2001).

Compound A

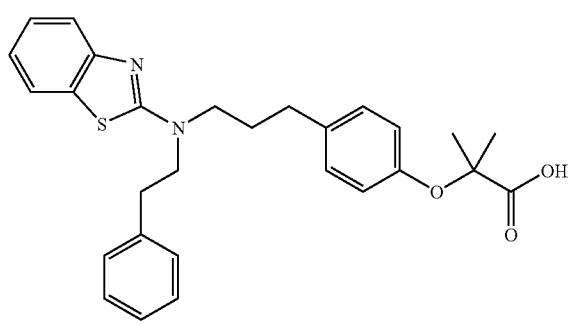

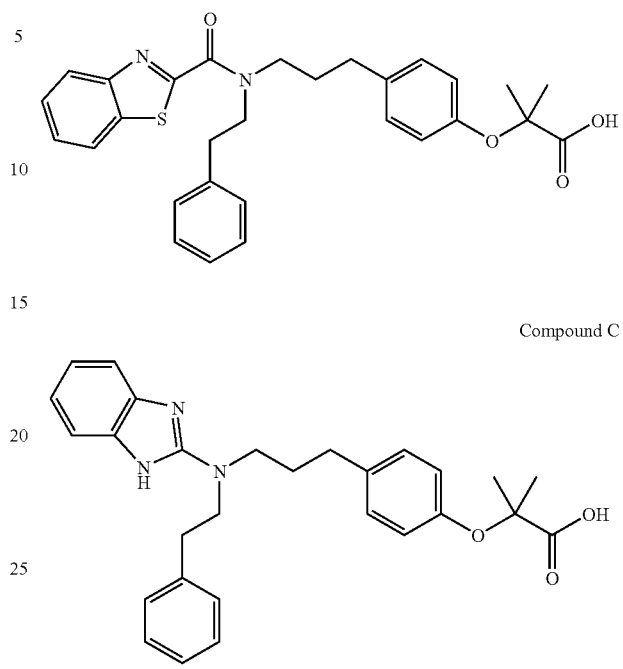

Compound B

Compound C (1) Measurement Methods

Transfection Assay

The COS-7 cell, which is an African green monkey kidney cell line, was used for all transfection assays. Cells were cultured in DMEM medium supplemented with 10% fetal bovine serum, glutamic acid, and an antibiotic under humidified 5% $CO_2$ atmosphere.

The expression vector contained a DNA binding domain for Gal 4, which is a yeast transcription factor, and a binding domain for a ligand of human PPAR. For each isoform of human PPAR, a vector was designed to contain the binding domain for the $1^{st}$–$147^{th}$ aa region of Gal 4 transcription factor and; the $166^{th}$–$467^{th}$ aa region in the case of PPARα $182^{nd}$–$505^{th}$ aa region in the case of PPARγ; $137^{th}$–$441^{st}$ aa region in the case of PPARδ. The firefly luciferase was used for reporter vector, which contained 5 base sequences recognizable by Gal 4 in its promorot region. Transections of cells with plasmids were carried out by lipfectamine and a β-galactosidase expression plasmid was used as an internal control for transfection efficiency.

Transiently transfected cells were incubated in DMEM containing 0.2% FCS with the compounds. And after 16 hours, luciferase activity and β-galactosidase activity of cell lysate were measured.

Each compound was dissolved in and diluted with dimethyl sulfoxide (DMSO), and the DMSO concentration of the DMEM medium (containing 0.2% serum) was adjusted to 0.1% upon treatment of cells. The compounds employed for positive control are WY 14643, troglitazone (Journal of Medicinal Chemistry, pp. 527–550, 2000), and GW 501516 (Proc. Natl. Acad. Sci., 98, pp. 5306–5311, 2001) for PPARα, PPARγ, and PPARδ, respectively.

Table 8 and 9 shows agonist activities for hPPARα, hPPARγ, hPPARδ.

TABLE 8

| Example No. | hPPAR; EC$_{50}$ (μM) | | |
|---|---|---|---|
| | α | γ | δ |
| 1 | 0.01 | >100 | 1.6 |
| 2 | 0.01 | 7.3 | 2.5 |
| 3 | 0.01 | >100 | 1.8 |
| 6 | 0.07 | 3.5 | >100 |
| 9 | 0.01 | 1.2 | 2.4 |
| 12 | 1.2 | >100 | >100 |
| 13 | 0.01 | >50 | 2 |
| 14 | 0.0002 | >100 | 1.7 |
| 15 | 0.05 | >100 | 1.5 |
| 18 | 0.07 | 1.2 | >100 |
| 19 | 0.0001 | 1.2 | >100 |
| 20 | 0.01 | 1.2 | 2.0 |
| 24 | 0.03 | 1.4 | 2.3 |

TABLE 9

| Example No. | hPPAR; EC$_{50}$ (μM) | | |
|---|---|---|---|
| | α | γ | δ |
| 31 | 0.09 | >100 | >50 |
| 34 | 0.06 | 1.2 | 1.6 |
| 35 | 0.02 | 1.2 | 1.6 |
| 36 | 0.05 | 2.1 | 1.6 |
| 37 | 0.07 | 4.2 | 1.5 |
| 38 | 0.05 | 1.5 | 1.4 |
| 39 | 0.08 | 9.1 | 1.6 |
| 41 | 0.04 | 2 | >50 |
| 43 | 0.07 | >100 | 5.3 |
| 44 | 0.08 | >100 | 1.6 |
| 45 | 0.01 | 6.3 | 1.8 |
| 46 | 0.01 | >100 | 1.8 |
| 47 | 0.04 | >50 | 1.5 |
| 48 | 0.08 | 5.2 | 2 |
| 49 | 0.02 | 1.5 | 1.5 |
| 50 | 0.04 | 2.6 | 1.4 |
| 51 | 0.03 | 3.8 | 1.4 |
| 52 | 0.01 | 2 | 0.4 |
| 53 | 0.06 | 3.9 | 1.9 |
| 78 | 0.03 | 1.1 | >100 |
| Compound A | 0.1 | 0.2 | 0.4 |
| Compound B | 0.12 | 0.7 | 0.9 |
| Compound C | — | — | — |

The hPPARα selectivities of compounds A and B were found to be low, and specifically, their levels are only less than 10-fold at EC$_{50}$ values of hPPARγ and hPPARδ. In addition, compound C was found to exhibit no activation of any hPPAR isoform. In contrast, the compounds of the present invention exhibited excellent hPPARα selectivity, clearly revealing that the compounds of the present invention have high hPPARα selectivity as compared with compounds A, B, and C disclosed in WO 02/46176.

FIG. 1 show activation factors, with respect to each hPPAR isoform, of the compounds of the present invention (Examples 1) as determined at corresponding EC$_{50}$ values in activation of hPPARα and at concentrations 10 times those of EC$_{50}$ values. The activation factor is defined as a ratio of activity of test compound to that of control, which contains only the solvent (DMSO) and no test compound. As is clear from this FIGURE, the compound of Example 1 exhibited substantially no activation of hPPARγ and hPPARδ even at the 10-fold concentration of EC$_{50}$ value in activation of hPPARα. The results indicate that the compounds of the present invention can be used as excellent hPPARα-selective activators.

What is claimed is:

1. A compound represented by the following formula (1):

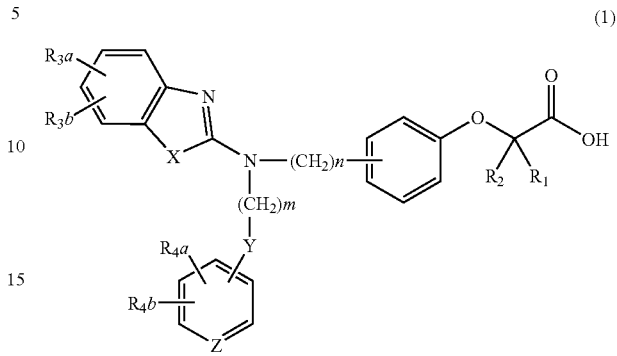

wherein each of $R_1$ and $R_2$, which may be identical to or different from each other, represents hydrogen, methyl, or ethyl; each of $R_{3a}$, $R_{3b}$, $R_{4a}$, and $R_{4b}$, which may be identical to or different from each other, represents hydrogen, halogen, nitro, hydroxyl, $C_{1-4}$ alkyl, trifluoromethyl, $C_{1-4}$ alkoxy, $C_{1-4}$ alkylcarbonyloxy, di-$C_{1-4}$ alkylamino, $C_{1-4}$ alkylsulfonyloxy, $C_{1-4}$ alkylsulfonyl, $C_{1-4}$ alkylsulfinyl, or $C_{1-4}$ alkylthio, or $R_{3a}$ and $R_{3b}$, or $R_{4a}$ and $R_{4b}$ optionally are linked together to form an alkylenedioxy group; X represents oxygen, sulfur or N—$R_5$, wherein $R_5$ represents hydrogen, $C_{1-4}$ alkyl, $C_{1-4}$ alkylsulfonyl, or $C_{1-4}$ alkyloxycarbonyl group; Y represents oxygen, S(O)$_1$, wherein 1 is 0,1 or 2, carbonyl, carbonylamino, aminocarbonyl, sulfonylamino, aminosulfonyl, or NH; n is a number from 1 to 6; and m is a number from 2 to 6, or a salt thereof.

2. The compound according to claim 1, wherein X and Y represent oxygen.

3. A compound selected from the group consisting of 2-[3-[[N-(Benzoxazol-2-yl)-N-3-(4-fluorophenoxy)propyl]aminomethyl]phenoxy]butyric acid, 2-[3-[[N-(Benzoxazol-2-yl)-N-2-(4-chlorophenoxy)ethyl]aminomethyl]phenoxy]butyric acid, 2-[3-[[N-(Benzoxazol-2-yl)-N-2-(4-chlorophenoxy)ethyl]aminomethyl]phenoxy]butyric acid, 2-[3-[[N-(Benzoxazol-2-yl)-N-3-phenoxypropyl]aminomethyl]phenoxy]propionic acid, 2-[3-[[N-(Benzoxazol-2-yl)-N-3-phenoxypropyl]aminomethyl]phenoxy]acetic acid, 2-[3-[[N-(Benzoxazol-2-yl)-N-3-phenoxypropyl]aminomethyl]phenoxy]butyric acid, 2-[3-[[N-(Benzoxazol-2-yl)-N-3-(4-methoxyphenoxy)propyl]aminomethyl]phenoxy]butyric acid, 2-[3-[[N-(Benzoxazol-2-yl)-N-3-(4-methoxyphenoxy)propyl]aminomethyl]phenoxy]propionic acid and a salt thereof.

4. A pharmaceutical composition comprising a compound or a salt thereof as recited in claim 1, 2 or 3 and a pharmacologically acceptable carrier.

5. A method for treating pathological conditions selected from the group consisting of hyperlipidemia, arteriosclerosis, diabetes, complications of diabetes, and inflammation comprising:
    administering to a subject in need thereof an effective amount of a compound or a salt thereof as recited in claim 1, 2 or 3.

* * * * *

UNITED STATES PATENT AND TRADEMARK OFFICE
CERTIFICATE OF CORRECTION

PATENT NO. : 7,109,226 B2  
APPLICATION NO. : 10/933467  
DATED : September 19, 2006  
INVENTOR(S) : Yukiyoshi Yamazaki et al.

Page 1 of 2

It is certified that error appears in the above-identified patent and that said Letters Patent is hereby corrected as shown below:

Face of Patent, (57) ABSTRACT, Formula 1,

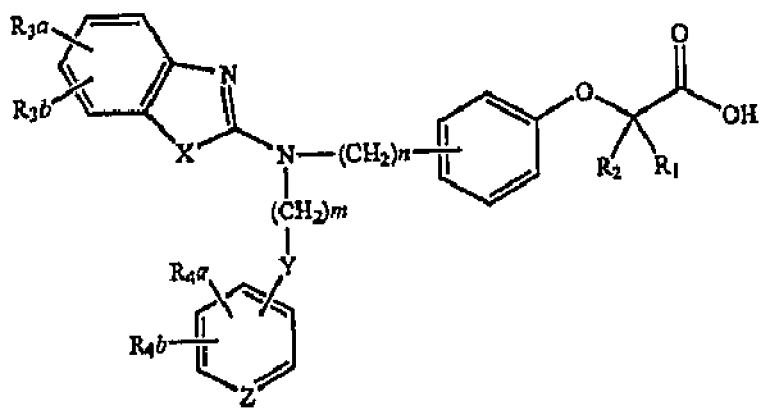

should read

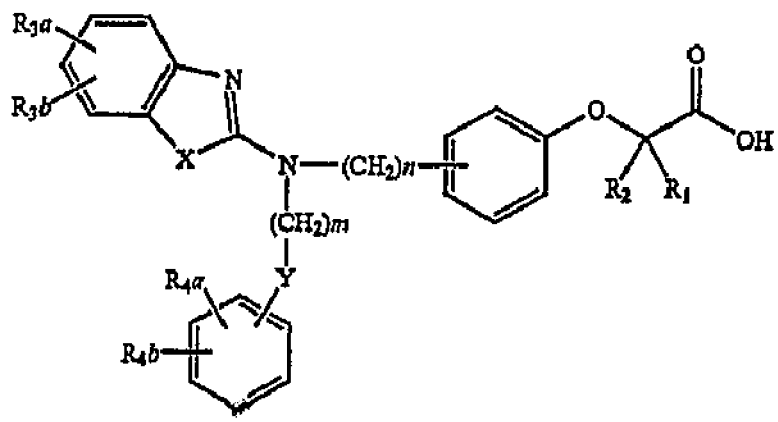

UNITED STATES PATENT AND TRADEMARK OFFICE
CERTIFICATE OF CORRECTION

PATENT NO.       : 7,109,226 B2  
APPLICATION NO.  : 10/933467  
DATED            : September 19, 2006  
INVENTOR(S)      : Yukiyoshi Yamazaki et al.

It is certified that error appears in the above-identified patent and that said Letters Patent is hereby corrected as shown below:

Column 74, line 5, Formula 1,

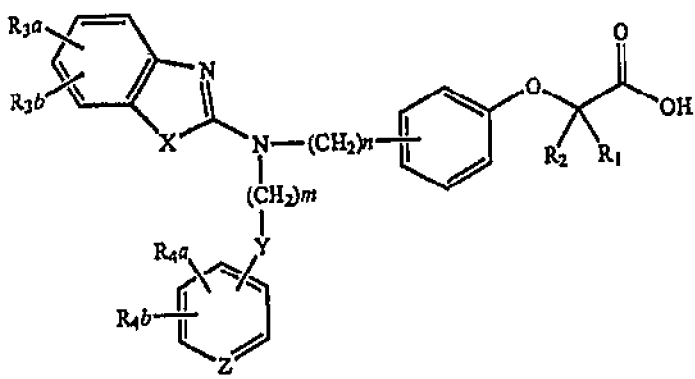

should read

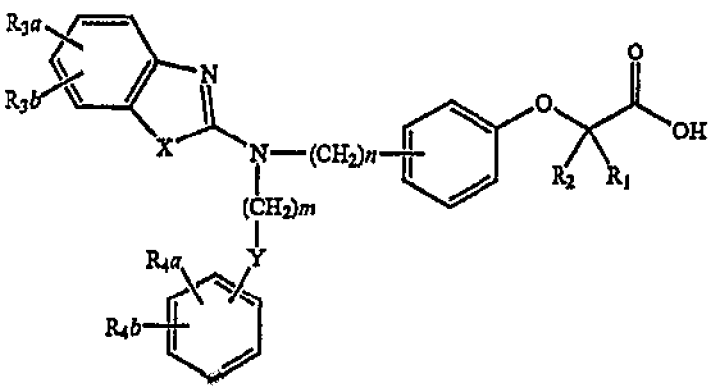

Signed and Sealed this

Seventeenth Day of July, 2007

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,109,226 B2 | Page 1 of 1 |
| APPLICATION NO. | : 10/933467 | |
| DATED | : September 19, 2006 | |
| INVENTOR(S) | : Yukiyoshi Yamazaki et al. | |

It is certified that error appears in the above-identified patent and that said Letters Patent is hereby corrected as shown below:

Column 74, lines 43-44: "(4-chlorophenoxy)" should read --(4-fluorophenoxy)--

Signed and Sealed this
Thirty-first Day of May, 2011

David J. Kappos
*Director of the United States Patent and Trademark Office*